(12) United States Patent
Chou et al.

(10) Patent No.: US 10,416,151 B2
(45) Date of Patent: *Sep. 17, 2019

(54) DEVICE AND SYSTEM FOR COLLECTING AND ANALYZING VAPOR CONDENSATE, PARTICULARLY EXHALED BREATH CONDENSATE, AS WELL AS METHOD OF USING THE SAME

(71) Applicant: Essenlix Corporation, Monmouth Junction, NJ (US)

(72) Inventors: Stephen Y. Chou, Princeton, NJ (US); Wei Ding, East Windsor, NJ (US)

(73) Assignee: ESSENLIX CORPORATION, Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/123,651

(22) Filed: Sep. 6, 2018

(65) Prior Publication Data

US 2019/0017996 A1 Jan. 17, 2019

Related U.S. Application Data

(63) Continuation of application No. 15/561,014, filed as application No. PCT/US2016/051794 on Sep. 14, 2016, now Pat. No. 10,132,794.

(Continued)

(51) Int. Cl.
*G01N 33/497* (2006.01)
*A61B 5/083* (2006.01)
(Continued)

(52) U.S. Cl.
CPC ......... *G01N 33/497* (2013.01); *A61B 5/0836* (2013.01); *A61B 5/097* (2013.01);
(Continued)

(58) Field of Classification Search
CPC ..... A61B 5/0836; A61B 5/0935; A61B 5/097; A61M 2205/3569; A61M 2230/43;
(Continued)

(56) References Cited

U.S. PATENT DOCUMENTS 3,368,872 A 2/1968 Natelson
3,447,863 A 6/1969 Patterson
(Continued)

FOREIGN PATENT DOCUMENTS

CN 1299466 6/2001
CN 1302229 7/2001
(Continued)

OTHER PUBLICATIONS

Written Opinion for PCT/US2016/051794 established by ISA/KR dated Dec. 8, 2016.
(Continued)

*Primary Examiner* — David A Rogers

(57) ABSTRACT

The present invention is related to the field of bio/chemical sensing, assays and applications. Particularly, the present invention is related to collecting a small amount of a vapor condensate sample (e.g. the exhaled breath condensate (EBC) from a subject of a volume as small as 10 fL (femto-Liter) in a single drop), preventing or significantly reducing an evaporation of the collected vapor condensate sample, analyzing the sample, analyzing the sample by mobile-phone, and performing such collection and analysis by a person without any professionals.

30 Claims, 18 Drawing Sheets

Related U.S. Application Data

(60) Provisional application No. 62/305,123, filed on Mar. 8, 2016, provisional application No. 62/293,188, filed on Feb. 9, 2016, provisional application No. 62/218,455, filed on Sep. 14, 2015.

(51) Int. Cl.
| | |
|---|---|
| *A61B 5/093* | (2006.01) |
| *A61B 5/097* | (2006.01) |
| *G01N 21/01* | (2006.01) |
| *G01N 33/58* | (2006.01) |
| *G01N 1/28* | (2006.01) |
| *B01L 3/00* | (2006.01) |
| *G01N 1/22* | (2006.01) |

(52) U.S. Cl.
CPC ............ *A61B 5/0935* (2013.01); *B01L 3/502* (2013.01); *G01N 1/2813* (2013.01); *G01N 21/01* (2013.01); *G01N 33/58* (2013.01); *A61M 2205/3569* (2013.01); *A61M 2230/43* (2013.01); *B01L 2200/142* (2013.01); *B01L 2300/046* (2013.01); *B01L 2300/0636* (2013.01); *B01L 2300/0816* (2013.01); *B01L 2400/0481* (2013.01); *G01N 2001/2244* (2013.01); *G01N 2001/2276* (2013.01); *G01N 2021/0118* (2013.01); *G01N 2021/0181* (2013.01); *G01N 2033/4975* (2013.01)

(58) Field of Classification Search
CPC ...... G01N 33/497; G01N 21/01; G01N 33/58; G01N 2021/011; G01N 2021/0181; G01N 2033/4975; G01N 1/405; G01N 2001/4033

See application file for complete search history.

(56) References Cited

U.S. PATENT DOCUMENTS

| | | |
|---|---|---|
| 3,895,661 A | 7/1975 | Praglin et al. |
| 3,925,166 A | 12/1975 | Blume |
| 3,992,158 A | 11/1976 | Przybylowicz et al. |
| 4,022,521 A | 5/1977 | Hall et al. |
| 4,066,412 A | 1/1978 | Johnson et al. |
| 4,088,448 A | 5/1978 | Lilja et al. |
| 4,171,866 A | 10/1979 | Tolles |
| 4,255,384 A | 3/1981 | Kitajima et al. |
| 4,258,001 A | 3/1981 | Pierce et al. |
| 4,329,054 A | 5/1982 | Bachalo |
| 4,427,294 A | 1/1984 | Nardo |
| 4,430,436 A | 2/1984 | Koyama et al. |
| 4,745,075 A | 5/1988 | Hadfield et al. |
| 4,806,311 A | 2/1989 | Greenquist |
| 4,883,642 A | 11/1989 | Bisconte |
| 4,906,439 A | 3/1990 | Grenner |
| 4,911,782 A | 3/1990 | Brown |
| 4,950,455 A | 8/1990 | Smith |
| 5,039,487 A | 8/1991 | Smith |
| 5,096,836 A | 3/1992 | Macho et al. |
| 5,122,284 A | 6/1992 | Braynin et al. |
| 5,132,097 A | 7/1992 | Van Deusen et al. |
| 5,169,601 A | 12/1992 | Ohta et al. |
| 5,188,968 A | 2/1993 | Kano et al. |
| 5,223,219 A | 6/1993 | Subramanian et al. |
| 5,281,540 A | 1/1994 | Merkh et al. |
| 5,321,975 A | 6/1994 | Wardlaw |
| 5,362,648 A | 11/1994 | Koreyasu et al. |
| 5,413,732 A | 5/1995 | Buhl et al. |
| 5,427,959 A | 6/1995 | Nishimura et al. |
| 5,431,880 A | 7/1995 | Kramer |
| 5,591,403 A | 1/1997 | Gavin et al. |
| 5,623,415 A | 4/1997 | O'Bryan et al. |
| 5,753,456 A | 5/1998 | Naqui et al. |
| 5,768,407 A | 6/1998 | Shen et al. |
| 5,858,648 A | 1/1999 | Steel et al. |
| 5,879,628 A | 3/1999 | Ridgeway et al. |
| 5,888,834 A | 3/1999 | Ishikawa et al. |
| 5,939,326 A | 8/1999 | Chupp et al. |
| 5,948,686 A | 9/1999 | Wardlaw |
| 6,004,821 A | 12/1999 | Levine et al. |
| 6,016,367 A | 1/2000 | Benedetti et al. |
| 6,017,767 A | 1/2000 | Chandler |
| 6,022,734 A | 2/2000 | Wardlaw |
| 6,106,778 A | 8/2000 | Oku et al. |
| 6,235,536 B1 | 5/2001 | Wardlaw |
| 6,350,613 B1 | 2/2002 | Wardlaw et al. |
| 6,358,475 B1 | 3/2002 | Berndt |
| 6,429,027 B1 | 8/2002 | Chee et al. |
| 6,503,760 B2 | 1/2003 | Malmqvist et al. |
| 6,551,554 B1 | 4/2003 | Vermeiden et al. |
| 6,623,701 B1 | 9/2003 | Eichele et al. |
| 6,632,652 B1 | 10/2003 | Austin et al. |
| 6,723,290 B1 | 4/2004 | Wardlaw |
| 6,844,201 B2 | 1/2005 | Malmqvist et al. |
| 6,866,823 B2 | 3/2005 | Wardlaw |
| 6,869,570 B2 | 3/2005 | Levine |
| 6,921,514 B1 | 7/2005 | Vetter et al. |
| 6,929,953 B1 | 8/2005 | Levine |
| 7,101,341 B2 | 9/2006 | Tsukashima et al. |
| 7,179,423 B2 | 2/2007 | Bohm et al. |
| 7,282,367 B2 | 10/2007 | Kawamura |
| 7,393,658 B2 | 7/2008 | Carbonell et al. |
| 7,410,617 B2 | 8/2008 | Sakamoto |
| 7,410,807 B2 | 8/2008 | D'Aurora |
| 7,468,160 B2 | 12/2008 | Thompson et al. |
| 7,510,841 B2 | 3/2009 | Stuelpnagel et al. |
| 7,731,901 B2 | 6/2010 | Wardlaw |
| 7,738,094 B2 | 6/2010 | Goldberg |
| 7,850,916 B2 | 12/2010 | Wardlaw |
| 7,862,773 B2 | 1/2011 | Ibrahim |
| 7,863,411 B2 | 1/2011 | Hammond et al. |
| 7,897,376 B2 | 3/2011 | Porter et al. |
| 7,901,897 B2 | 3/2011 | Stuelpnagel et al. |
| 7,903,241 B2 | 3/2011 | Wardlaw et al. |
| 7,929,121 B2 | 4/2011 | Wardlaw et al. |
| 7,929,122 B2 | 4/2011 | Wardlaw et al. |
| 7,943,093 B2 | 5/2011 | Adrien et al. |
| 7,951,599 B2 | 5/2011 | Levine et al. |
| 7,995,194 B2 | 8/2011 | Wardlaw et al. |
| 8,045,165 B2 | 10/2011 | Wardlaw et al. |
| 8,077,296 B2 | 12/2011 | Wardlaw et al. |
| 8,081,303 B2 | 12/2011 | Levine et al. |
| 8,133,738 B2 | 3/2012 | Levine et al. |
| 8,158,434 B2 | 4/2012 | Wardlaw |
| 8,221,985 B2 | 7/2012 | Wardlaw et al. |
| 8,241,572 B2 | 8/2012 | Wardlaw |
| 8,269,954 B2 | 9/2012 | Levine et al. |
| 8,284,384 B2 | 10/2012 | Levine et al. |
| 8,310,658 B2 | 11/2012 | Wardlaw et al. |
| 8,310,659 B2 | 11/2012 | Wardlaw et al. |
| 8,319,954 B2 | 11/2012 | Wardlaw et al. |
| 8,326,008 B2 | 12/2012 | Lalpuria et al. |
| 8,338,579 B2 | 12/2012 | Adams et al. |
| 8,361,799 B2 | 1/2013 | Levine et al. |
| 8,367,012 B2 | 2/2013 | Wardlaw |
| 8,462,332 B2 | 6/2013 | Pugia et al. |
| 8,467,063 B2 | 6/2013 | Wardlaw et al. |
| 8,472,693 B2 | 6/2013 | Davis et al. |
| 8,481,282 B2 | 7/2013 | Levine et al. |
| 8,502,963 B2 | 8/2013 | Levine et al. |
| 8,513,032 B2 | 8/2013 | Jablonski et al. |
| 8,569,076 B2 | 10/2013 | Wardlaw et al. |
| 8,594,768 B2 | 11/2013 | Phillips |
| 8,604,161 B2 | 12/2013 | Hammond et al. |
| 8,628,952 B2 | 1/2014 | Stuelpnagel et al. |
| 8,633,013 B2 | 1/2014 | Kaiser et al. |
| 8,638,427 B2 | 1/2014 | Wardlaw et al. |
| 8,741,630 B2 | 6/2014 | Dickinson et al. |
| 8,750,966 B2 | 6/2014 | Phillips |
| 8,778,687 B2 | 7/2014 | Levine et al. |
| 8,781,203 B2 | 7/2014 | Davis et al. |
| 8,796,186 B2 | 8/2014 | Shirazi |

(56) References Cited

U.S. PATENT DOCUMENTS

| | | |
|---|---|---|
| 8,797,527 B2 | 8/2014 | Hukari et al. |
| 8,835,186 B2 | 9/2014 | Jablonski et al. |
| 8,837,803 B2 | 9/2014 | Wang et al. |
| 8,842,264 B2 | 9/2014 | Wardlaw et al. |
| 8,885,154 B2 | 11/2014 | Wardlaw et al. |
| 8,906,700 B2 | 12/2014 | Lim et al. |
| 8,911,815 B2 | 12/2014 | Kram et al. |
| 8,974,732 B2 | 3/2015 | Lalpuria et al. |
| 8,994,930 B2 | 3/2015 | Levine et al. |
| 9,023,641 B2 | 5/2015 | Rodriguez et al. |
| 9,044,268 B2 | 6/2015 | Phillips |
| 9,084,995 B2 | 7/2015 | Wardlaw |
| 9,086,408 B2 | 7/2015 | Egan et al. |
| 9,097,640 B2 | 8/2015 | Goldberg et al. |
| 9,199,233 B2 | 12/2015 | Wardlaw |
| 9,274,094 B2 | 3/2016 | Wardlaw et al. |
| 9,291,617 B2 | 3/2016 | Levine et al. |
| 9,322,835 B2 | 4/2016 | Wardlaw |
| 9,347,962 B2 | 5/2016 | Salsman |
| 9,354,159 B2 | 5/2016 | Vaartstra |
| 9,395,365 B2 | 7/2016 | Levine et al. |
| 9,469,871 B2 | 10/2016 | Bearinger et al. |
| 9,523,670 B2 | 12/2016 | Mueller et al. |
| 2001/0031500 A1 | 10/2001 | Kawamura |
| 2002/0028158 A1 | 3/2002 | Wardlaw |
| 2002/0126271 A1 | 9/2002 | Berndt |
| 2003/0068614 A1 | 4/2003 | Cima et al. |
| 2003/0109059 A1 | 6/2003 | Adrien et al. |
| 2003/0138971 A1 | 7/2003 | D'Aurora |
| 2004/0131345 A1 | 7/2004 | Kylberg et al. |
| 2004/0156755 A1 | 8/2004 | Levine |
| 2004/0185482 A1 | 9/2004 | Stuelpnagel et al. |
| 2004/0229280 A1 | 11/2004 | Hammond et al. |
| 2004/0259162 A1 | 12/2004 | Kappel et al. |
| 2005/0026161 A1 | 2/2005 | Jablonski et al. |
| 2005/0032138 A1 | 2/2005 | Lathrop et al. |
| 2005/0106074 A1 | 5/2005 | Sakamoto |
| 2005/0221377 A1 | 10/2005 | Ibrahrim |
| 2005/0254995 A1 | 11/2005 | Sostek et al. |
| 2006/0051253 A1 | 3/2006 | Gausepohl |
| 2006/0062440 A1 | 3/2006 | Hollars et al. |
| 2006/0078892 A1 | 4/2006 | Hammond et al. |
| 2006/0090658 A1 | 5/2006 | Phillips |
| 2006/0160134 A1 | 7/2006 | Melker et al. |
| 2007/0087442 A1 | 4/2007 | Wardlaw |
| 2007/0243117 A1 | 10/2007 | Wardlaw |
| 2008/0028962 A1 | 2/2008 | Phillips |
| 2008/0064093 A1 | 3/2008 | Porter et al. |
| 2008/0131883 A1 | 6/2008 | Adams et al. |
| 2008/0187466 A1 | 8/2008 | Wardlaw |
| 2008/0214947 A1 | 9/2008 | Hunt et al. |
| 2008/0268474 A1 | 10/2008 | Hammond et al. |
| 2008/0274564 A1 | 11/2008 | D'Aurora |
| 2008/0286152 A1 | 11/2008 | Schmidt et al. |
| 2009/0011451 A1 | 1/2009 | Rodriguez et al. |
| 2009/0155123 A1 | 6/2009 | Williams et al. |
| 2009/0176201 A1 | 7/2009 | Jablonski et al. |
| 2009/0191641 A1 | 7/2009 | Chiapperi et al. |
| 2009/0211344 A1 | 8/2009 | Wang |
| 2009/0227472 A1 | 9/2009 | Stuelpnagel, Jr. et al. |
| 2009/0233329 A1 | 9/2009 | Rodriguez et al. |
| 2009/0237665 A1 | 9/2009 | Wardlaw et al. |
| 2009/0238437 A1 | 9/2009 | Levine et al. |
| 2009/0238438 A1 | 9/2009 | Wardlaw et al. |
| 2009/0238439 A1 | 9/2009 | Wardlaw et al. |
| 2009/0239257 A1 | 9/2009 | Levine et al. |
| 2009/0246781 A1 | 10/2009 | Klem et al. |
| 2009/0251683 A1 | 10/2009 | Wardlaw et al. |
| 2009/0252399 A1 | 10/2009 | Wardlaw et al. |
| 2009/0253218 A1 | 10/2009 | Wardlaw et al. |
| 2009/0257632 A1 | 10/2009 | Lalpuria et al. |
| 2009/0258371 A1 | 10/2009 | Wardlaw et al. |
| 2009/0298716 A1 | 12/2009 | Stuelpnagel, Jr. et al. |
| 2010/0081583 A1 | 4/2010 | Shirazi |
| 2010/0085067 A1 | 4/2010 | Gabriel et al. |
| 2010/0151593 A1 | 6/2010 | D'Aurora |
| 2010/0216248 A1 | 8/2010 | Wardlaw |
| 2010/0255509 A1 | 10/2010 | Levine et al. |
| 2010/0255605 A1 | 10/2010 | Wardlaw |
| 2010/0272345 A1 | 10/2010 | Wardlaw |
| 2010/0273244 A1 | 10/2010 | Wardlaw |
| 2010/0291562 A1 | 11/2010 | Adler |
| 2011/0009297 A1 | 1/2011 | Jones et al. |
| 2011/0059481 A1 | 3/2011 | Wardlaw et al. |
| 2011/0092389 A1 | 4/2011 | Dickinson et al. |
| 2011/0149061 A1 | 6/2011 | Wardlaw et al. |
| 2011/0149277 A1 | 6/2011 | Pugia et al. |
| 2011/0164803 A1 | 7/2011 | Wang et al. |
| 2011/0193957 A1 | 8/2011 | Wardlaw et al. |
| 2011/0206557 A1 | 8/2011 | Phan et al. |
| 2011/0230644 A1 | 9/2011 | Jablonski et al. |
| 2011/0230740 A1 | 9/2011 | Levine et al. |
| 2011/0244593 A1 | 10/2011 | Wardlaw |
| 2011/0256573 A1 | 10/2011 | Davis et al. |
| 2011/0294198 A1 | 12/2011 | Wardlaw |
| 2011/0294200 A1 | 12/2011 | Wardlaw et al. |
| 2012/0021456 A1 | 1/2012 | Levine et al. |
| 2012/0034647 A1 | 2/2012 | Herzog et al. |
| 2012/0099108 A1 | 4/2012 | Wardlaw et al. |
| 2012/0107799 A1 | 5/2012 | Daum |
| 2012/0108787 A1 | 5/2012 | Lue |
| 2012/0147357 A1 | 6/2012 | Wardlaw et al. |
| 2012/0157332 A1 | 6/2012 | Kumar et al. |
| 2012/0164682 A1 | 6/2012 | Levine et al. |
| 2012/0164719 A1 | 6/2012 | Levine et al. |
| 2012/0195489 A1 | 8/2012 | Levine et al. |
| 2013/0029373 A1 | 1/2013 | Levine et al. |
| 2013/0040842 A1 | 2/2013 | Lim et al. |
| 2013/0052331 A1 | 2/2013 | Kram et al. |
| 2013/0065788 A1 | 3/2013 | Glezer et al. |
| 2013/0078668 A1 | 3/2013 | Levine et al. |
| 2013/0102018 A1 | 4/2013 | Schentag et al. |
| 2013/0170729 A1 | 7/2013 | Wardlaw et al. |
| 2013/0176551 A1 | 7/2013 | Wardlaw et al. |
| 2013/0203107 A1 | 8/2013 | Lalpuria et al. |
| 2013/0208972 A1 | 8/2013 | Levine et al. |
| 2013/0209332 A1 | 8/2013 | Wardlaw |
| 2013/0217146 A1 | 8/2013 | Wardlaw |
| 2013/0265054 A1 | 10/2013 | Lowery, Jr. et al. |
| 2013/0309679 A1 | 11/2013 | Ismagilov et al. |
| 2014/0004554 A1 | 1/2014 | Davis et al. |
| 2014/0248647 A1 | 9/2014 | Levine et al. |
| 2014/0315242 A1 | 10/2014 | Rodriguez et al. |
| 2014/0368631 A1 | 12/2014 | Wardlaw et al. |
| 2015/0036131 A1 | 2/2015 | Salsman |
| 2015/0097939 A9 | 4/2015 | Wardlaw et al. |
| 2015/0253321 A1 | 9/2015 | Chou et al. |
| 2015/0317506 A1 | 11/2015 | Xie et al. |
| 2015/0323519 A1 | 11/2015 | Wardlaw |
| 2016/0025637 A1 | 1/2016 | Halverson et al. |
| 2016/0033496 A1 | 2/2016 | Chou et al. |
| 2016/0047797 A1 | 2/2016 | Levine et al. |
| 2016/0245797 A1 | 8/2016 | Ahmad et al. |
| 2016/0266091 A1 | 9/2016 | Levine et al. |
| 2017/0021356 A1 | 1/2017 | Dority et al. |
| 2017/0038401 A1 | 2/2017 | Holmes et al. |

FOREIGN PATENT DOCUMENTS

| | | |
|---|---|---|
| CN | 1166950 | 9/2004 |
| CN | 1188217 | 2/2005 |
| CN | 102027369 | 4/2011 |
| EP | 0961110 | 12/1999 |
| EP | 2290100 | 3/2011 |
| EP | 2439515 | 4/2012 |
| EP | 2554987 | 2/2013 |
| EP | 3026433 | 6/2016 |
| WO | 1991020009 | 12/1991 |
| WO | 1999044743 | 9/1999 |
| WO | 1999045385 | 9/1999 |
| WO | 2005114145 | 12/2005 |
| WO | 2005100539 | 1/2006 |
| WO | 2007112332 | 10/2007 |
| WO | 2009117652 | 9/2009 |

(56) References Cited

FOREIGN PATENT DOCUMENTS

| WO | 2009117664 | 9/2009 |
|----|------------|--------|
| WO | 2009117678 | 9/2009 |
| WO | 2009117682 | 9/2009 |
| WO | 2009124186 | 10/2009 |
| WO | 2009124190 | 10/2009 |
| WO | 2009126800 | 10/2009 |
| WO | 2010115026 | 10/2010 |
| WO | 2014089468 | 6/2014 |
| WO | 2014183049 | 11/2014 |
| WO | 2014205576 | 12/2014 |

OTHER PUBLICATIONS

Van Vliet, Dillys et al., Prediction of asthma exacerbations in children by innovative exhaled inflammatory markers: Results of a longitudinal study, PLOS ONE, Mar. 23, 2015, vol. 10. No. 3, e0119434.

Fig. 1. Exemplary device and methods of collecting exhaled breath condensate (EBC) using a SiEBC (Single-drop EBC Collector/Analyzer)

Fig. 2 Different formations of EBC at closed configuration of SiEBCA depends on spacer height

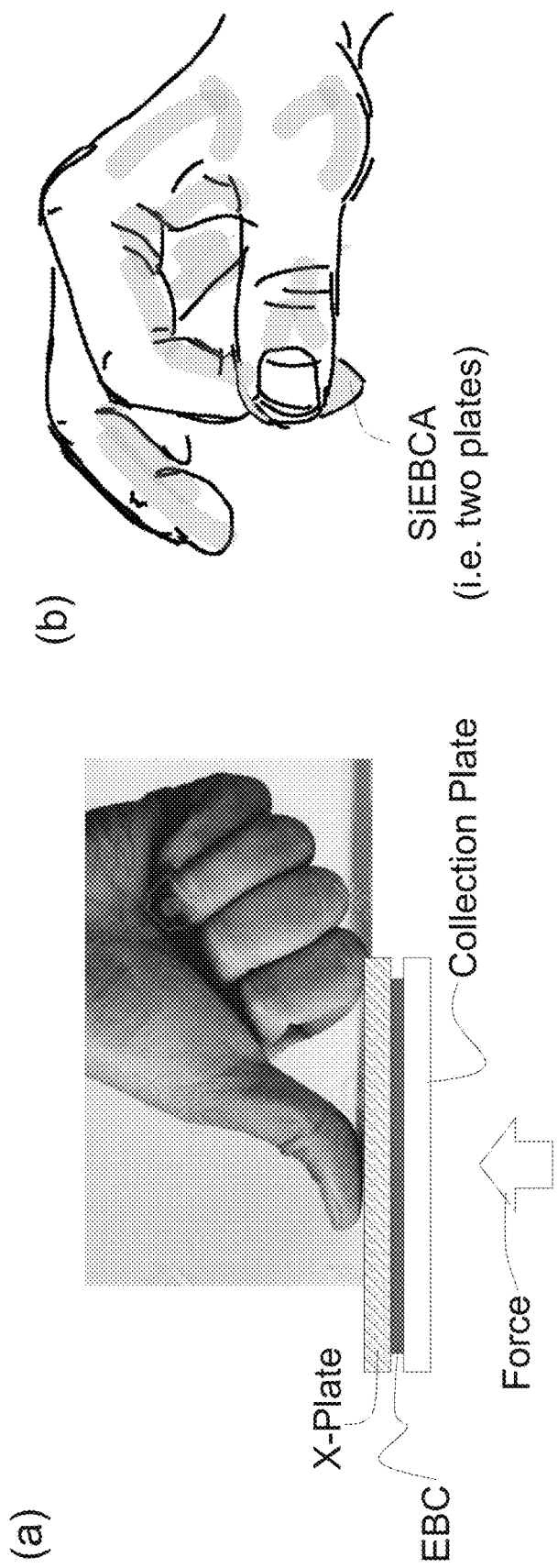
Fig. 5. Methods of pressing the plates of SiEBCA by human hand

Fig. 6. Experimental data of EBC Droplets sizes and density on the collecting plate (untreated PMMA film) at the "open configuration"

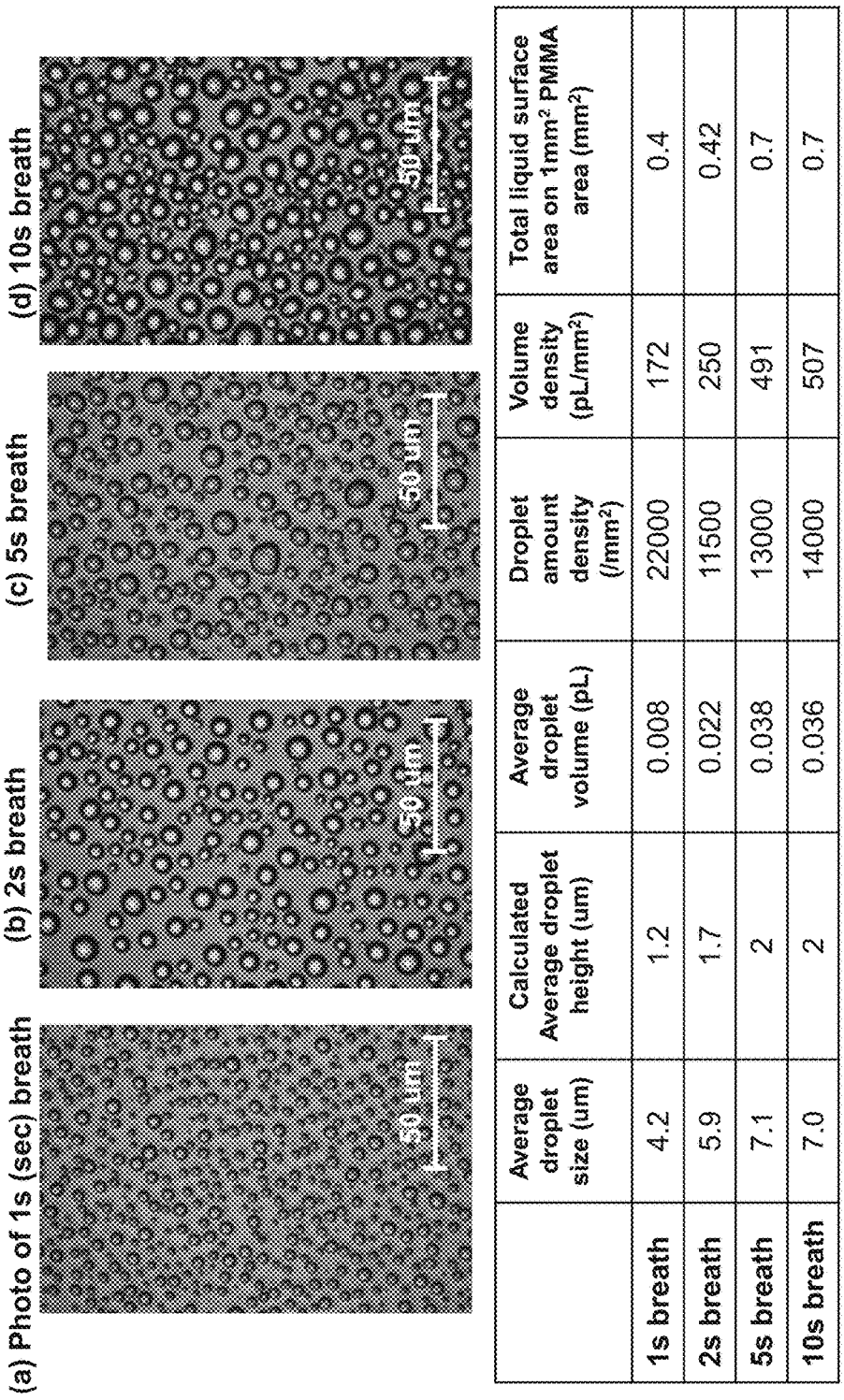

|  | Average droplet size (um) | Calculated Average droplet height (um) | Average droplet volume (pL) | Droplet amount density (/mm²) | Volume density (pL/mm²) | Total liquid surface area on 1mm² PMMA area (mm²) |
|---|---|---|---|---|---|---|
| 1s breath | 4.2 | 1.2 | 0.008 | 22000 | 172 | 0.4 |
| 2s breath | 5.9 | 1.7 | 0.022 | 11500 | 250 | 0.42 |
| 5s breath | 7.1 | 2 | 0.038 | 13000 | 491 | 0.7 |
| 10s breath | 7.0 | 2 | 0.036 | 14000 | 507 | 0.7 |

* *Breath onto untreated PMMA collection plate.*
** *Calculated Average droplet height is based on the wetting contact angle of water on PMMA.*
*** *Volume density = Average droplet volume × Droplet amount density*

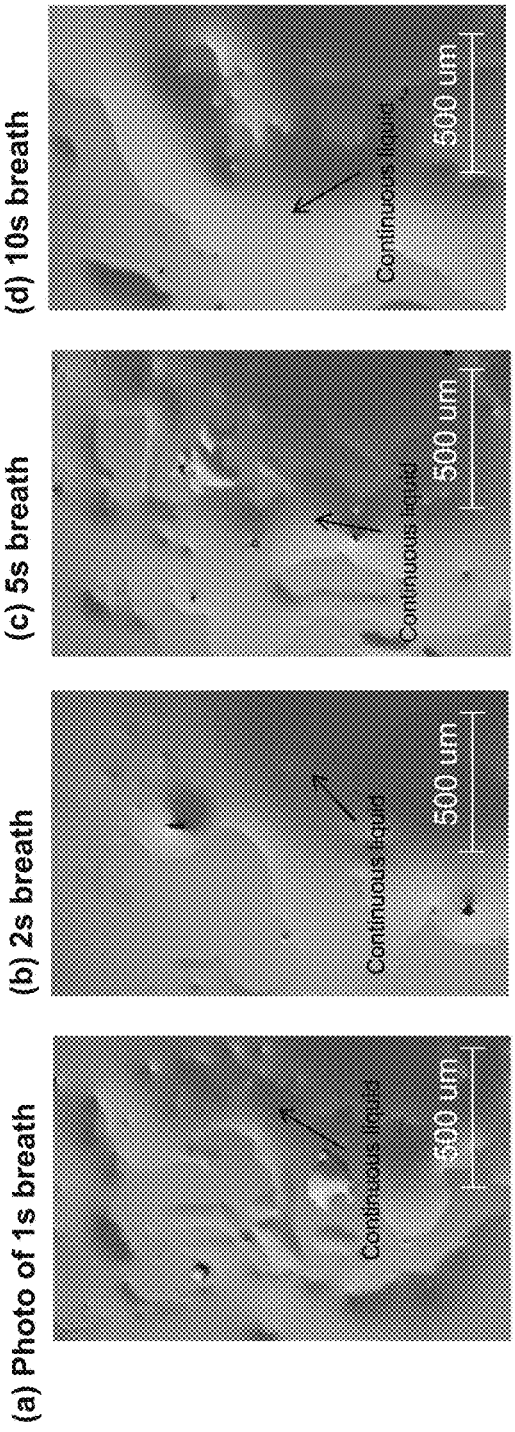

Fig. 7. Experimental data of EBC droplets sizes and density on collecting plate (treated PMMA film) at the open configuration of the plates

| | Volume density (pL/mm²) (Assume same as before) | Total liquid surface area on 1mm² PMMA area (mm²) | Calculated average liquid thickness (um) |
|---|---|---|---|
| | Form Mostly Continuous (with holes) breath liquid film | | |
| 1s breath | 172 | ~ 0.1 | 1.7 |
| 2s breath | 250 | ~ 0.1 | 2.5 |
| 5s breath | 491 | ~ 0.2 | 4.6 |
| 10s breath | 507 | ~ 0.2 | 5.1 |

- *Breath onto treated PMMA collection plate.*
- *Calculated average liquid thickness = Volume / Area*

Fig. 8. Photography and evaporation time of EBC on untreated and treated PMMA plate at the plate open configuration (a) 2 s breath on untreated PMMA

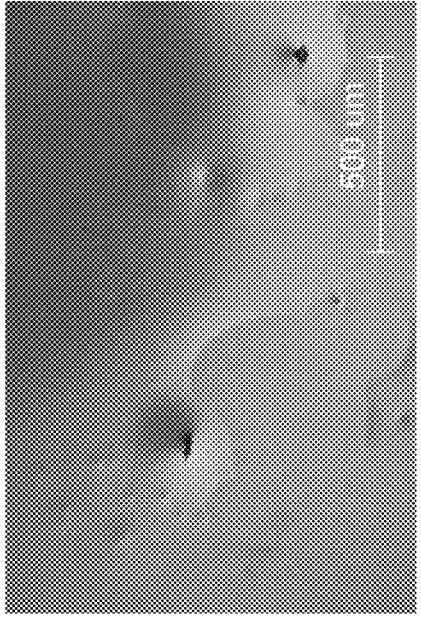

(b) 2 s breath on treated PMMA

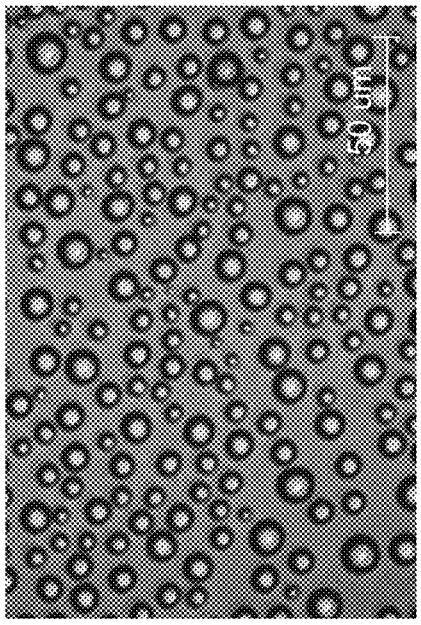

| 2s breath on | Breath Status | Calculated total liquid surface area on 1mm² collecting area (mm²) | Experimental total evaporation time for EBC on 25mm x 25mm PMMA |
|---|---|---|---|
| Untreated PMMA | Droplets | 0.42 | 7 s |
| Treated PMMA | Continuous film | ~ 0.1 | 30 s |

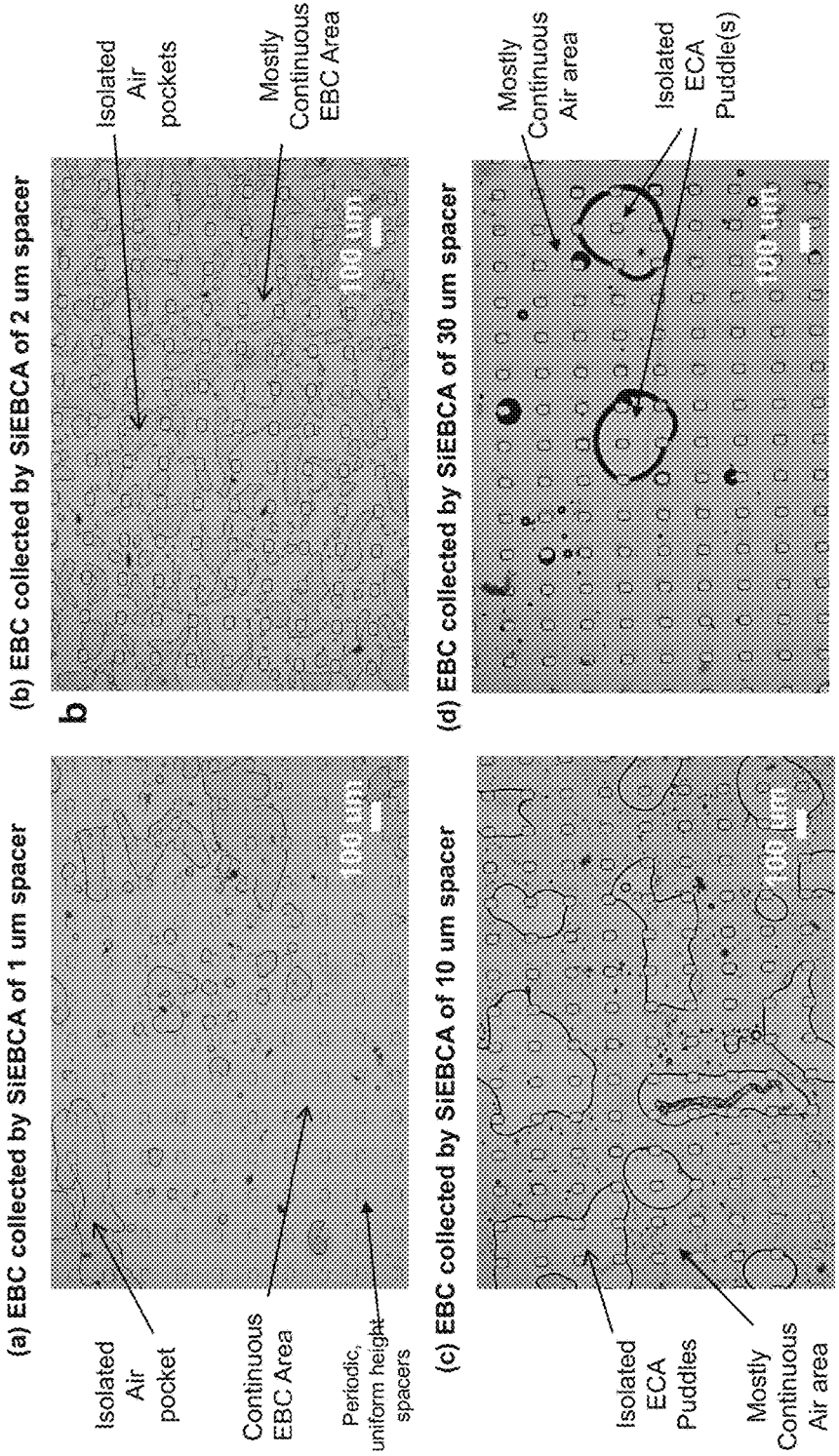

Fig. 10. Experimental Data on EBC collected with SiEBCA of periodic spacers of 1um, 2um, 10um and 30um height, respectively.

- *Breath 2 s on Collection Plate (Glass 25mm x 25mm x 1mm)*
- *X-Plate parameter:*

| Material | Thickness (um) | Pillar Size (W x L) (um) | Inter Pillar Distance (um) | Ratio (IPD/Width) |
|---|---|---|---|---|
| PMMA | 175 | 30 x 38 | 80/82 | 2.7/2.2 |

| | X- Plate | X-Device Performance (measured in 2 cm by 2 cm area) | | | | | |
|---|---|---|---|---|---|---|---|
| | Pillar height | Breath Liquid Status | Liquid Area (mm²) in 25 mm x 25mm collection plate | (Liquid Area) over (Total Area - Spacer Area) | Liquid thickness (um) | Collected Breath liquid volume (uL) | Liquid thickness deviation from pillar height | Liquid thickness uniformity |
| 1 | 1 um | Continuous | 546 | 87% | 1.05 | 0.57 | 5.0% | 4.4% |
| 2 | 2 um | Continuous | 196 | 31% | 2.38 | 0.47 | 19% | 12% |
| 3 | 10 um | Island | 31 | 5% | 13.7 | 0.42 | 37% | 29% |
| 4 | 30 um | Island | 9 | 1% | 45 | 0.41 | 50% | 35% |

1. 1 um gapping X-device can collect most amount of breath liquid with good gapping uniformity.
2. X-device with gapping larger than 1um collect less breath liquid and hard to self-hold well, thus has worse gapping deviation and uniformity.

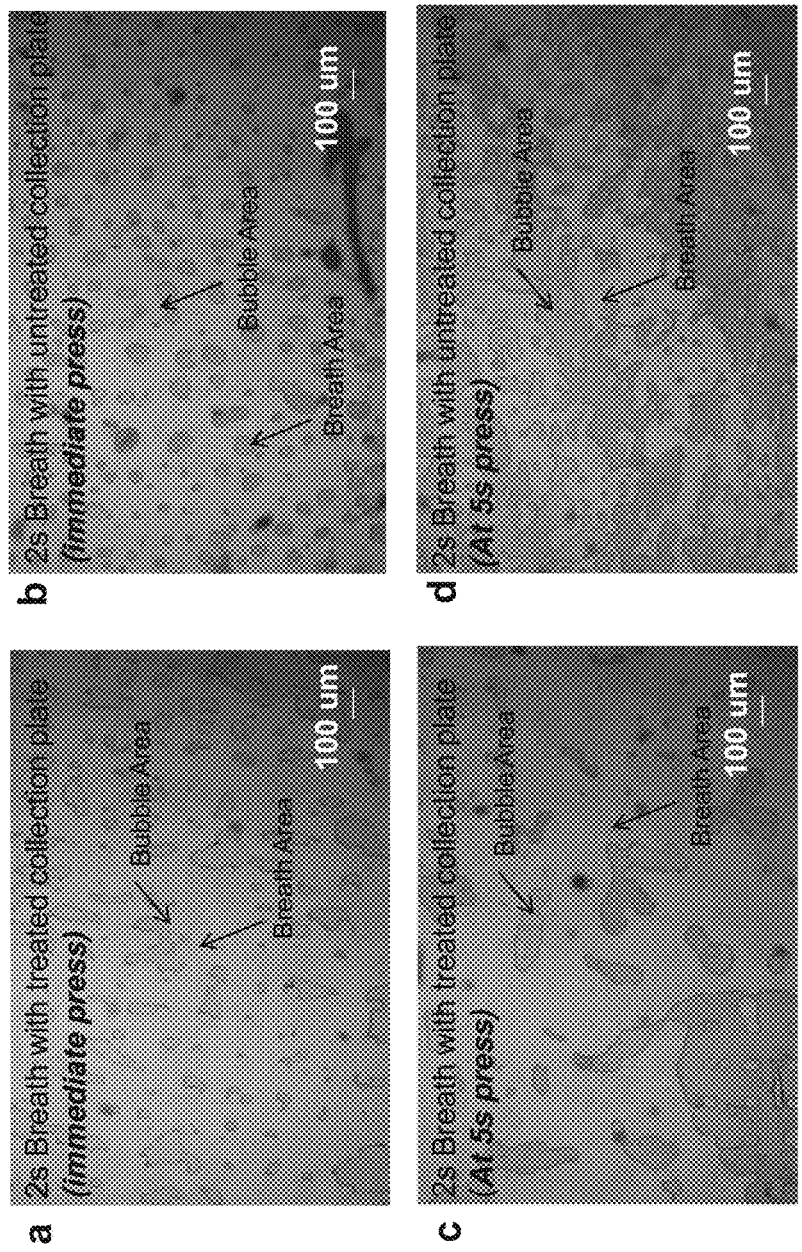
Fig. 11. Photographs of observed breath collection with treated and untreated PMMA collection plates
1. With treated (wetting) PMMA collection plates, more breath liquid can be collected both in "immediate press" and "at 5s press" cases.

Fig. 12. Experimental data on effects of (a) treated and untreated PMMA collection plates and (b) time delay in closing the cover plate on breath collection.

- *Breath 2 s on Collection Plate (PMMA 25mm x 25mm x 1mm)*

*X-Plate parameter:*

| Material | Thickness (um) | Pillar Size (W x L) (um) | Inter Pillar Distance (um) | Pillar Height (um) | Ratio (Width / Height) | Ratio (IPD / Width) |
|---|---|---|---|---|---|---|
| PMMA | 175 | 30 x 38 | 80 / 82 | 1 | 30 / 38 | 2.7 / 2.2 |

| | Collection Plate | | SiEBCA-Device Performance (measured in 2 cm by 2 cm area) | | | | | |
|---|---|---|---|---|---|---|---|---|
| | Surface treatment | Wait time before Press | Liquid Area (mm²) in 25 mm x 25mm collection plate | (Liquid Area) over (Total Area - Spacer Area) | Liquid thickness (um) | Collected Breath liquid volume (uL) | Liquid thickness deviation from pillar height | Liquid thickness uniformity |
| 1 | Treated | Immediate | 405 | 65% | 1.03 | 0.42 | 3.3% | 4.7% |
| 2 | Treated | At 5s | 366 | 59% | 1.07 | 0.39 | 7.4% | 6.4% |
| 3 | Un-treated | Immediate | 370 | 59% | 1.05 | 0.39 | 5.2% | 5.7% |
| 4 | Un-treated | At 5s | 138 | 30% | 1.52 | 0.21 | 52 % | 22% |

1. Compared untreated PMMA collection plate, the treated collection plates (better wetting) collect more breath liquid in both delay times of "immediate press" and "at 5s press".
2. Using the untreated collection plates (less hydrophilic), at 5s delay time for covering, almost a half of the liquid was evaporated.

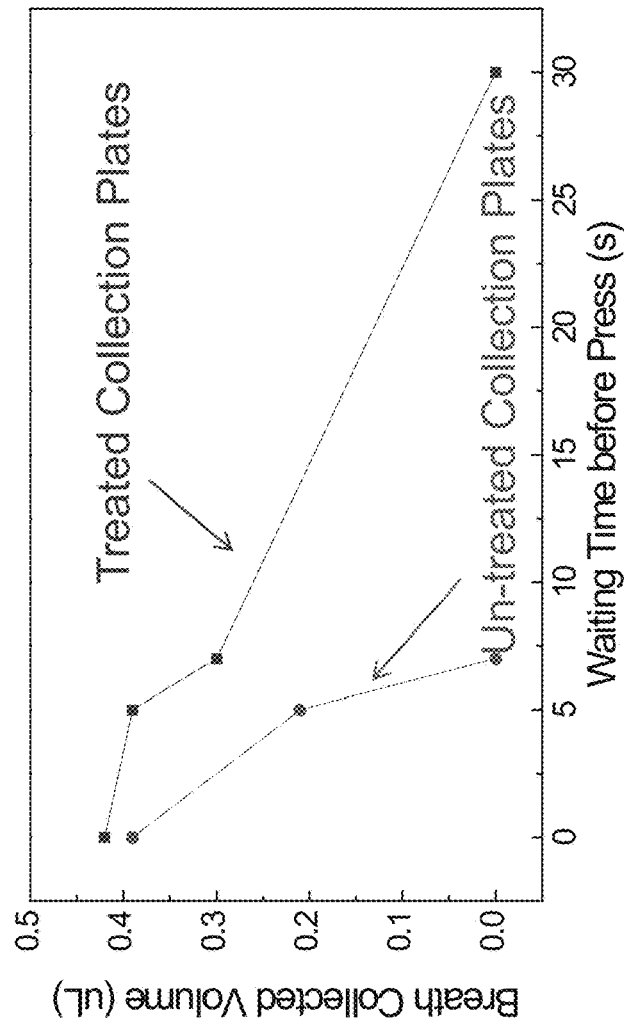
Fig. 13. Collected breath volume vs. time with treated and untreated collection plates (Wait different time before pressing)

Fig. 14 Experiment Data for drying time of EBC collected by SiEBCA and at "Closed configuration"

- Breath 2 s on Collection Plate (PMMA 25 mm x 25 mm x 250 um)
- X-Plate parameter (25 mm x 25 mm x 175 um):

| Material | Thickness (um) | Pillar Size (W x L) (um) | Inter Pillar Distance (um) | Ratio (Width / Height) | Ratio (IPD / Width) |
|---|---|---|---|---|---|
| PMMA | 175 | 30 x 38 | 80 / 82 | 30 / 38 | 2.7 / 2.2 |

Observed drying time of EBC inside SiEBCA

| Collection plate | X-Plate | Drying Time (min) | Average Drying Speed (mm²/min) |
|---|---|---|---|
| Surface treatment | Height (um) | | |
| Treated | 1 | 70 | 8.9 |
| Treated | 10 | 45 | 13.9 |
| Un-treated | 1 | 40 | 15.6 |
| Un-treated | 10 | 10 | 62.5 |

Case 1. Multiplexing. One binding site for one or multiple storage sites
Different storage sites can have the same detection agent but different concentration or different detection agents of the same or different concentration.
a
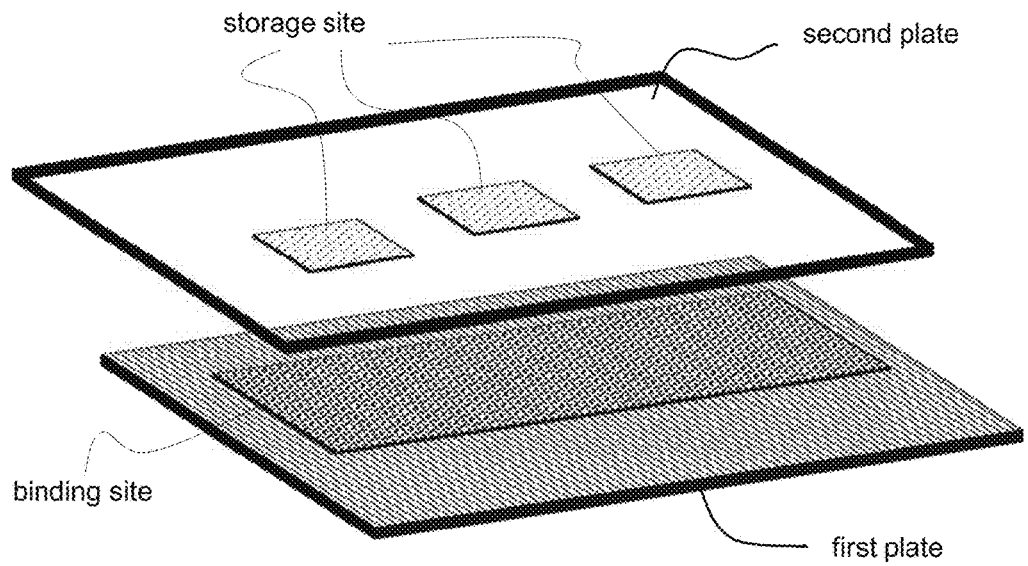
b
Cross-section view
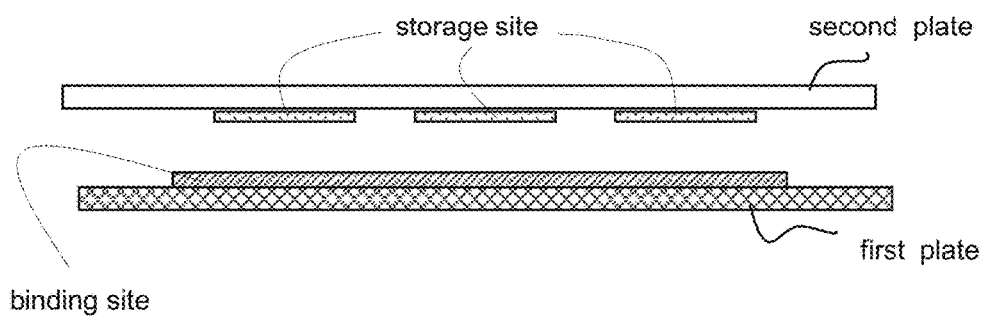
FIG. 16

Case 2. Multiplexing. One storage site for one or multiple binding sites
Different storage sites can have the same detection agent but different concentration or different detection agents of the same or different concentration.
a
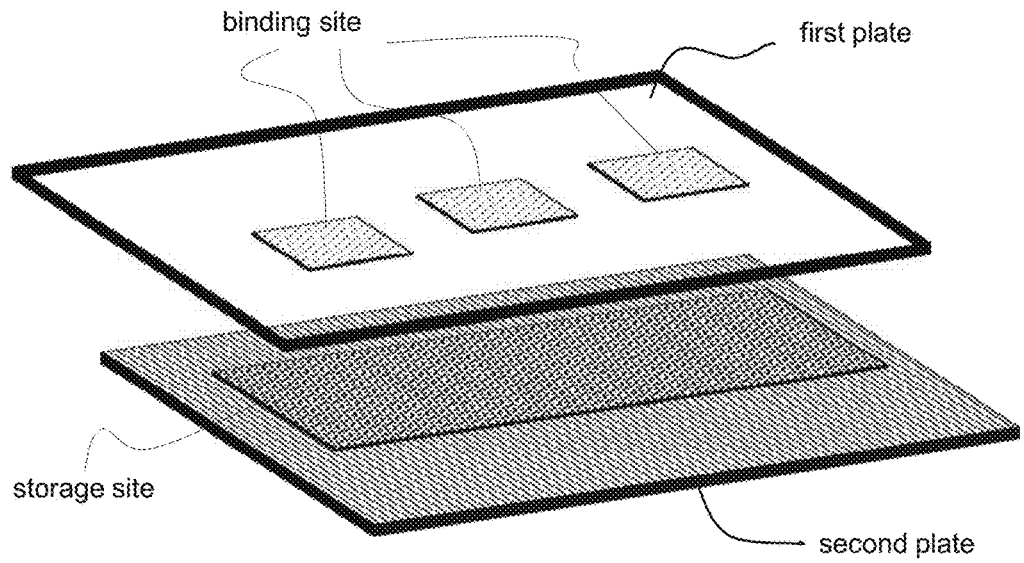
b
Cross-section view
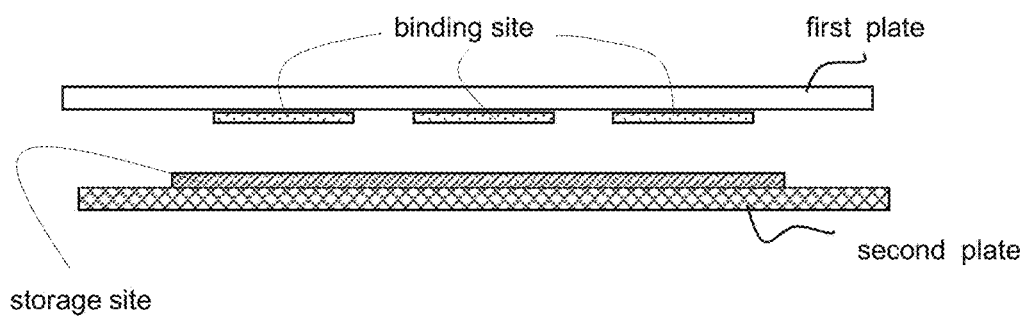
FIG. 17

Case 3. Multiplexing. Multiple binding sites and multiple corresponding storage sites
Different storage sites can have the same detection agent but different concentration or different detection agents of the same or different concentration.
a
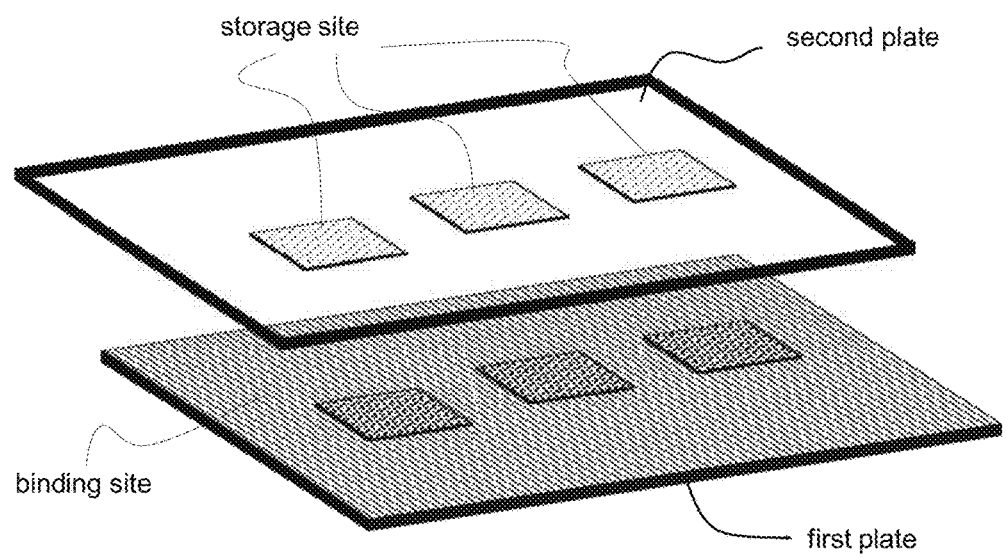
b
Cross-section view
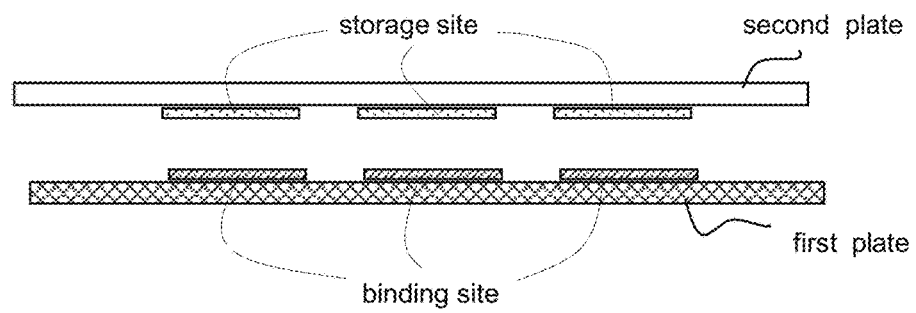
FIG. 18

DEVICE AND SYSTEM FOR COLLECTING AND ANALYZING VAPOR CONDENSATE, PARTICULARLY EXHALED BREATH CONDENSATE, AS WELL AS METHOD OF USING THE SAME

CROSS-REFERENCING

This application is a continuing application of U.S. application Ser. No. 15/561,014 (now issued U.S. Pat. No. 10,132,794), filed Sep. 22, 2017, which claims the benefit of provisional application Ser. Nos. 62/218,455 filed on Sep. 14, 2015, 62/293,188, filed on Feb. 9, 2016, 62/305,123, filed on Mar. 8, 2016, 62/369,181, filed on Jul. 31, 2016 and of PCT application serial no. PCT/US16/46437, filed on Aug. 20, 2016, which PCT application claims the benefit of provisional application Ser. Nos. 62/202,989, filed on Aug. 10, 2015, 62/218,455 filed on Sep. 14, 2015, 62/293,188, filed on Feb. 9, 2016, 62/305,123, filed on Mar. 8, 2016, and 62/369,181, filed on Jul. 31, 2016, all of which applications are incorporated by reference herein in their entireties for all purposes.

FIELD

The present invention is related to the field of bio/chemical sampling, sensing, assays and applications.

BACKGROUND

In bio/chemical vapor condensate sample analysis, particularly exhaled breath condensate (EBC), there is a need for the methods and devices that can simplify the sample collection and measurement processes, that can accelerate the process (e.g. binding, mixing reagents, etc.) and quantify the parameters (e.g. analyte concentration, the sample volume, etc.), that can handle samples with small volume, that allow an entire assay performed in less than a minute, that allow an assay performed by a smartphone (e.g. mobile phone), that allow non-professional to perform an assay her/himself, and that allow a test result to be communicated locally, remotely, or wirelessly to different relevant parties. The present invention relates to the methods, devices, and systems that can address these needs.

SUMMARY OF INVENTION

The following brief summary is not intended to include all features and aspects of the present invention. The present invention is related to the field of bio/chemical sensing, assays and applications. Particularly, the present invention is related to collecting a small amount of a vapor condensate sample (e.g. the exhaled breath condensate (EBC) from a subject of a volume as small as 10 fL (femto-Liter) in a single drop), preventing or significantly reducing an evaporation of the collected vapor condensate sample, analyzing the sample, analyzing the sample by mobile-phone, and performing such collection and analysis by a person without any professionals.

BRIEF DESCRIPTION OF THE DRAWINGS

The skilled artisan will understand that the drawings, described below, are for illustration purposes only. The drawings are not intended to limit the scope of the present teachings in any way. The drawings may not be in scale. In the figures that present experimental data points, the lines that connect the data points are for guiding a viewing of the data only and have no other means.

FIG. 5. The surface wetting properties for an untreated and a treated (for better wetting than untreated surface) surface of a collection plate.

FIG. 6. Methods of pressing the plates of SiEBCA by human hand.

FIG. 7. Experimental data of EBC Droplets sizes and density on the collection plate (untreated PMMA film) at an "open configuration" (e.g. only the collection plate without the cover plate.

FIG. 8. Experimental data of EBC formation on the collection plate which is a surface treated PMMA film) at a plate open configuration.

FIG. 9. Photographs and measured evaporation time (at plate open configuration) of the EBC (2 s breathing directly from a subject) collected on untreated and treated PMMA plate.

FIG. 10. Photographs of spacer height effects (1 µm, 2 µm, 10 µm and 30 µm, respectively) on the EBC collected using SiEBCA at the closed configuration.

FIG. 11. Experimental Data of Photographs of spacer height effects (1 um, 2 um, 10 um and 30 um, respectively) on the EBC collected using SiEBCA at the closed configuration.

FIG. 12. Photographs of the breath collected using the collection plate that are treated and untreated PMMA plates.

FIG. 13. Experimental data on effects of (a) treated and untreated PMMA collection plates and (b) time delay in closing the cover plate on breath collection.

FIG. 14. Experimental data of the volume of the collected breath (i.e. EBC) on the collection plate vs. the time delay (measured from the end of the breath to the covering of the cover plate) for the case of the treated (which is more hydrophilic that the untreated) and untreated collection plate (PMMA) surface, respectively.

FIG. 16 schematically illustrates an exemplary embodiment of the present invention, a multiplexed detection in a single CROF device using one binding site one plate and a plurality of storage sites on the other plate. Panel (a) and (b) is a perspective and a cross-sectional view of an exemplary device, respectively.

FIG. 17 schematically illustrates a further exemplary embodiment of the present invention, a multiplexed detection in a single CROF device using one storage site on one plate and multiple binding sites on the other plate. Panel (a) and (b) is a perspective and a cross-sectional view of an exemplary device, respectively.

FIG. 18 schematically illustrates a further exemplary embodiment of the present invention, a multiplexed detection in a single CROF device with multiple binding sites on one plate and multiple corresponding storage sites on another plate. Panel (a) and (b) is a perspective and a cross-sectional view of an exemplary device, respectively.

DETAILED DESCRIPTION OF EXEMPLARY EMBODIMENTS

Figure 1:
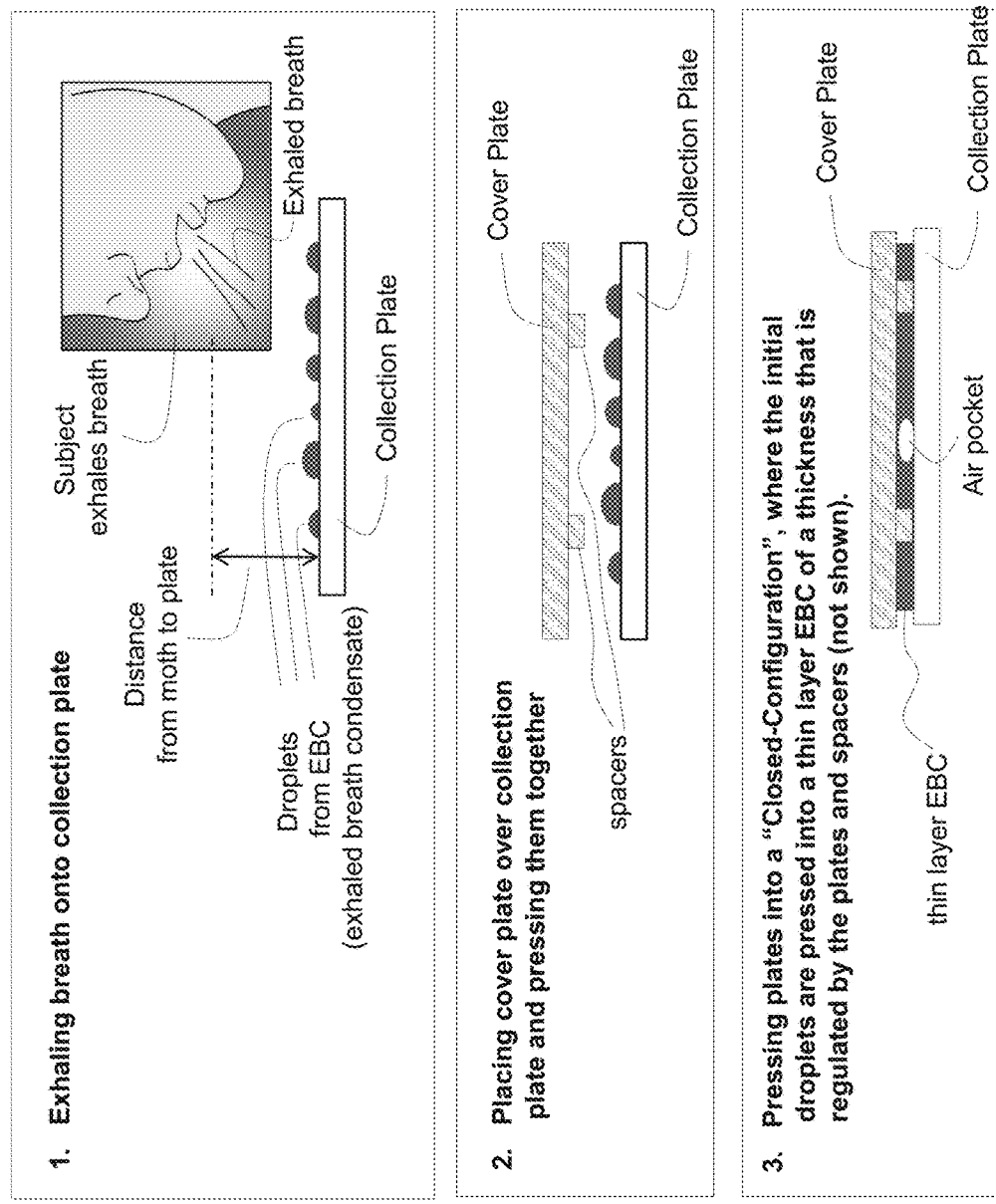
FIG. 1 An illustration of certain aspects of an exemplary device and methods of collecting exhaled breath condensate (EBC) using a SiEBCA (Single-drop EBC Collector/Analyzer).

The following detailed description illustrates some embodiments of the invention by way of example and not by way of limitation. The section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

The present invention is related to the field of bio/chemical sensing, assays and applications. Particularly, the present invention is related to collecting a small amount of a vapor condensate sample (e.g. the exhaled breath condensate (EBC) from a subject of a volume as small as 10 fL (femto-Liter) in a single drop), preventing or significantly reducing an evaporation of the collected vapor condensate sample, analyzing the sample, analyzing the sample by mobile-phone, and performing such collection and analysis by a person without any professionals. Since the exhaled breath condensate (EBC) and other vapor condensate share many common properties, the disclosure uses EBC as a representative to illustrate certain embodiments of the present invention, but such presentation should not be construed as any limitations of the present invention.

Definitions

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The terms "polynucleotide", "nucleotide", "nucleotide sequence", "nucleic acid", "nucleic acid molecule", "nucleic acid sequence" and "oligonucleotide" are used interchangeably, and can also include plurals of each respectively depending on the context in which the terms are utilized.

The term "capture agent" as used herein, refers to a binding member, e.g. nucleic acid molecule, polypeptide molecule, or any other molecule or compound, that can specifically bind to its binding partner, e.g., a second nucleic acid molecule containing nucleotide sequences complementary to a first nucleic acid molecule, an antibody that specifically recognizes an antigen, an antigen specifically recognized by an antibody, a nucleic acid aptamer that can specifically bind to a target molecule, etc.

The term "a secondary capture agent" which can also be referred to as a "detection agent" refers a group of biomolecules or chemical compounds that have highly specific affinity to the antigen. The secondary capture agent can be strongly linked to an optical detectable label, e.g., enzyme, fluorescence label, or can itself be detected by another detection agent that is linked to an optical detectable label through bioconjugation (Hermanson, "Bioconjugate Techniques" Academic Press, 2nd Ed., 2008).

The term "capture agent-reactive group" refers to a moiety of chemical function in a molecule that is reactive with capture agents, i.e., can react with a moiety (e.g., a hydroxyl, sulfhydryl, carboxyl or amine group) in a capture agent to produce a stable strong, e.g., covalent bond.

The terms "specific binding" and "selective binding" refer to the ability of a capture agent to preferentially bind to a particular target analyte that is present in a heterogeneous mixture of different target analytes. A specific or selective binding interaction will discriminate between desirable (e.g., active) and undesirable (e.g., inactive) target analytes in a sample, typically more than about 10 to 100-fold or more (e.g., more than about 1000- or 10,000-fold).

The term "analyte" refers to a molecule (e.g., a protein, peptides, DNA, RNA, nucleic acid, or other molecule), cells, tissues, viruses, and nanoparticles with different shapes.

The term "assaying" refers to testing a sample to detect the presence and/or abundance of an analyte.

As used herein, the terms "determining," "measuring," and "assessing," and "assaying" are used interchangeably and include both quantitative and qualitative determinations.

As used herein, the term "light-emitting label" refers to a label that can emit light when under an external excitation. This can be luminescence. Fluorescent labels (which include dye molecules or quantum dots), and luminescent labels (e.g., electro- or chemi-luminescent labels) are types of light-emitting label. The external excitation is light (photons) for fluorescence, electrical current for electroluminescence and chemical reaction for chemi-luminescence. An external excitation can be a combination of the above.

The phrase "labeled analyte" refers to an analyte that is detectably labeled with a light emitting label such that the analyte can be detected by assessing the presence of the label. A labeled analyte may be labeled directly (i.e., the analyte itself may be directly conjugated to a label, e.g., via a strong bond, e.g., a covalent or non-covalent bond), or a labeled analyte may be labeled indirectly (i.e., the analyte is bound by a secondary capture agent that is directly labeled).

The terms "hybridizing" and "binding", with respect to nucleic acids, are used interchangeably.

The term "capture agent/analyte complex" is a complex that results from the specific binding of a capture agent with an analyte. A capture agent and an analyte for the capture agent will usually specifically bind to each other under "specific binding conditions" or "conditions suitable for specific binding", where such conditions are those conditions (in terms of salt concentration, pH, detergent, protein concentration, temperature, etc.) which allow for binding to occur between capture agents and analytes to bind in solution. Such conditions, particularly with respect to antibodies and their antigens and nucleic acid hybridization are well known in the art (see, e.g., Harlow and Lane (Antibodies: A Laboratory Manual Cold Spring Harbor Laboratory, Cold Spring Harbor, N.Y. (1989) and Ausubel, et al, Short Protocols in Molecular Biology, 5th ed., Wiley & Sons, 2002).

A subject may be any human or non-human animal. A subject may be a person performing the instant method, a patient, a customer in a testing center, etc.

As used herein, a "diagnostic sample" refers to any biological sample that is a bodily byproduct, such as bodily fluids, that has been derived from a subject. The diagnostic sample may be obtained directly from the subject in the form of liquid, or may be derived from the subject by first placing the bodily byproduct in a solution, such as a buffer. Exemplary diagnostic samples include, but are not limited to, saliva, serum, blood, sputum, urine, sweat, lacrima, semen, feces, breath, biopsies, mucus, etc.

As used herein, an "environmental sample" refers to any sample that is obtained from the environment. An environmental sample may include liquid samples from a river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. Typically, samples that are not in liquid form are converted to liquid form before analyzing the sample with the present method.

As used herein, a "foodstuff sample" refers to any sample that is suitable for animal consumption, e.g., human consumption. A foodstuff sample may include raw ingredients, cooked food, plant and animal sources of food, preprocessed food as well as partially or fully processed food, etc. Typically, samples that are not in liquid form are converted to liquid form before analyzing the sample with the present method.

The term "diagnostic," as used herein, refers to the use of a method or an analyte for identifying, predicting the outcome of and/or predicting treatment response of a disease or condition of interest. A diagnosis may include predicting the likelihood of or a predisposition to having a disease or condition, estimating the severity of a disease or condition, determining the risk of progression in a disease or condition, assessing the clinical response to a treatment, and/or predicting the response to treatment.

A "biomarker," as used herein, is any molecule or compound that is found in a sample of interest and that is known to be diagnostic of or associated with the presence of or a predisposition to a disease or condition of interest in the subject from which the sample is derived. Biomarkers include, but are not limited to, polypeptides or a complex thereof (e.g., antigen, antibody), nucleic acids (e.g., DNA, miRNA, mRNA), drug metabolites, lipids, carbohydrates, hormones, vitamins, etc., that are known to be associated with a disease or condition of interest.

A "condition" as used herein with respect to diagnosing a health condition, refers to a physiological state of mind or body that is distinguishable from other physiological states. A health condition may not be diagnosed as a disease in some cases. Exemplary health conditions of interest include, but are not limited to, nutritional health; aging; exposure to environmental toxins, pesticides, herbicides, synthetic hormone analogs; pregnancy; menopause; andropause; sleep; stress; prediabetes; exercise; fatigue; chemical balance; etc.

The term "entity" refers to, but not limited to proteins, peptides, DNA, RNA, nucleic acid, molecules (small or large), cells, tissues, viruses, nanoparticles with different shapes, that would bind to a "binding site". The entity includes the capture agent, detection agent, and blocking agent. The "entity" includes the "analyte", and the two terms are used interchangeably.

The term "binding site" refers to a location on a solid surface that can immobilize an entity in a sample.

The term "entity partners" refers to, but not limited to proteins, peptides, DNA, RNA, nucleic acid, molecules (small or large), cells, tissues, viruses, nanoparticles with different shapes, that are on a "binding site" and would bind to the entity. The entity, include, but not limited to, capture agents, detection agents, secondary detection agents, or "capture agent/analyte complex".

The term "smart phone" or "mobile phone", which are used interchangeably, refers to the type of phones that has a camera and communication hardware and software that can take an image using the camera, manipulate the image taken by the camera, and communicate data to a remote place. In some embodiments, the Smart Phone has a flash light.

The term "average linear dimension" of an area is defined as a length that equals to the area times 4 then divided by the perimeter of the area. For example, the area is a rectangle, that has width w, and length L, then the average of the linear dimension of the rectangle is 4*W*L/(2*(L+W)) (where "*" means multiply and "I" means divide). By this definition, the average line dimension is, respectively, W for a square of a width W, and d for a circle with a diameter d. The area include, but not limited to, the area of a binding site or a storage site.

The term "period" of periodic structure array refers to the distance from the center of a structure to the center of the nearest neighboring identical structure.

The term "storage site" refers to a site of an area on a plate, wherein the site contains reagents to be added into a sample, and the reagents are capable of being dissolving into the sample that is in contract with the reagents and diffusing in the sample.

The term "relevant" means that it is relevant to detection of analytes, quantification and/or control of analyte or entity in a sample or on a plate, or quantification or control of reagent to be added to a sample or a plate.

The term "hydrophilic", "wetting", or "wet" of a surface means that the contact angle of a sample on the surface is less than 90 degree.

The term "hydrophobic", "non-wetting", or "does not wet" of a surface means that the contact angle of a sample on the surface is equal to or larger than 90 degree.

The term "variation" of a quantity refers to the difference between the actual value and the desired value or the average of the quantity. And the term "relative variation" of a quantity refers to the ratio of the variation to the desired value or the average of the quantity. For example, if the desired value of a quantity is Q and the actual value is (Q+p), then the p is the variation and the $\mu/(Q+\mu)$ is the relative variation. The term "relative sample thickness variation" refers to the ratio of the sample thickness variation to the average sample thickness.

The term "optical transparent" refers to a material that allows a transmission of an optical signal, wherein the term "optical signal" refers to, unless specified otherwise, the optical signal that is used to probe a property of the sample, the plate, the spacers, the scale-marks, any structures used, or any combinations of thereof.

The term "none-sample-volume" refers to, at a closed configuration of a CROF process, the volume between the plates that is occupied not by the sample but by other objects that are not the sample. The objects include, but not limited to, spacers, air bubbles, dusts, or any combinations of thereof. Often none-sample-volume(s) is mixed inside the sample.

The term "saturation incubation time" refers to the time needed for the binding between two types of molecules (e.g. capture agents and analytes) to reach an equilibrium. For a surface immobilization assay, the "saturation incubation time" refers the time needed for the binding between the target analyte (entity) in the sample and the binding site on plate surface reaches an equilibrium, namely, the time after which the average number of the target molecules (the entity) captured and immobilized by the binding site is statistically nearly constant.

In some cases, the "analyte" and "binding entity" and "entity" are interchangeable.

The term "first plate" and "collection plate are interchangeable. The term "second plate" and "cover plate" are interchangle.

A "processor," "communication device," "mobile device," refer to computer systems that contain basic electronic elements (including one or more of a memory, input-output interface, central processing unit, instructions, network interface, power source, etc.) to perform computational tasks. The computer system may be a general purpose computer that contains instructions to perform a specific task, or may be a special-purpose computer.

A "site" or "location" as used in describing signal or data communication refers to the local area in which a device or subject resides. A site may refer to a room within a building structure, such as a hospital, or a smaller geographically defined area within a larger geographically defined area. A remote site or remote location, with reference to a first site that is remote from a second site, is a first site that is physically separated from the second site by distance and/or by physical obstruction. The remote site may be a first site that is in a separate room from the second site in a building structure, a first site that is in a different building structure from the second site, a first site that is in a different city from the second site, etc.

As used herein, the term "sample collection site" refers to a location at which a sample may be obtained from a subject. A sample collection site may be, for example, a retailer location (e.g., a chain store, pharmacy, supermarket, or department store), a provider office, a physician's office, a hospital, the subject's home, a military site, an employer site, or other site or combination of sites. As used herein, the term "sample collection site" may also refer to a proprietor or representative of a business, service, or institution located at, or affiliated with, the site.

As used herein, "raw data" includes signals and direct read-outs from sensors, cameras, and other components and instruments which detect or measure properties or characteristics of a sample.

"Process management," as used herein, refers to any number of methods and systems for planning and/or monitoring the performance of a process, such as a sample analysis process One with skill in the art will appreciate that the present invention is not limited in its application to the details of construction, the arrangements of components, category selections, weightings, pre-determined signal limits, or the steps set forth in the description or drawings herein. The invention is capable of other embodiments and of being practiced or being carried out in many different ways.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

Device and System for Collecting and Analyzing Vapor Condensate, Particularly Exhaled Breath Condensate, as Well Method of Using the Same Provided herein is advice for collecting and analyzing vapor condensate (VC) sample, comprising:
a collection plate and a cover plate, wherein:
i. the plates are movable relative to each other into different configurations;
ii. one or both plates are flexible;
iii. each of the plates has, on its respective surface, a sample contact area for contacting a vapor condensate (VC) sample that contains an analyte;
iv. one or both of the plates comprise spacers that are fixed with a respective plate, wherein the spacers have a predetermined substantially uniform height and a pre-determined constant inter-spacer distance and wherein at least one of the spacers is inside the sample contact area;
wherein one of the configurations is an open configuration, in which: the two plates are either completely or partially separated apart, the spacing between the plates is not regulated by the spacers, and the VC sample is deposited on one or both of the plates; and
wherein another of the configurations is a closed configuration which is configured after the VC sample deposition in the open configuration; and in the closed configuration: at least a part of the VC sample is between the two plates and in contact with the two plates, and has a highly uniform thickness that is regulated by the spacers and the two sample surfaces of the plates and is equal to or less than 30 μm with a small variation.

In some embodiments, the device further comprises, on one or both plates, one or a plurality of dry binding sites and/or one or a plurality of reagent sites. In some embodiments, the sample is exhale breath condensate.

In some embodiments, the sample is a vapor from a biological sample, an environmental sample, a chemical sample, or clinical sample. In some embodiments, wherein the analyte comprises a molecule (e.g., a protein, peptides, DNA, RNA, nucleic acid, or other molecules), cells, tissues, viruses, and nanoparticles with different shapes. In some embodiments, wherein the analyte comprises volatile organic compounds (VOCs). In some embodiments, wherein the analyte comprises nitrogen, oxygen, $CO_2$, $H_2O$, and inert gases. In some embodiments, wherein the analyte is stained.

In some embodiments, the device may comprise a dry reagent coated on one or both of the plates. In some embodiments, the dry reagent may bind to an analyte in the blood an immobilize the analyte on a surface on one or both of the plates. In these embodiments, the reagent may be an antibody or other specific binding agent, for example. This dry reagent may have a pre-determined area. In other embodiments, the device may comprise a releasable dry reagent on one or more of the plates, e.g., a labeled reagent such as a cell stain or a labeled detection agent such as an antibody or the like. In some cases, there may be a release time control material on the plate that contains the releasable dry reagent, wherein the release time control material delays the time that the releasable dry regent is released into the blood sample. In some cases, the release time control material delays the time that the dry regent starts is released into the blood sample by at least 3 seconds, e.g., at least 5 seconds or at least 10 seconds. Some embodiments, the drive may contain multiple dry binding sites and/or multiple reagent sites, thereby allowing multiplex assays to be performed. In some cases, the areas occupied by the drying binding sites may oppose the areas occupied by the reagent sites when the plates are in the closed position.

In some embodiments, the regent comprises labeling or staining reagent(s).

In some embodiments, the spacers regulating the layer of uniform thickness (i.e., the spacers that are spacing the plates away from each other in the layer) have a "filling factor" of at least 1%, e.g., at least 2% or at least 5%, wherein the filling factor is the ratio of the spacer area that is in contact with the layer of uniform thickness to the total plate area that is in contact with the layer of uniform thickness. In some embodiments, for spacers regulating the layer of uniform thickness, the Young's modulus of the spacers times the filling factor of the spacers is equal or larger than 10 MPa, e.g., at least 15 MPa or at least 20 MPa, where the filling factor is the ratio of the spacer area that is in contact with the layer of uniform thickness to the total plate area that is in contact with the layer of uniform thickness. In some embodiments, the thickness of the flexible plate times the Young's modulus of the flexible plate is in the range 60 to 750 GPa-$\mu$m, e.g., 100 to 300 GPa-$\mu$m, 300 to 550 GPa-$\mu$m, or 550 to 750 GPa-$\mu$m. In some embodiments, for a flexible plate, the fourth power of the inter-spacer-distance (ISD) divided by the thickness of the flexible plate (h) and the Young's modulus (E) of the flexible plate, $ISD^4/(hE)$, is equal to or less than $10^6$ $\mu m^3/GPa$, e.g., less than $10^5$ $\mu m^3/GPa$, less then $10^4$ $\mu m^3/GPa$ or less than $10^3$ $\mu m^3/GPa$.

In some embodiments, one or both plates comprises a location marker either on a surface of or inside the plate, that provide information of a location of the plate, e.g., a location that is going to be analyzed or a location onto which the blood should be deposited. In some cases, one or both plates may comprise a scale marker, either on a surface of or inside the plate, that provides information of a lateral dimension of a structure of the blood sample and/or the plate. In some embodiments, one or both plates comprises an imaging marker, either on surface of or inside the plate that assists an imaging of the sample. For example, the imaging marker could help focus the imaging device or direct the imaging device to a location on the device. In some embodiments, the spacers can function as a location marker, a scale marker, an imaging marker, or any combination of thereof.

In some embodiments, on one of the sample surface, it further comprises an enclosure-spacer that encloses a partial or entire VC samples deposited on the collection plate.

In some embodiments, the highly uniform thickness has a value equal to or less than 0.5 $\mu$m. In some embodiments, the highly uniform thickness has a value in the range of 0.5 $\mu$m to 1 $\mu$m, 1 $\mu$m to 2 $\mu$m, 2 $\mu$m to 10 $\mu$m, 10 $\mu$m to 20 $\mu$m or 20 $\mu$m to 30 $\mu$m.

In some embodiments, the thickness of the at least a part of VC sample at the closed configuration is larger than the thickness of VC sample deposited on the collection plate at an open configuration.

In some embodiments, the thickness of the at least a part of VC sample at the closed configuration is less than the thickness of VC sample deposited on the collection plate at an open configuration.

In some embodiments, wherein the spacing are fixed on a plate by directly embossing the plate or injection molding of the plate.

In some embodiments, wherein the materials of the plate and the spacers are selected from polystyrene, PMMA, PC, COC, COP, or another plastic.

In some embodiments, the inter-spacer spacing in the range of 1 $\mu$m to 50 $\mu$m, 50 $\mu$m to 100 $\mu$m, 100 $\mu$m to 200 $\mu$m or 200 $\mu$m to 1000 $\mu$m.

In some embodiments, the VC sample is an exhaled breath condensate from a human or an animal.

In some embodiments, the spacers regulating the layer of uniform thickness have a filling factor of at least 1%, wherein the filling factor is the ratio of the spacer area in contact with the layer of uniform thickness to the total plate area in contact with the layer of uniform thickness.

In some embodiments, for spacers regulating the layer of uniform thickness, the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness.

In some embodiments, for a flexible plate, the thickness of the flexible plate times the Young's modulus of the flexible plate is in the range 60 to 750 GPa-$\mu$m.

In some embodiments, for a flexible plate, the fourth power of the inter-spacer-distance (ISD) divided by the thickness of the flexible plate (h) and the Young's modulus (E) of the flexible plate, $ISD^4/(hE)$, is equal to or less than $10^6$ $\mu m^3/GPa$, In some embodiments, one or both plates comprises a location marker, either on a surface of or inside the plate, that provide information of a location of the plate.

In some embodiments, one or both plates comprises a scale marker, either on a surface of or inside the plate, that provide information of a lateral dimension of a structure of the sample and/or the plate.

In some embodiments, one or both plates comprises an imaging marker, either on surface of or inside the plate, that assists an imaging of the sample.

In some embodiments, the spacers functions as a location marker, a scale marker, an imaging marker, or any combination of thereof.

In some embodiments, the average thickness of the layer of uniform thickness is about equal to a minimum dimension of an analyte in the sample.

In some embodiments, the inter-spacer distance is in the range of 1 $\mu$m to 50 $\mu$m, 50 $\mu$m to 120 $\mu$m or 120 $\mu$m to 200 $\mu$m.

In some embodiments, the inter-spacer distance is substantially periodic.

In some embodiments, the spacers are pillars with a cross-sectional shape selected from round, polygonal, circular, square, rectangular, oval, elliptical, or any combination of the same.

In some embodiments, the spacers have are pillar shape and have a substantially flat top surface, wherein, for each spacer, the ratio of the lateral dimension of the spacer to its height is at least 1.

In some embodiments, each spacer has the ratio of the lateral dimension of the spacer to its height is at least 1.

In some embodiments, the minimum lateral dimension of spacer is less than or substantially equal to the minimum dimension of an analyte in the sample.

In some embodiments, the minimum lateral dimension of spacer is in the range of 0.5 μm to 100 μm.

In some embodiments, the minimum lateral dimension of spacer is in the range of 0.5 μm to 10 μm.

In some embodiments, the spacers have a density of at least 100/mm$^2$.

In some embodiments, the spacers have a density of at least 1000/mm$^2$.

In some embodiments, at least one of the plates is transparent.

In some embodiments, at least one of the plates is made from a flexible polymer.

In some embodiments, for a pressure that compresses the plates, the spacers are not compressible and/or, independently, only one of the plates is flexible.

In some embodiments, the flexible plate has a thickness in the range of 10 μm to 200 μm (e.g. about 10 μm, 25 μm, 50 μm, 75 μm, 100 μm, 125 μm, 150 μm, 175 μm).

In some embodiments, the variation is less than 30%, 10%, 5%, 3% or 1%.

In some embodiments, the first and second plates are connected and are configured to be changed from the open configuration to the closed configuration by folding the plates.

In some embodiments, the first and second plates are connected by a hinge and are configured to be changed from the open configuration to the closed configuration by folding the plates along the hinge.

In some embodiments, the first and second plates are connected by a hinge that is a separate material to the plates, and are configured to be changed from the open configuration to the closed configuration by folding the plates along the hinge In some embodiments, the first and second plates are made in a single piece of material and are configured to be changed from the open configuration to the closed configuration by folding the plates.

In some embodiments, the layer of uniform thickness sample is uniform over a lateral area that is at least 100 μm$^2$.

In some embodiments, the layer of uniform thickness sample is uniform over a lateral area that is at least 1 mm$^2$.

In some embodiments, the device is configured to analyze the sample in 60 seconds or less.

In some embodiments, at the closed configuration, the final sample thickness device is configured to analyze the sample in 60 seconds or less.

In some embodiments, the device further comprises, on one or both of the plates, one or a plurality of amplification sites that are each capable of amplifying a signal from the analyte or a label of the analyte when the analyte or label is within 500 nm from an amplification site.

In some embodiments, at the closed configuration, the final sample thickness device is configured to analyze the sample in 10 seconds or less.

In some embodiments, the dry binding site comprises a capture agent.

In some embodiments, the dry binding site comprises an antibody or nucleic acid. In some embodiments, the releasable dry reagent is a labeled reagent. In some embodiments, the releasable dry reagent is a fluorescently-labeled reagent. In some embodiments, the releasable dry reagent is a dye. In some embodiments, the releasable dry reagent is a beads. In some embodiments, the releasable dry reagent is a quantum dot. In some embodiments, the releasable dry reagent is a fluorescently-labeled antibody.

In some embodiments, the first plate further comprises, on its surface, a first predetermined assay site and a second predetermined assay site, wherein the distance between the edges of the assay site is substantially larger than the thickness of the uniform thickness layer when the plates are in the closed position, wherein at least a part of the uniform thickness layer is over the predetermined assay sites, and wherein the sample has one or a plurality of analytes that are capable of diffusing in the sample.

In some embodiments, the first plate has, on its surface, at least three analyte assay sites, and the distance between the edges of any two neighboring assay sites is substantially larger than the thickness of the uniform thickness layer when the plates are in the closed position, wherein at least a part of the uniform thickness layer is over the assay sites, and wherein the sample has one or a plurality of analytes that are capable of diffusing in the sample.

In some embodiments, the first plate has, on its surface, at least two neighboring analyte assay sites that are not separated by a distance that is substantially larger than the thickness of the uniform thickness layer when the plates are in the closed position, wherein at least a part of the uniform thickness layer is over the assay sites, and wherein the sample has one or a plurality of analytes that are capable of diffusing in the sample.

In some embodiments, the releasable dry reagent is a cell stain. In some embodiments, the device further comprises a detector that is an optical detector for detecting an optical signal. In some embodiments, the device further comprises a detector that is an electrical detector for detecting an electric signal.

A system for rapidly analyzing a vapor condensation sample using a mobile phone comprising:
 (a) a device of any prior claim;
 (b) a mobile communication device comprising:
  i. one or a plurality of cameras for the detecting and/or imaging the vapor condensate sample; and
  ii. electronics, signal processors, hardware and software for receiving and/or processing the detected signal and/or the image of the vapor condensate sample and for remote communication.

In some embodiments, the system further comprise a light source from either the mobile communication device or an external source.

In some embodiments, one of the plates has a binding site that binds an analyte, wherein at least part of the uniform sample thickness layer is over the binding site, and is substantially less than the average lateral linear dimension of the binding site.

In some embodiments, further comprising:
 (d) a housing configured to hold the sample and to be mounted to the mobile communication device.

In some embodiments, the housing comprises optics for facilitating the imaging and/or signal processing of the sample by the mobile communication device, and a mount configured to hold the optics on the mobile communication device.

In some embodiments, an element of the optics in the housing is movable relative to the housing.

In some embodiments, the mobile communication device is configured to communicate test results to a medical professional, a medical facility or an insurance company.

In some embodiments, the mobile communication device is further configured to communicate information on the test and the subject with the medical professional, medical facility or insurance company.

In some embodiments, the mobile communication device is further configured to communicate information of the test to a cloud network, and the cloud network process the information to refine the test results.

In some embodiments, the mobile communication device is further configured to communicate information of the test and the subject to a cloud network, the cloud network process the information to refine the test results, and the refined test results will send back the subject.

In some embodiments, the mobile communication device is configured to receive a prescription, diagnosis or a recommendation from a medical professional.

In some embodiments, the mobile communication device is configured with hardware and software to:
 a. capture an image of the sample;
 b. analyze a test location and a control location in in image; and
 c. compare a value obtained from analysis of the test location to a threshold value that characterizes the rapid diagnostic test.

In some embodiments, at least one of the plates comprises a storage site in which assay reagents are stored. In some embodiments, at least one of the cameras reads a signal from the CROF device. In some embodiments, the mobile communication device communicates with the remote location via a wifi or cellular network.

In some embodiments, the mobile communication device is a mobile phone.

A method for rapidly analyzing an analyte in a sample using a mobile phone, comprising:
 a) depositing a sample on the device of any prior system claim;
 b) assaying an analyte in the sample deposited on the device to generate a result; and
 c) communicating the result from the mobile communication device to a location remote from the mobile communication device.

In some embodiments, the analyte comprises a molecule (e.g., a protein, peptides, DNA, RNA, nucleic acid, or other molecule), cells, tissues, viruses, and nanoparticles with different shapes.

In some embodiments, the analyte comprises white blood cell, red blood cell and platelets.

In some embodiments, the method comprises:
 a. analyzing the results at the remote location to provide an analyzed result; and
 b. communicating the analyzed result from the remote location to the mobile communication device.

In some embodiments, the analysis is done by a medical professional at a remote location. In some embodiments, the mobile communication device receives a prescription, diagnosis or a recommendation from a medical professional at a remote location.

In some embodiments, the thickness of the at least a part of VC sample at the closed configuration is larger than the thickness of VC sample deposited on the collection plate at an open configuration.

In some embodiments, the thickness of the at least a part of VC sample at the closed configuration is less than the thickness of VC sample deposited on the collection plate at an open configuration.

In some embodiments, the assaying step comprises detecting an analyte in the sample. In some embodiments, the analyte is a biomarker. In some embodiments, the analyte is a protein, nucleic acid, cell, or metabolite. In some embodiments, the assay done in step (b) is a binding assay or a biochemical assay.

A method for analyzing an analyte in a vapor condensate sample comprising:
 obtaining a device of any prior device claim;
 depositing the vapor condensate sample onto one or both pates of the device;
 placing the plates in a closed configuration and applying an external force over at least part of the plates; and
 analyzing the analyst in the layer of uniform thickness while the plates are the closed configuration.

In some embodiments, wherein the method comprises:
 (a) obtaining a sample;
 (b) obtaining a first and second plates that are movable relative to each other into different configurations, wherein each plate has a sample contact surface that is substantially planar, one or both plates are flexible, and one or both of the plates comprise spacers that are fixed with a respective sample contacting surface, and wherein the spacers have:
  i. a predetermined substantially uniform height,
  ii. a shape of pillar with substantially uniform cross-section and a flat top surface;
  iii. a ratio of the width to the height equal or larger than one;
  iv. a predetermined constant inter-spacer distance that is in the range of 10 µm to 200 µm;
  v. a filling factor of equal to 1% or larger; and
 (c) depositing the sample on one or both of the plates when the plates are configured in an open configuration, wherein the open configuration is a configuration in which the two plates are either partially or completely separated apart and the spacing between the plates is not regulated by the spacers;
 (d), after (c), using the two plates to compress at least part of the sample into a layer of substantially uniform thickness that is confined by the sample contact surfaces of the plates, wherein the uniform thickness of the layer is regulated by the spacers and the plates, and has an average value equal to or less than 30 µm with a variation of less than 10%, wherein the compressing comprises:
  bringing the two plates together; and
  conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and
 (e) analyzing the in the layer of uniform thickness while the plates are the closed configuration;
 wherein the filling factor is the ratio of the spacer contact area to the total plate area;
 wherein a conformable pressing is a method that makes the pressure applied over an area is substantially constant regardless the shape variation of the outer surfaces of the plates; and
 wherein the parallel pressing applies the pressures on the intended area at the same time, and a sequential pressing applies the pressure on a part of the intended area and gradually move to other area.

In some embodiments, wherein the method comprises
removing the external force after the plates are in the closed configuration; and
imaging the analytes in the layer of uniform thickness while the plates are the closed configuration; and
counting a number of analytes or the labels in an area of the image.

In some embodiments, wherein the method comprises
removing the external force after the plates are in the closed configuration; and
measuring optical signal in the layer of uniform thickness while the plates are the closed configuration.

In some embodiments, the inter-spacer distance is in the range of 20 µm to 200 µm. In some embodiments, the inter-spacer distance is in the range of 5 µm to 20 µm.

In some embodiments, a product of the filling factor and the Young's modulus of the spacer is 2 MPa or larger.

In some embodiments, the surface variation is less than 50 nm.

In some embodiments, the method further comprising a step of calculating the concentration of an analyte in the relevant volume of sample, wherein the calculation is based on the relevant sample volume defined by the predetermined area of the storage site, the uniform sample thickness at the closed configuration, and the amount of target entity detected.

In some embodiments, the analyzing step comprise counting the analyte in the sample.

In some embodiments, the imaging and counting is done by:
i. illuminating the cells in the layer of uniform thickness;
ii. taking one or more images of the cells using a CCD or CMOS sensor;
iii. identifying cells in the image using a computer; and
iv. counting a number of cells in an area of the image.

In some embodiments, the external force is provided by human hand. In some embodiments, the method future comprises a dry reagent coated on one or both plates.

In some embodiments, the layer of uniform thickness sample has a thickness uniformity of up to +/−5%.

In some embodiments, the spacers are pillars with a cross-sectional shape selected from round, polygonal, circular, square, rectangular, oval, elliptical, or any combination of the same.

In some embodiments, the spacing between the spacers is approximately the minimum dimension of an analyte.

The method of any prior claim, wherein one or both plate sample contact surfaces comprises one or a plurality of amplification sites that are each capable of amplifying a signal from the analyte or a label of the analyte when the analyte or label is within 500 nm from an amplification site.

In some embodiments, the sample is exhale breath condensate. In some embodiments, the sample is a vapor from a biological sample, an environmental sample, a chemical sample, or clinical sample. In some embodiments, the analyte comprises a molecule (e.g., a protein, peptides, DNA, RNA, nucleic acid, or other molecules), cells, tissues, viruses, and nanoparticles with different shapes In some embodiments, the analyte comprises volatile organic compounds (VOCs). In some embodiments, the analyte comprises nitrogen, oxygen, CO2, H2O, and inert gases. In some embodiments, the analyte is stained.

In some embodiments, on one of the sample surface, it further comprises an enclosure-spacer that encloses a partial or entire VC samples deposited on the collection plate. In some embodiments, the highly uniform thickness has a value equal to or less than 0.5 µm. In some embodiments, the highly uniform thickness has a value in the range of 0.5 µm to 1 µm. In some embodiments, the highly uniform thickness has a value in the range of 1 µm to 2 µm. In some embodiments, the highly uniform thickness has a value in the range of 2 µm to 10 µm. In some embodiments, the highly uniform thickness has a value in the range of 10 µm to 20 µm. In some embodiments, the highly uniform thickness has a value in the range of 20 µm to 30 µm.

In some embodiments, on one of the sample surface, it further comprises an enclosure-spacer that encloses a partial or entire VC samples deposited on the collection plate.

Embodiment (EBC)-1. SiEBCA (Single-Drop Exhaled Breath Condensate Collector and Analyzer)

Exhaled breath condensate (EBC) analysis is a noninvasive method of detecting biomarkers, mainly coming from the lower respiratory tract. EBC is collected during quiet breathing, as a product of cooling and condensation of the exhaled aerosol.

Figure 2:
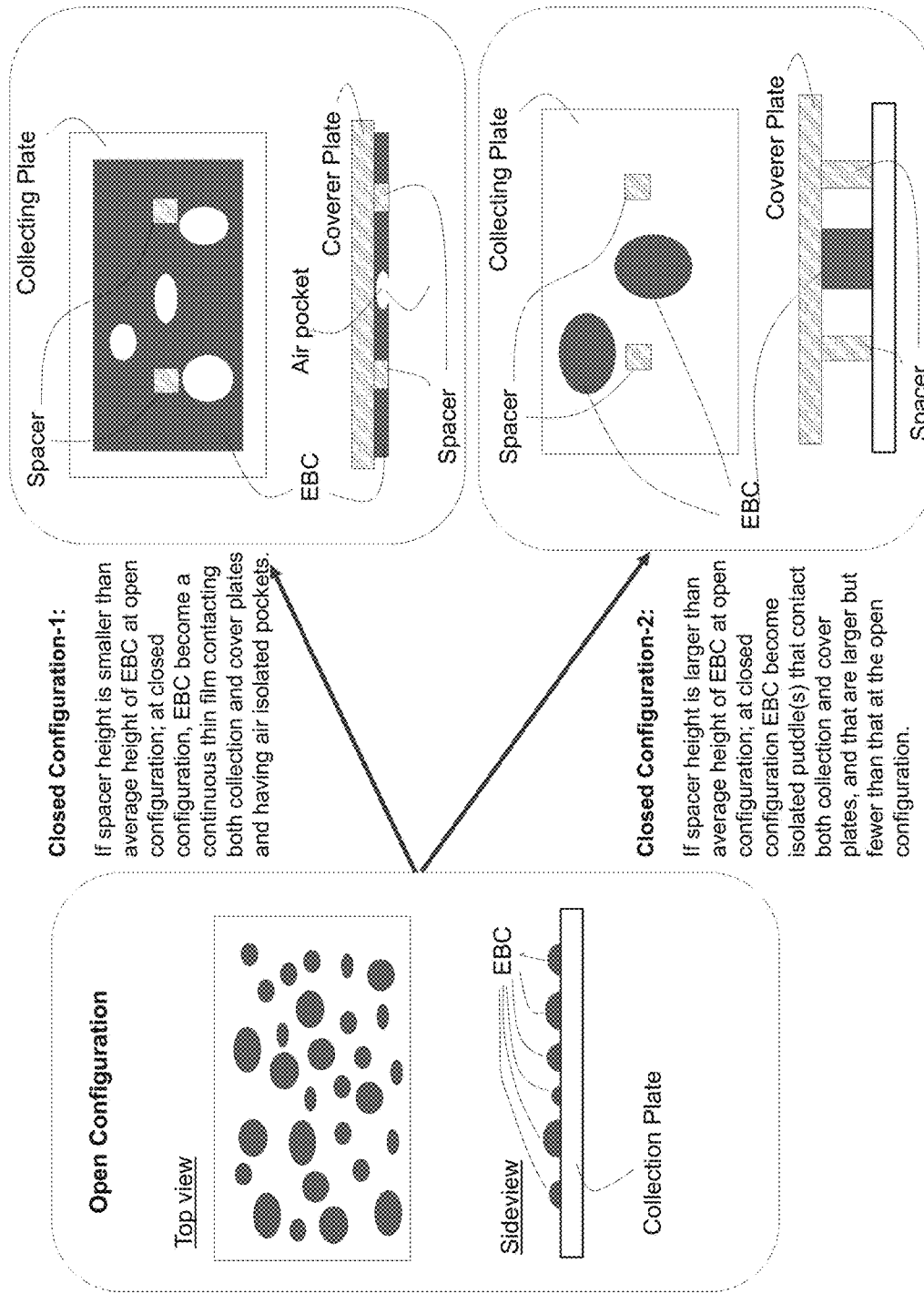
FIG. 2 An illustration of different formations of EBC at closed configuration of SiEBCA depends on spacer height. In closed configureation-1: If spacer height is smaller than average height of EBC at open configuration; at closed configuration, EBC become a continuous thin film contacting both collection and cover plates and may have air isolated pockets. In the closed condiguraiton-2: If spacer height is larger than average height of EBC at open configuration; at closed configuration EBC become isolated puddle(s) that contact both collection and cover plates, and that are larger but fewer than that at the open configuration.
Figure 3:
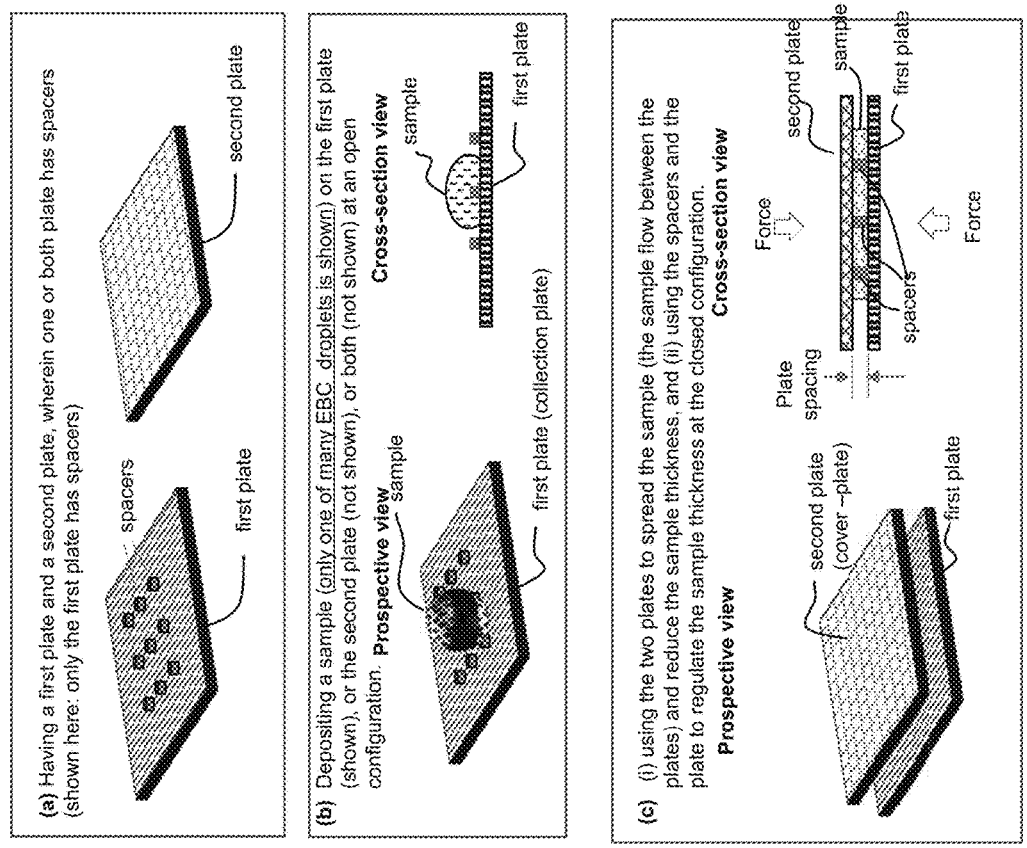
FIG. 3. An illustration of an embodiment of the devices and the methods of a SiEBCA (Single-drop EBC Collector/Analyzer).

An exemplary method of collecting exhaled breath condensate (EBC) using a SiEBCA (Single-drop EBC Collector/Analyzer), as illustrated in FIG. 1, comprises the basic steps:

(1) exhaling breath onto the collection plate (FIG. 1-1). A subject (e.g. human) breathe onto a plate, termed "collection plate", and the breath condenses into EBC, which are in droplets with different sizes, depending on the breathing time. For a short breathing time most droplets are separated from each other. The surface of the collection plate that collects the EBC is termed the sample surface;

(2) placing a cover plate over the collection plate and pressing them together (FIG. 1-2). A cover plate with spacers (which are used for regulating the spacing between the cover plate and the substrate plate) is placed on top of the sample surface; and (3) pressing plates into a "Closed-Configuration (FIG. 1-3). The cover plate and the substrate are compressed together with at least a part of the EBC between the plates.

In the method of FIG. 1, the initial droplets are pressed into a thin layer EBC of a thickness that is regulated by the plates and spacers (not shown).

One reason for using the wording of "single drop" in SiEBCA is that in principle, the SiEBCA can detect and analyze a single drop of EBC deposited on the plate.

In the description of the present invention, "the substrate plate" and "the cover plate" are respectively interchangeable with "the first plate" and "the second plate".

In some embodiments, the plates are cooled to reduce the evaporation of collected EBC.

A1 A method of collecting EBC, as a basic embodiment of the present invention for collecting EBC from a subject, as illustrated in FIG. 1, comprises the steps:

(a) obtaining a collection plate and a cover plate that are movable relative to each other into different configurations, wherein one or both of the plates comprise spacers (not shown in FIG. 1 but in FIG. 2) that are fixed with the respective plate, and have a predetermined average height of 100 µm or less;

(b) depositing, when the plates are configured in an open configuration, an EBC sample by exhaling breath from a subject toward the collection plate, wherein:
(i) the exhaled breath condensates on a collection surface of the collection plate to form droplets and/or puddles that have different lateral sizes and different heights, depending upon the surface wetting properties of the collection surface; and (ii) the open configuration is a configuration in which the two plates are either partially or completely separated apart and the spacing between the plates is not regulated by the spacers; and (c) after (b), bringing the cover plate over the collection surface of the collection plate and then bringing the two plates into a closed configuration by pressing the plates, wherein:

(i) the closed configuration is a configuration, in which: at least a part of the spacers are between the cover plate and the collection plate, and a relevant area of the collection surface of the collection plate is covered by the cove plate and has a plate spacing that is regulated by the spacers; and (ii) at the closed configuration, in the relevant area, substantial number or all of the droplets or puddles formed in step (b) at the open configuration merge-merge into puddle(s) that (1) have much larger lateral size but in a smaller number than the open configuration and (2) touch both inner surfaces of the cover plate and the collection plate, thereby the thickness of the puddle(s) is confined by the inner surfaces of the plates and equal to the spacing between the inner surfaces, and the total surface area of the deposited EBC exposed to the ambient is significantly reduced;

wherein the plate spacing is the spacing between the two inner surfaces (the two surfaces facing each other) of the cover plate and the collection plate, the relevant area is a portion or entire surface of the collection surface, and the collection surface is a portion or entire surface of the collection plate.

From our experiments (described in details in Examples), we found that the final form of the EBC collected by SiEBCA when the plates are in the closed configuration depends upon the spacer height. Experimentally (see FIG. 13), we found, as illustrated in FIG. 2, that:

(1) At the closed configuration of the SiEBCA, if the spacing between the inner surfaces of the plates is less than the average height of the EBC droplets or puddles at the open configuration, the EBC droplets or puddles are compressed by the collection plate and the cover plate into a continuous film of a thickness thinner than at the open configuration, and also air pockets may exist in the film; and (2) otherwise (i.e. if the spacing is equal to or larger than that the average height at the open configuration) the droplets and/or puddles self-emerged into discrete puddles that are fewer in number but larger in lateral size (area) than that in the open configuration, touch both sample contact (inner) surfaces of the cover plate and the collection plate, and have the thickness confined by the inner surfaces of the plates and equal to the spacing between the inner surfaces. In this case, the EBC sample thickness at the closed configuration is equal to or larger than the EBC sample average thickness at the open configuration. The increase in the EBC puddle thickness at the closed configuration, as we observed experimentally, are due to the interactions between the plates and the EBC sample.

EBC-1.2. Device for EBC Collection

FIG. 3. is an illustration of an embodiment of the devices and the methods of a SiEBCA (Single-drop EBC Collector/Analyzer): (a) having a first plate and a second plate, wherein one or both plate has spacers (shown here: only the first plate has spacers); (b) depositing a sample (only one of many EBC droplets is shown) on the first plate (shown), or the second plate (not shown), or both (not shown) at an open configuration; and (c) (i) using the two plates to spread the sample (the sample flow between the plates) and reduce the sample thickness, and (ii) using the spacers and the plate to regulate the sample thickness at the closed configuration.

A2 A device of collecting EBC, as a basic embodiment of the present invention for collecting EBC sample from a subject, as illustrated in FIG. 1, comprises:

i. a first plate and a second plate, wherein the plates are movable relative to each other into different configurations, and one or both plates are flexible;

ii. a sample contact area on the respective surface of each of the plates for contacting EBC sample, iii. spacers on one or both of the plates, wherein the spacers are fixed with a respective plate, have a predetermined substantially uniform height of 30 μm or less and a predetermined constant inter-spacer distance that is 250 μm or less, and wherein at least one of the spacers is inside the sample contact area;

wherein one of the configurations is an open configuration, in which: the two plates are separated apart, the spacing between the plates is not regulated by the spacers, and the EBC sample is deposited on one or both of the plates from a subject; and wherein another of the configurations is a closed configuration which is configured after the EBC sample deposition in the open configuration; and in the closed configuration: at least part of the EBC sample is compressed by the two plates into a layer of highly uniform thickness, wherein the uniform thickness of the layer is in contact with and confined by the inner surfaces of the two plates and is regulated by the plates and the spacers.

In some embodiments of paragraphs A1 and A2, the deposition of the EBC sample is by directly exhaling from a subject to one of the plates.

In some embodiments of paragraphs A1 and A2, the deposition of the EBC sample is by directly exhaling from a subject to both of the plates.

"Covering time delay" means a time period that it takes from the step (b) EBC deposition of paragraph A1 to the end of the step (c) of paragraph A1 that brings the cover plate and the collection plate to a closed configuration.

In the method of paragraph A1, the covering time delay should be as short as possible to reduce the evaporation of deposited EBC. In one preferred embodiment, the covering time delay is equal to or less than 2 sec. In another preferred embodiment, the covering time delay is equal to or less than 5 sec. In another preferred embodiment, the covering time delay is equal to or less than 10 sec. In another preferred embodiment, the covering time delay is equal to or less than 30 sec. And In another preferred embodiment, the covering time delay is in the range of 30 sec to 300 sec (e.g. 30 to 60 sec, 60 sec to 120 sec, or 120 sec to 300 sec).

EBC-1.3. Significant Reduction of EBC Evaporation Rate.

One key advantage of the method and device of paragraph A1 and A2 is that, compared to the open configuration of the collection plate and the cover plate, the closed configuration of the plates significantly reduces the surface area of the EBC exposed to the ambient, and hence significantly reduces the EBC sample evaporation rate and significantly increases the time that EBC sample is in liquid form (i.e. the time that EBC sample is not completely evaporated). For example, we have observed that the drying time (the time it takes for the EBC sample to dry out completely) increased from 30 secs at an open configuration to 70 mins, a factor of 140 times longer.

EBC-1.4. Guard Ring (Enclosed Spacers).

To further reduce the EBC sample evaporation rate, the enclosed spacers or the guard rings can be used to surround the sample to seal off the sample from the ambient. The guard ring can circle an area that is the same as, or larger or smaller than the EBC sample deposited at the open configuration. The guard ring can be configured to further divide an EBC sample into multiple chambers (FIG. 4.).

Figure 4:
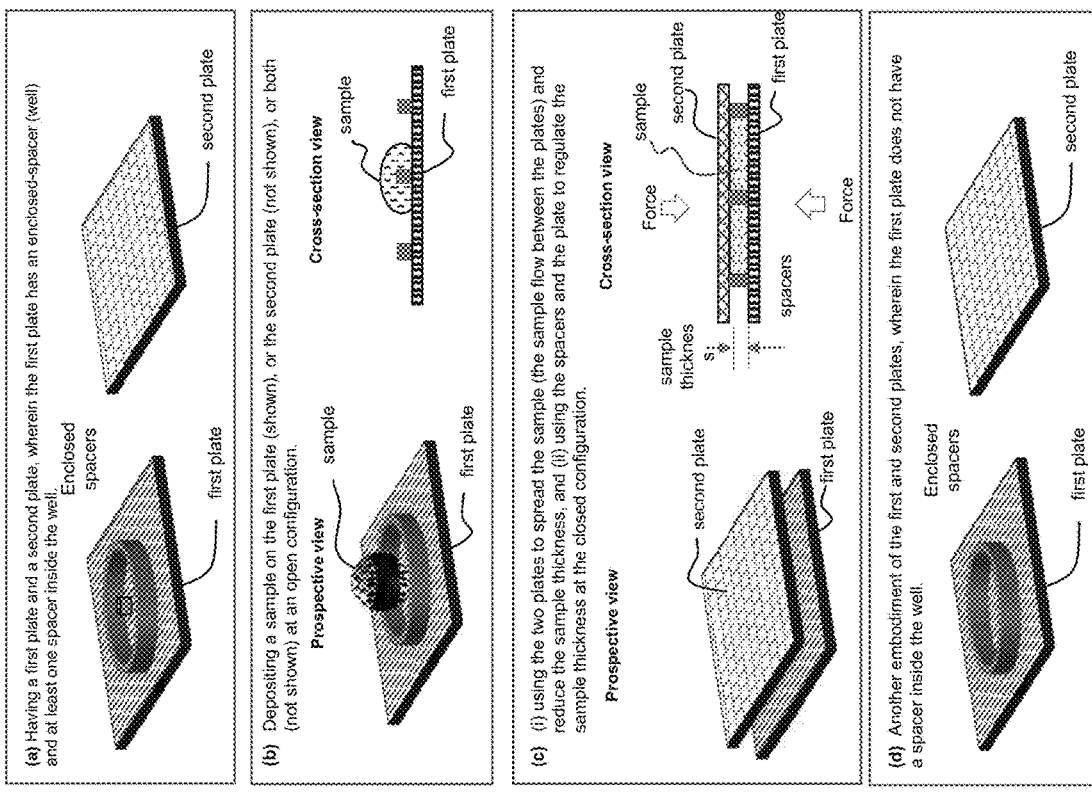
FIG. 4. An illustration of a SiEBCA with both "open spacer" and "enclosed spacer", where the open spacer is a post (pillar) while the enclosed spacer is a ring spacer (d) and a four chamber grid spacer (e).
Figure 15:
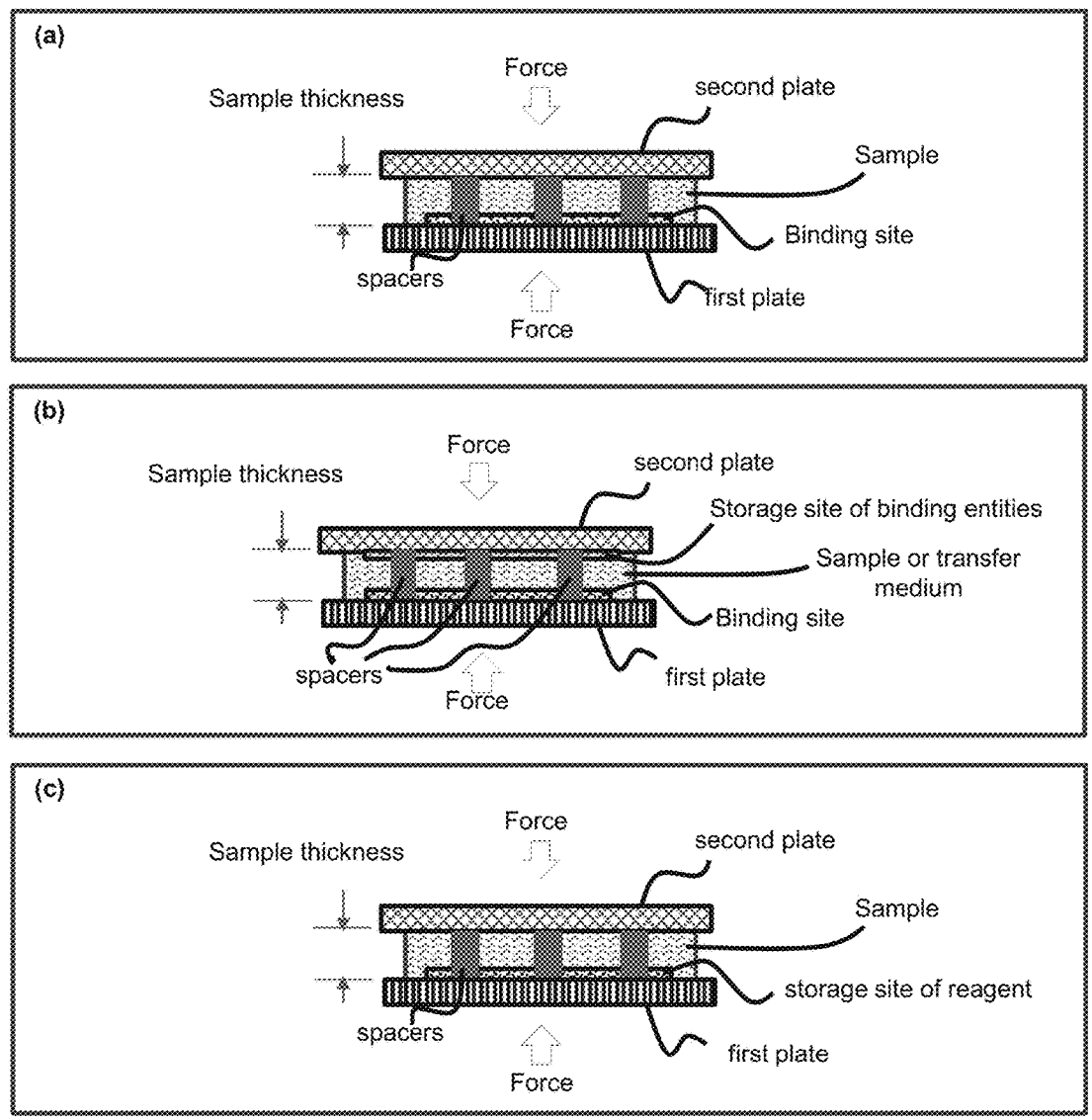
FIG. 15 shows reducing binding or mixing time by reducing the sample thickness using two pates, spacers, and compression (shown in cross-section). Panel (a) illustrates reducing the time for binding entities in a sample to a binding site on a solid surface (X-(Volume to Surface)). Panel (b) illustrates reducing the time for binding entities (e.g. reagent) stored on a surface of plate to a binding site on a surface of another surface (X-(Surface to Surface)). Panel (c) illustrates reducing the time for adding reagents stored on a surface of a plate into a sample that is sandwiched between the plate and other plate (X-(Surface to Volume)).

FIG. 4. is an illustration of a SiEBCA with both "open spacer" and enclosed spacer, where the open spacer is a post (pillar) while the enclosed spacer is a ring. The enclosed spacer reduces the evaporation of the EBC collected inside the enclosed spacer, since at the closed configuration, the enclosed spacer, the cover plate and the collection plate form an enclosed chamber. If there are only the open spacers but not an enclosed spacer, at the plate closed configuration, the collected EBC still evaporates from the edge of the film formed by the EBC, although such evaporation is much slower than that without a cover plate.

In the method and the device of paragraph A1 and A2, the spacers can be an open spacer(s), an enclosed spacer(s), or a combination of thereof.

Details of the devices and methods to keep the EBC thickness uniform are given in the other part of the disclosure.

EBC-2. EBC Analysis

Another significant advantage of the present invention is that the method and the device of paragraph A1-2 can be used for as an EBC analyzer by itself or by certain modifications. The EBC analyzer analyze one or a plurality of target analytes in the EBC. The target analytes are further discussed in Section 3, . . . .

The modifications made to the method and device of paragraphs 1-2 include, but not limited to, the following, which can used alone (individually) or in combinations:

(1) Binding Sites. One or both of the plates have one or plurality of binding site . . . . Each (type) of the regents are in either in well separated locations (the well separation will be defined later).

(2) Storage sites. One or both of the plates have one or plurality of binding site . . . . Each (type) of the regents are in either in well separated locations (the well separation will be defined later).

(3) Amplification site.

(4) Muiltplexing of analyte detections.

More details of the binding sites, storage sites, amplification sites, and multuplixing sites, as well as their usage for VC and EBC analysis are given in the other part of the disclosure.

A-3 A method of analyzing EBC from a subject for analyzing EBC of a subject comprising:

(a) obtaining a collection plate and a cover plate that are movable relative to each other into different configurations, wherein one or both of the plates comprise spacers (not shown in FIG. 1 but in FIG. 2) that are fixed with the respective plate, and have a predetermined average height of 100 μm or less;

(b) depositing, when the plates are configured in an open configuration, an EBC sample by exhaling breath from a subject toward the collection plate, wherein:

(i) the exhaled breath condensates on a collection surface of the collection plate to form droplets and/or puddles that have different lateral sizes and different heights, depending upon the surface wetting properties of the collection surface; and (ii) the open configuration is a configuration in which the two plates are either partially or completely separated apart and the spacing between the plates is not regulated by the spacers;

(c) after (b), bringing the cover plate over the collection surface of the collection plate and then bringing the two plates into a closed configuration by pressing the plates, wherein:

(i) the closed configuration is a configuration, in which: at least a part of the spacers are between the cover plate and the collection plate, and a relevant area of the collection surface of the collection plate is covered by the cove plate and has a plate spacing that is regulated by the spacers; and (ii) at the closed configuration, in the relevant area, substantial number or all of the droplets or puddles formed in step (b) at the open configuration merge into puddle(s) that (1) have much larger lateral size but in a smaller number than the open configuration and (2) touch both inner surfaces of the cover plate and the collection plate, thereby the thickness of the puddle(s) is confined by the inner surfaces of the plates and equal to the spacing between the inner surfaces, and the total surface area of the deposited EBC exposed to the ambient is significantly reduced; and (d) analyzing the EBC, wherein the plate spacing is the spacing between the two inner surfaces (the two surfaces face each other) of the cover plate and the collection plate, the relevant area is a portion or entire surface of the collection surface, and the collection surface is a portion or entire surface of the collection plate.

The collection plate generally is held at a temperature the same as the ambient, but in some embodiments, the temperatures can be different from the ambient, either higher or lower depending upon the goal of the collection. For example, a temperature lower than the ambient may be used for reducing the EBC evaporation; and a temperature higher than the ambient many bused for evaporating more than that at the ambient temperature is needed.

EBC-3. Applications

EBC analysis can be used for detection of inflammatory markers, which reflect the state of chronic airways diseases such as chronic obstructive pulmonary disease (COPD), asthma, and cystic fibrosis (CF). EBC analysis can also be used for identification of metabolic, proteomic, and genomic fingerprints of breathing, aiming for an early diagnosis of not only respiratory, but also systemic diseases.

EBC-3.1. Analysis of EBC

Breath tests are among the least invasive methods available for clinical diagnosis, disease state monitoring, health monitoring and environmental exposure assessment.

A breath matrix from a subject is a mixture of nitrogen, oxygen, $CO_2$, $H_2O$, and inert gases. The remaining small fraction consists of more than 1000 trace volatile organic compounds (VOCs) with concentrations in the range of parts per million (ppm) to parts per trillion (ppt) by volume. In terms of their origin, these volatile substances may be generated in the body (endogenous) or may be absorbed as contaminants from the environment (exogenous). The composition of VOCs in breath varies widely from person to person, both qualitatively and quantitatively.

Although the number of VOCs found to date in human breath is more than 1000, only a few VOCs are common to all humans. These common VOCs, which include isoprene, acetone, ethane, and methanol, are products of core metabolic processes and are very informative for clinical diagnostics. The bulk matrix and trace VOCs in breath exchange between the blood and alveolar air at the blood-gas interface in the lung. One exception is NO, which is released into the airway in the case of airway inflammation.

The endogenous compounds found in human breath, such as inorganic gases (e.g., NO and CO), VOCs (e.g., isoprene, ethane, pentane, acetone), and other typically nonvolatile substances such as isoprostanes, peroxynitrite, or cytokines, can be measured in breath condensate. Testing for endogenous compounds can provide valuable information concerning a possible disease state. Furthermore, exogenous molecules, particularly halogenated organic compounds, can indicate recent exposure to drugs or environmental pollutants.

Volatile Organic Compounds (VOCs) are organic substances that have a high vapor pressure and therefore evaporate at room temperature. The VOCs that may be assayed as target analytes by the methods and devices provided by the present invention include, but not limited to, biologically generated VOCs (e.g., terpenes, isoprene, methane, green leaf volatiles) and anthropogenic VOCs (e.g., typical solvents used in paints and coatings, like ethyl acetate, glycol ethers, and acetone, vapors from adhesives, paints, adhesive removers, building materials, etc., like methylene chloride, MTBE, and formaldehyde, chlorofurocarbons and perchloroethylene used in dry cleaning, vapor and exhaustive gas from fossil fuels, like benzene and carbon monoxide). Detailed discussions on certain biomarkers is given in Table 1.

TABLE 1

Breath markers in certain diseases or applications.

| | Disease or application | Breath marker |
|---|---|---|
| Oxidative stress | Lipid peroxidation | Pentane, ethane |
| | Asthma, COPD, bronchiectasis, ARDS | $H_2O_2$ breath methylated alkane contour |
| Lung diseases | Asthma | NO, CO, $H_2O_2$, isoprostanes, nitrite/nitrate |
| | COPD | NO, $H_2O_2$, eicosanoids (leukotrienes, prostanoids, isoprostanes), isoprostanes |
| | Cystic fibrosis | NO, CO, $H_2O_2$, isoprostanes, nitrite/nitrate |
| | Pulmonary allograft dysfunction | NO |
| | Lung cancer | NO |
| | Lung transplant recipient with acute rejection | Exhaled carbonyl sulfide |
| Metabolic diseases | Diabetes | Acetone |
| Gastroenteric diseases | Disorders of digestion and absorption (lactase deficiency, disorders of di- and monosaccharide malabsorption, starch malabsorption, and small-bowel bacterial overgrowth) | $H_2$ |
| | Gastritis, duodenal ulcer, gastric ulcer, and gastric cancer | Isotopes of carbon ($^{13}C$ or $^{14}C$) |
| Assessment of exposure to VOCs | | Vinyl chloride and cis-1,2-dichloroethene, chloroform and bromodichloromethane, trichloroethene |
| Other applications | Respiratory monitoring | $CO_2/O_2$ ratio |
| | Excretion of drugs | |

EBC-3.2. Collection and Analysis of Other Vapor Condensates.

Certain embodiments of the present invention are related to the applications of the SiEBCA methods and devices for collection and analysis of the vapor condensates other than the EBC. The other moistures include, but not limited to, fog, clouds, steams, etc. The target analysis of these vapor condensates can be for different purpose environmental monitoring, emission control, etc. In some embodiments, the sample is a vapor from a biological sample, an environmental sample, a chemical sample, or clinical sample.

EBC-3.3. Automatic and High Throughput.

In certain embodiments, the devices and methods of the present invention are automatic and high speed, where the steps are performed by machines. In some embodiments, the plates are in the form of roll of sheets and are controlled by rollers to put certain area of the plates into an open configuration or a closed configuration.

EBC-4. More Examples of EBC Collection and Analysis Experiments

Additional exemplary experimental testing and observation, and additional preferred embodiments of the present invention are given.

All the exemplary experimental testing and demonstration of the present invention described in Section 4 (Examples) were performed under the following conditions and share the following common observations.

Plates.

Only one of the two plates of SiEBCA device, termed "X-Plate", has the spacers fixed on the sample surface of the plate, and the other plate, termed "the substrate plate", has a planar surface and does not have spacers. The substrate plate was used as the collection plate, and the X-plate was used as the cover plate. Various materials (including glass, PMMA (polymethacrylate), and PS (polystyrene)) for the plates and various plate thicknesses have been tested. The planar surface of the plates typically have surface roughness less than 30 nm.

Spacers.

The spacers used on the X-Plate are rectangle pillars in a periodic array with a fixed inner spacer distance (ISD) and uniform spacer height. The pillar spacers have a straight sidewall with a tilt angle from the normal less than 5 degree. Different spacer height, size, inter-spacer distance, shape, and materials are tested.

Fabrication of Spacers.

The spacers are fabricated by nanoimprint on a plastic plate, where a mold is pressed directly into the plate. The mold was fabricated by lithography and etching. Examples of the spacers on the plate for SiEBCA. The spacers are fabricated by direct imprinting of the plastic plate surface using a mold, and has a dimension of width, length and height of 30 µm, 40 µm and 2 µm.

EBC Sample Deposition.

All of the EBC samples were deposited on the collection plates by having a human subject directly exhale toward the collection plate which is placed within a few inches away from the subject's mouth.

The EBC samples depositions were performed in standard room conditions without any special temperature control or dust filters. We found that in our experiments, the dust does not affect to achieve the predetermined final sample thickness over a large sample area, and at the closed configuration the sample thickness over the non-dust area is regulated by the spacers. This demonstrated that the embodiments that we used for CROF performed to the results expected by the present invention.

Plate's Surface Wetting Properties.

Unless particularly specified, all the sample surfaces (i.e. the inner surface that contacts a sample) of the plates are untreated. We have tested the wetting properties of these untreated surfaces as a function of the plate material (glass, PMMA, and PS), the surface structures (planar or with spacers, and the sample type (water, PBS buffer and blood), by dropping a small drop of sample on the plate surface and measuring the sample to the plate contact angle. The wetting angles of the different surfaces for different samples were found experimentally as follows: For the liquid of water, PBS, and blood, the contact angle is about 46 degree for untreated glass, 60 degree for untreated PMMA surface, 60 degree for untreated PS (polystyrene) and about 61 degrees for untreated PMMA X-plate. Therefore they are all hydrophilic. But the wetting property of these surfaces can changed to either hydrophilic or hydrophobic by surface treatment. For a good vapor condensate collection, a hydrophilic surface is preferred, which will have, for a given amount of the condensation, smaller surface area that Hand-Press. In all the experiments in the Section, the plates in a SiEBCA process were brought together and compressed into a closed configuration of the plates all by human hand(s). In a final pressing for uniform sample thickness over a large area of the SiEBCA plates, often a thumb presses one area and rubs into different areas of the CROF plates, and excellent sample thickness uniformity were observed as detailed below. A process that uses hand(s) to press a SiEBCA device (plates) into a closed configuration is referred as "hand-pressing".

FIG. 5 gives exemplary methods of pressing the plates of SiEBCA by human hand. The SiEBCA can be pressed by either (a) placing the SiEBCA on a surface and uses a thumb to press one location of the SiEBCA and press and rub into other locations, or (b) placing the SiEBCA between a thumb and a figure and press and rub. In some cases, both hands can be used.

Self-Holding.

Self-holding means that after a SiEBCA device (plates) is compressed into a closed configuration by an external force (e.g. the force from hand) and after the external force is removed, the SiEBCA device can hold, on its own, the sample thickness unchanged. We observed that in all the experiments in the Sec., all the SiEBCA devices and process (unless particularly specified) can self-hold, as demonstrated in the experiments. Our other experimental test showed that as long as one of the plate is hydrophilic, the SiEBCA plates can self-hold.

EBC-4.1. EBC Formation on Collection Plate at Open and Closed Configurations 4.1.1 EBC Droplet Size on Untreated and Surface Treated PMMA Collection Plate FIG. 6. Experimental data of EBC Droplets sizes and density on the collection plate (untreated PMMA film) at an "open configuration" (i.e. only the collection plate without the cover plate). The photographs show the EBC collected on the collection plate after a subject directly breathe to the plate for four different breathing time: (a) 1 sec breath, (b) 2 sec breath, (c) 5 sec breath, and (d) 10 sec breath. The photographs were taken immediately after the breathing.

The table shows the measured average droplet size, the calculated average droplet height, the average drop volume, the measured droplet density, and the total liquid surface area on 1 mm-square area of the collection plate (PMMA). The experimental data show that (1) using a untreated PMMA film as the collection plate's collection surface, the EBC directly from a subject form droplets that have different sizes and are, for most droplets, well separated from each other; and (2) the measured average droplet size, the calculated average droplet height, the average droplet volume, the droplet density, and the total liquid surface area on 1 mm-square area of the collection plate (PMMA) initially increase with the breathing time, but seem to become saturated after 5 s breathing. This might be due to the fact that in the experiment, after 5 sec breathing, the EBC deposition rate by breathing and the evaporation rate of the existing EBC reach an equilibrium.

In the above experiment, the calculation of the average droplet height is based on the wetting contact angle of water on PMMA, and the volume density is calculated by multiplying the average droplet volume with the measured droplet amount density.

The table also shows that the average EBC volume is 172 pL, 250 pL, 491 pL, and 507 pL per sq-mm collection plate area, respectively, for 1 s, 2 s 5 s and 10 s breathing time.

FIG. 7. Experimental data of EBC formation on the collection plate, which is a surface treated PMMA film (the treatment made the surface more hydrophilic than an untreated PMMA film surface), at a plate open configuration. The photographs show that the EBC collected on the collection plate from a direct breathing by a subject for four different breathing time: (a) 1 sec breath, (b) 2 sec breath, (c) 5 sec breath, and (d) 10 sec breath. The photographs were taken immediately after the breathing. Assuming there were the same amount of EBC deposited on the collection plate with treated surface as in the case of untreated surface, the average liquid thickness was therefore calculated by dividing the total volume by the observed liquid sample area on the 1 mm$^2$ collection plate. The table shows the volume density per unit surface area, the calculated average liquid thickness, and the total liquid surface area on 1 mm$^2$ area of the collection plate (PMMA).

The experimental data in FIG. 7 clearly show that: (1) due to the hydrophilic surface with smaller contact angle of the treated PMMA (details given in FIG. 8), the EBC deposited directly from a subject to the collection plate forms, at an open configuration, a few large-area EBC puddles rather than many small droplets; and (2) the total liquid (EBC) surface area on 1 mm-square area for the EBC collected using the collection plate with surface treatment (hence bettering wetting) is about 4 times less that without the surface treatment.

FIG. 8. Photographs and measured evaporation time (at plate open configuration) of the EBC (2 s breathing directly from a subject) collected on untreated and treated PMMA plate. The photographs show that the EBC collected on the untreated PMMA collection plate form many small well separated droplets (a), while the EBC collected on the treated PMMA collection plate form a few thin film and large puddles with large voids (b). The calculated surface area of the EBC collected on the untreated surface is 4 times larger than that on the untreated surface. And the EBC collected on the untreated surface has a total evaporation time of 7 s, which is about 4 times shorter than that collected on the treated surface, which is 30 s. More studies of the evaporation time are given in FIGS. 13 and 14 and described below.

4.1.2 EBC Formation when the Plates are in a Closed Configuration

Experimentally, we observed that the final form of the EBC collected by SiEBCA when the plates are in the closed configuration depends upon the spacer height.

FIGS. 9 and 10 show, respectively, the photographs and experimental data of spacer height effects (1 μm, 2 μm, 10

μm and 30 μm, respectively) on the EBC collected using SiEBCA at the closed configuration. The breathing time is 2 s and the covering time delay is nearly 0 s. The spacers are pillars of uniform cross-section (30 μm×38 μm) with flat top and bottom surfaces and a constant inter spacer distance of 80 μm and 82 μm (X and Y direction). The cover plate is an untreated X-plate of 175 μm thick PMMA film and the collection plate is a flat glass plate (25 mm×25 mm×1 mm). As calculated, the average height of the droplets at the open configuration that are collected on the untreated surface from 2 s breathing is 1.7 μm. Here, the experiments show that:

(1) For all the spacer heights tested (shown in FIG. 9), the EBC on the collection plate merged from the droplets formed when the plates were at an open configuration to puddles that are fewer in number but much larger in lateral size when the plates were at the closed configuration.

(2) 1 μm gapping X-device collected the largest amount of breath liquid with the best liquid thickness uniformity and in continuous films.

(3) X-devices with gapping larger than 1 μm collect collected less breath liquid and were hard to self-hold well, thus had worse liquid thickness uniformity and deviation from pillar height.

Therefore, experimentally, we demonstrated that:

(1) At the closed configuration of the SiEBCA, if the spacing between the plate sample surfaces of the plates is less than the average height of the EBC droplets or puddles at the open configuration (e.g. the spacing was 1 μm and the average height was 1.7 μm), the EBC droplets or puddles are compressed by the collection plate and the cover plate into a continuous film of a thickness thinner than the open configuration, and also air pockets may exist in the film; and (2) otherwise (e.g., the pillar height was 2 μm, 10 μm, or 30 μm, respectively, but the EBC at the open configuration was only 1.7 μm height) the droplets and or puddles first raised up to touch both sample contact (inner) surfaces of the cover plate and the collection plate, and then self-emerged to discrete puddles that are fewer in number but larger in lateral size (area) than that in the open configuration, and have the thickness confined by the inner surfaces of the plates and equal to the spacing between the inner surfaces. In this case, the EBC sample thickness at the closed configuration is equal to or larger than the EBC sample average thickness at the open configuration. The increase in the EBC puddle thickness at the closed configuration, as we observed experimentally, are due to the interactions between the plates and the EBC sample.

4.1.3 EBC Evaporation Time as Function of the Covering Delay Time

FIGS. 11 and 12 show, respectively, photographs and experimental data of the effects on breath collection of (a) treated versus untreated PMMA collection plates and (b) time delay in closing the cover plate. In the experiments, the EBC was collected directly from 2 s breathing of a subject on a collection plate (PMMA 25 mm×25 mm×1 mm); some collection plates were untreated, but some were treated to have a better hydrophilicity than the untreated PMMA collection plate; the cover plate was an X-plate of 175 μm thick PMMA with a square lattice of pillar-shaped spacers of flat top (1 μm height, 30 μm width, and 38 μm long) with inter-spacer distance of 80 μm and 82 μm in x and y direction respectively; two different time delays in covering the collection plate with the cover plate were tested: immediately after the completion of the breath or 5s after the completion of the breath; and the liquid thickness, the collected breath liquid volume, the Liquid thickness deviation from pillar height, Liquid thickness uniformity, and other parameters (e.g. Liquid Area (mm2) on 25 mm×25 mm collection plate, (Liquid Area) over (Total Area—Spacer Area) were measured all at the plate closed configuration.

Through the experimental study, we found that:

(1) Compared with untreated PMMA collection plate, the treated collection plates (better wetting) collect more breath liquid at both delay times of "immediate press" and "at 5s press".

(2) Using the untreated collection plates (less hydrophilic), at 5s delay time for covering, almost a half of the liquid evaporated.

(3) For all the samples, after the hand pressing, the plates in SiEBCA can self-hold.

(4) In most cases, at the closed configuration, for most of the delay times, the measured deviation of the EBC average thickness from the spacer height is equal to or less than 7.4% and the measured EBC thickness uniformity (i.e. variation) is equal to or less than 6.4%. But when the collection surface is untreated (less hydrophilic) and the time delay for coving the cover plate is 5 s, the average EBC thickness deviates from the spacer height is large (1.52 μm compared to 1 μm, leading to a 52% relative deviation) and the thickness uniformity is poor: 22% variation.

FIG. 13. Experimental data of the volume of the collected breath (i.e. EBC) on the collection plate vs. the time delay (measured from the end of the breath to the covering of the cover plate) in the case of the treated (which is more hydrophilic that the untreated) and untreated collection plate (PMMA) surface, respectively. In the experiments, the breathing time was 2 s. The collected breath volume was measured after the cover plate and the collection plate were pressed to the closed configuration. From the experiments, we found that:

(1) For a given time delay, the collection plate with a treated surface (more wetting than untreated) had more breath liquid collected.

(2) Without covering the collection plate, the EBC from the 2 s breath lasted only 7 s for the collection plate with untreated surface, but 30 s for the collection plate with treated surface, which is 4 times longer.

The observation (2) further shows that with a more wetting surface on the collection plate, the total surface area of the EBC deposited on the plate has a smaller surface area than that deposited on the untreated area, and hence there is a longer drying time on the treated surface (i.e. the time before completely drying out).

4.1.4 EBC Evaporation Time at Plate Open and Closed Configuration

We experimentally studied the evaporation time of the EBC deposited on the collection plate without and with the cover plate placed on top of the EBC (i.e. the evaporation time for the plates being in the open configuration and the closed configuration.

The evaporation rate of the EBC on the collection plate at the open configuration has been given and described in FIG. 8.

FIG. 14. Experiment Data for drying time of EBC collected by SiEBCA at "Closed configuration" in the case of the treated (which is more hydrophilic that the untreated) and untreated collection plate (PMMA) surface, respectively, and at different spacer height. In the experiments, the breath time was 2 s., and the cover plate was immediately covered after the breath. The experiments showed that: the treated PMMA collection plate with a 1 μm spacer allowed a drying time of 70 s, but the drying time reduced to 45 s if the spacer was 10 μm. The reason for a shorter drying time at 10 μm spacer is due to the fact that the EBC at the plate closed configuration form many isolated puddles, which has more surface area to be exposed to the environment than that in a 1 μm spacer height SiEBCA which has one or a few large EBC areas.

We realized that by using an enclosed spacer in addition to the isolated spacers, we can further reduce the EBC evaporation rate at a closed configuration of SiEBCA.

Drying speed with treated and untreated collection plates. For both experiments using treated and untreated collection plates, the drying speed of EBC was also calculated, which is defined as the retraction length per unit time of the edge of the liquid sample in the X-device at the closed configuration. The calculation shows that with the treated PMMA collection plate, the liquid sample dried at a slower speed (74 μm/min) as compared to with the untreated PMMA collection plate (117 μm/min).

Surface treatment. The surface treatment of the PMMA plate was performed with oxygen plasma, followed by deposition of 10 nm silicon oxide. In some embodiments, the treatment was performed chemically using trimethoxysilane.

Compressed Regulated Open Flow" (CROF)

Many embodiments of the present invention manipulate the geometric size, location, contact areas, and mixing of a sample and/or a reagent using a method, termed "compressed regulated open flow (CROF)", and a device that performs CROF.

The term "compressed open flow (COF)" refers to a method that changes the shape of a flowable sample deposited on a plate by (i) placing other plate on top of at least a part of the sample and (ii) then compressing the sample between two plates by pushing the two plates towards each other; wherein the compression reduces a thickness of at least a part of the sample and makes the sample flow into open spaces between the plates.

The term "compressed regulated open flow" or "CROF" (or "self-calibrated compressed open flow" or "SCOF" or "SCCOF") refers to a particular type of COF, wherein the final thickness of a part or entire sample after the compression is "regulated" by spacers, wherein the spacers, that are placed between the two plates.

The term "the final thickness of a part or entire sample is regulated by spacers" in a CROF means that during a CROF, once a specific sample thickness is reached, the relative movement of the two plates and hence the change of sample thickness stop, wherein the specific thickness is determined by the spacer.

One embodiment of the method of CROF, as illustrated in FIG. 1-4, comprises:

(a) obtaining a sample, that is flowable;

(b) obtaining a first plate and a second plate that are movable relative to each other into different configurations, wherein each plate has a sample contact surface that is substantially planar, wherein one or both of the plates comprise spacers and the spacers have a predetermined height, and the spacers are on a respective sample contacting surface;

(c) depositing, when the plates are configured in an open configuration, the sample on one or both of the plates; wherein the open configuration is a configuration in which the two plates are either partially or completely separated apart and the spacing between the plates is not regulated by the spacers; and (d) after (c), spreading the sample by bringing the plates into a closed configuration, wherein, in the closed configuration: the plates are facing each other, the spacers and a relevant volume of the sample are between the plates, the thickness of the relevant volume of the sample is regulated by the plates and the spacers, wherein the relevant volume is at least a portion of an entire volume of the sample, and wherein during the sample spreading, the sample flows laterally between the two plates.

The term "plate" refers to, unless being specified otherwise, the plate used in a CROF process, which a solid that has a surface that can be used, together with another plate, to compress a sample placed between the two plate to reduce a thickness of the sample.

The term "the plates" or "the pair of the plates" refers to the two plates in a CROF process.

The term "first plate" or "second plate" refers to the plate use in a CROF process.

The term "the plates are facing each other" refers to the cases where a pair of plates are at least partially facing each other.

The term "spacers" or "stoppers" refers to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value. There are two types of the spacers: "open-spacers" and "enclosed-spacers".

The term "open-spacer" means the spacer have a shape that allows a liquid to flow around the entire perimeter of the spacer and flow pass the spacer. For example, a pillar is an open spacer.

The term of "enclosed spacer" means the spacer of having a shape that a liquid cannot flow abound the entire perimeter of the spacer and cannot flow pass the spacer. For example, a ring shape spacer is an enclosed spacer for a liquid inside the ring, where the liquid inside the ring spacer remains inside the ring and cannot go to outside (outside perimeter).

The term "a spacer has a predetermined height" and "spacers have predetermined inter-spacer distance" means, respectively, that the value of the spacer height and the inter spacer distance is known prior to a CROF process. It is not predetermined, if the value of the spacer height and the inter-spacer distance is not known prior to a CROF process. For example, in the case that beads are sprayed on a plate as spacers, where beads are landed on random locations of the plate, the inter-spacer distance is not predetermined. Another example of not predetermined inter spacer distance is that the spacers moves during a CROF processes.

The term "a spacer is fixed on its respective plate" in a CROF process means that the spacer is attached to a location of a plate and the attachment to that location is maintained during a CROF (i.e. the location of the spacer on respective plate does not change). An example of "a spacer is fixed with its respective plate" is that a spacer is monolithically made of one piece of material of the plate, and the location of the spacer relative to the plate surface does not change during CROF. An example of "a spacer is not fixed with its respective plate" is that a spacer is glued to a plate by an adhesive, but during a use of the plate, during CROF, the adhesive cannot hold the spacer at its original location on the plate surface and the spacer moves away from its original location on the plate surface.

The term "a spacer is fixed to a plate monolithically" means the spacer and the plate behavior like a single piece of an object where, during a use, the spacer does not move or separated from its original location on the plate.

The term "open configuration" of the two plates in a CROF process means a configuration in which the two plates are either partially or completely separated apart and the spacing between the plates is not regulated by the spacers The term "closed configuration" of the two plates in a CROF process means a configuration in which the plates are facing each other, the spacers and a relevant volume of the sample are between the plates, the thickness of the relevant volume of the sample is regulated by the plates and the spacers, wherein the relevant volume is at least a portion of an entire volume of the sample.

The term "a sample thickness is regulated by the plate and the spacers" in a CROF process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a CROF device refers to the surface of the plate that touches the sample, while the other surface (that does not touch the sample) of the plate is termed "outer surface".

The term "X-Plate" of a CROF device refers to a plate that comprises spaces that are on the sample surface of the plate, wherein the spacers have a predetermined inter-spacer distance and spacer height, and wherein at least one of the spacers is inside the sample contact area.

The term "CROF device" refers to a device that performs a CROF process. The term "CROFed" means that a CROF process is used. For example, the term "a sample was CROFed" means that the sample was put inside a CROF device, a CROF process was performed, and the sample was hold, unless stated otherwise, at a final configuration of the CROF.

The term "CROF plates" refers to the two plates used in performing a CROF process.

The term "surface smoothness" or "surface smoothness variation" of a planar surface refers to the average deviation of a planar surface from a perfect flat plane over a short distance that is about or smaller than a few micrometers. The surface smoothness is different from the surface flatness variation. A planar surface can have a good surface flatness, but poor surface smoothness.

The term "surface flatness" or "surface flatness variation" of a planar surface refers to the average deviation of a planar surface from a perfect flat plane over a long distance that is about or larger than 10 µm. The surface flatness variation is different from the surface smoothness. A planar surface can have a good surface smoothness, but poor surface flatness (i.e. large surface flatness variation).

The term "relative surface flatness" of a plate or a sample is the ratio of the plate surface flatness variation to the final sample thickness.

The term "final sample thickness" in a CROF process refers to, unless specified otherwise, the thickness of the sample at the closed configuration of the plates in a CORF process.

The term "compression method" in CROF refers to a method that brings two plates from an open configuration to a closed configuration.

The term of "interested area" or "area of interest" of a plate refers to the area of the plate that is relevant to the function that the plates perform.

The term "at most" means "equal to or less than". For example, a spacer height is at most 1 µm, it means that the spacer height is equal to or less than 1 µm.

The term "sample area" means the area of the sample in the direction approximately parallel to the space between the plates and perpendicular to the sample thickness.

The term "sample thickness" refers to the sample dimension in the direction normal to the surface of the plates that face each other (e.g., the direction of the spacing between the plates).

The term "plate-spacing" refers to the distance between the inner surfaces of the two plates.

The term "deviation of the final sample thickness" in a CROF means the difference between the predetermined spacer height (determined from fabrication of the spacer) and the average of the final sample thickness, wherein the average final sample thickness is averaged over a given area (e.g. an average of 25 different points (4 mm apart) over 1.6 cm by 1.6 cm area).

The term "uniformity of the measured final sample thickness" in a CROF process means the standard deviation of the measured final sample thickness over a given sample area (e.g. the standard deviation relative to the average.).

The term "relevant volume of a sample" and "relevant area of a sample" in a CROF process refers to, respectively, the volume and the area of a portion or entire volume of the sample deposited on the plates during a CROF process, that is relevant to a function to be performed by a respective method or device, wherein the function includes, but not limited to, reduction in binding time of analyte or entity, detection of analytes, quantify of a volume, quantify of a concentration, mixing of reagents, or control of a concentration (analytes, entity or reagents).

The term "some embodiments", "in some embodiments" "in the present invention, in some embodiments", "embodiment", "one embodiment", "another embodiment", "certain embodiments", "many embodiments", or alike refers, unless specifically stated otherwise, to an embodiment(s) that is (are) applied to the entire disclosure (i.e. the entire invention).

The term "height" or "thickness" of an object in a CROF process refers to, unless specifically stated, the dimension of the object that is in the direction normal to a surface of the plate. For example, spacer height is the dimension of the spacer in the direction normal to a surface of the plate, and the spacer height and the spacer thickness means the same thing.

The term "area" of an object in a CROF process refers to, unless specifically stated, the area of the object that is parallel to a surface of the plate. For example, spacer area is the area of the spacer that is parallel to a surface of the plate.

The term "lateral" or "laterally" in a CROF process refers to, unless specifically stated, the direction that is parallel to a surface of the plate.

The term "width" of a spacer in a CROF process refers to, unless specifically stated, a lateral dimension of the spacer.

The term "a spacer inside a sample" means that the spacer is surrounded by the sample (e.g. a pillar spacer inside a sample).

The term "critical bending span" of a plate in a CROF process refers the span (i.e. distance) of the plate between two supports, at which the bending of the plate, for a given flexible plate, sample, and compression force, is equal to an allowed bending. For example, if an allowed bending is 50 nm and the critical bending span is 40 µm for a given flexible plate, sample, and compression force, the bending of the plate between two neighboring spacers 40 µm apart will be 50 nm, and the bending will be less than 50 nm if the two neighboring spacers is less than 40 μm.

The term "flowable" for a sample means that when the thickness of the sample is reduced, the lateral dimension increases. For an example, a stool sample is regarded flowable.

In some embodiments of the present invention, a sample under a CROF process do not to be flowable to benefit from the process, as long as the sample thickness can be reduced under a CROF process. For an example, to stain a tissue by put a dye on a surface of the CROF plate, a CROF process can reduce the tissue thickness and hence speed up the saturation incubation time for staining by the dye.

1. Reducing (Shortening) Binding or Mixing Time (X)

It is desirable to reduce the incubation/reaction time in performing assays or other chemical reactions. For example, in the surface immobilization assays where a target analyte in a sample is detected by being captured by capture agents immobilized on a plate surface (i.e. a solid phase), it is often desirable to have a short saturation incubation time for capturing target analytes in the sample, or immobilizing of the capture agents and detection agents in a solution on a plate surface, or both. Another example is the need to shorten the time of coating a capture agent to a plate surface. And another example is the need to shorten the time of mixing a reagent into a sample.

The present invention provides the methods and devise that reduce (i.e. shorten) the saturation incubation time needed for binding an entity in sample to a binding site on a solid surface (i.e. the time for an entity from a volume to a surface). Another aspect of the present invention is to reduce the time needed for a binding of an entity stored on a plate surface to a binding site on another plate surface (i.e. the time for an entity from one surface to another surface). Another aspect of the present invention is to reduce the time needed for adding/mixing of a reagent stored on a surface into a volume of a sample (i.e. a time for adding/mixing a reagent from a surface into a volume of a sample).

The present invention reduces the saturation incubation time of binding and/or mixing in an assay by using the devices and methods that spread a sample (or a liquid) to a thinner thickness, thereby reducing the time for an entity diffusing across the sample's thickness. A diffusion time of an entity in a material (e.g. liquid or solid or semi-solid) is proportional to the square to the diffusion distance, hence a reduction of the sample thickness can reduce the diffusion distance, leading to drastically reduction of diffusion time and the saturation incubation time. A thinner thickness (e.g. a tight confined space) also increases the frequency of collisions of an entity with other entities in a material, further enhancing a binding and a mixing. The means in the present invention also make the reduction of the sample's thickness precise, uniform, fast, simple (less operation steps) and applicable to reduce the sample thickness to micrometer or nanometer thick. The inventions have great utilities in fast, low-cost, PoC, diagnostics and chemical/bio analysis. Several embodiments of the present invention are illustrated in FIG. 1-4.

1.1 Reducing the Saturation Incubation Time of Binding an Entity in a Sample to a Binding Site on a Solid Surface by Reducing the Sample Thickness.

X1. A method for reducing the saturation incubation time of binding a target entity in a sample to a binding site of a plate surface, as illustrated in FIGS. 1-4 and 15, comprising:

(a) obtaining a sample that is flowable and contains a target entity which is capable of diffusing in the sample;

(b) obtaining a first plate and a second plate that are movable relative to each other into different configurations, wherein the first plate has, on its surface, a binding site that is configured to bind the target entity, wherein one or both of the plates comprise spacers, and each of the spacers is fixed with its respective plate and has a predetermined height;

(c) depositing, when the plates are configured in an open configuration, the sample on one or both of the plates; wherein the open configuration is a configuration in which the two plates are either partially or completely separated apart and the spacing between the plates is not regulated by the spacers;

(d) after (c), spreading the sample by bringing the plates into a closed configuration, wherein, in the closed configuration: the plates are facing each other, the spacers and a relevant volume of the sample are between the plates, the binding site is in contact with the relevant volume, and the thickness of the relevant volume of the sample is regulated by the plates and the spacers, is thinner than the maximum thickness of the sample when the plates are in the open configuration;

wherein the relevant volume is a portion or an entire volume of the sample; and wherein the reduced thickness of the sample reduces the saturation incubation time for binding of the target entity in the relevant volume to the binding site.

For a given sample volume, a CROF reduces sample thickness but increase the sample lateral dimension. The present invention utilize the fact to perform (a) local binding or mixing in portion of the sample, and (b) multiplexing of multiple binding or mixing sites, without a fluidic barrier to fluidically separate a sample into different isolation liquid pockets.

X2. A device for reducing the saturation incubation time to bind target entity in a relevant volume of a sample to a surface, as illustrated in FIGS. 1-4 and 15, comprising:

a first plate and a second plate that (a) are movable relative to each other into different configurations, (b) each plate has a sample contact area for contacting a sample that has a target entity in a relevant volume of the sample, (c) one of the plate has binding site that binds the target entity, and (d) at least one of the plates comprises spacers that have a predetermined inter-spacer distance and height and are fixed on its respective surface, wherein at least one of the spacers is inside the sample contact area;

wherein one of the configurations is an open configuration, in which: the two plates are either partially or completely separated apart, and the spacing between the plates is not regulated by the spacers, wherein another of the configuration is a closed configuration, which is configured after the sample deposition in an open configuration; and in the closed configuration: the plates are facing each other, the spacers and the relevant volume of the sample are between the plates, the binding site is in contact with the relevant volume, and the thickness of the relevant volume of the sample is regulated by the plates and the spacers, is thinner than the maximum thickness of the sample when the plates are in the open configuration; wherein the relevant volume is a portion or an entire volume of the sample; and wherein the reduced thickness of the sample reduces the saturation incubation time for a binding of the target entity in the relevant volume to the binding site.

1.2 Reducing Saturation Incubation Time for a Binding of an Entity Stored on One Plate Surface to a Binding Site on Another Plate Surface X3. A method for reducing the saturation incubation time to bind an entity stored on a storage site of one plate to a relevant binding site on another plate, as illustrated in FIGS. 1-4 and 15b, comprising:

(a) obtaining a first plate and a second plate that are movable relative to each other into different configurations, wherein a surface of first plate has a binding site, and a surface of the second plate has a storage site that contains an entity to be bound to the binding site; wherein the area of the binding site and the area of the storage site is less than that of respective plates; and wherein one or both of the plates comprise spacers and each of the spacers is fixed with its respective plate and has a predetermined height;

(b) obtaining a transfer medium, wherein the entity on the storage site are capable of being dissolving into the transfer medium and diffusing in the transfer medium;

(c) depositing, when the plates are configured in an open configuration, the transfer medium on one or both of the plates; wherein the open configuration is a configuration in which the two plates are partially or completely separated apart and the spacing between the plates is not regulated by the spacers;

(d) after (c), spreading the transfer medium by bringing the plates into a closed configuration, wherein, in the closed configuration: the plates are facing each other, the spacers, the binding site, the storage site and at least a portion of the transfer medium are between the plates, the binding site and the storage site are at least partially on top of each other, the transfer medium contacts at least a part of the binding site and the storage site, the thickness of the transfer medium is regulated by the plates and the spacers, is thinner than the maximum thickness of the transfer medium when the plates are in the open configuration;

wherein the reduced thickness of the transfer medium reduces the time for the binging of the entity stored on the second plate to the binding site on the first plate.

X4. A device for reducing the saturation incubation time for binding an entity stored on a storage site of one plate to a binding site on another plate, as illustrated in FIGS. 1-4, and 15b, comprising:

a first plate and a second plate that are movable relative to each other into different configurations, wherein a surface of first plate has a binding site; and a surface of the second plate has a storage site that contains an entity to be bound to the binding site; wherein the area of the binding site and the area of the storage site is less than that of respective plates; and wherein one or both of the plates comprise spacers and each of the spacers is fixed with its respective plate and has a predetermined height;

wherein one of the configurations is an open configuration, in which: the two plates are either partially or completely separated apart, the spacing between the plates is not regulated by the spacers, and a transfer medium can be deposited on one or both of the plates, wherein the entity on the storage site are capable of being dissolving into the transfer medium and diffusing in the transfer medium, wherein another of the configuration is a closed configuration, which is configured after the transfer medium deposition in an open configuration; and in the closed configuration: the plates are facing each other, the spacers, the binding site, the storage site and at least a portion of the transfer medium are between the plates, the binding site and the storage site are at least partially on top of each other, the transfer medium contacts at least a part of the binding site and the storage site, the thickness of the transfer medium is regulated by the plates and the spacers, is thinner than the maximum thickness of the transfer medium when the plates are in the open configuration;

wherein the reduced thickness of the transfer medium reduces the saturation incubation time for a binging of entity on the storage site of the second plate to the binding site of the first plate.

In the method of paragraph X3 and the device of paragraph X4, in some embodiments, the transfer medium comprises a liquid that allows a diffusion of the entity or a reagent or both.

In the method of paragraph X3 and the device of paragraph X4, in some embodiments, the transfer medium is a sample, where the sample contains an analyte (also termed target analyte) that binds the binding site.

In the method of paragraph X3 and the device of paragraph X4, in some embodiments, the transfer medium is a sample, where the sample contains an analyte (also termed target analyte) that binds the binding site and the reagent is a detection agent that binds to the analytes.

1.3 Reducing the Time for Adding (Mixing) Reagent Stored on Surface into a Liquid Sample Many assays need to have reagents added into a sample (including a liquid). Often the concentration of the added reagents in the sample or the liquid need to be controlled. There are needs for new methods that are simple and/or low cost to perform such reagents addition and concentration control. Two examples where reagents additions are needed are (a) blood cell counting where anticoagulant and/or staining reagent(s) may be added into a blood sample, and (b) immunoassays where detection agents are added to bind a target analyte in solution.

One aspect of the present invention is the methods, devices, and systems that make the reagent addition and the reagent concentration control simple and/or low cost. In one embodiment of the current invention, a reagent layer (e.g. dried reagent layer) is first put on a plate surface of a CROF device, then a sample is deposited into the CROF device, and a CROF process makes the sample in contact with the reagent and the sample thickness thinner than the thickness when the sample at the open configuration of the CROF plates. By reducing the sample thickness, it would reduce the diffusion time of the reagent diffuses from the surface into the entire sample, and hence it reduces the time for mixing the reagent with the sample.

X5. A method for reducing the time for mixing a reagent stored on a plate surface into a sample, as illustrated in FIGS. 1-4, and 15c, comprising:

(a) obtaining a first plate and a second plate that are movable relative to each other into different configurations, wherein the first plate has, on its surface, a storage site that contains reagents to be added into a sample, and the reagents are capable of being dissolving into the sample and diffusing in the sample; and wherein one or both of the plates comprise spacers and each of the spacers is fixed with its respective plate and has a predetermined height;

(b) obtaining the sample;
(c) depositing, when the plates are configured in an open configuration, the sample on one or both of the plates; wherein the open configuration is a configuration in which the two plates are partially or completely separated apart and the spacing between the plates is not regulated by the spacers;
(d) after (c), spreading the sample by bringing the plates into a closed configuration, wherein, in the closed configuration: the plates are facing each other, the spacers, the storage site, and at least a portion of the sample are between the plates, the sample contacts at least a portion of the storage site, the thickness of the sample on the storage site is regulated by the plates and the spacers, is thinner than the maximum thickness of the sample when the plates are in the open configuration;
wherein the reduced thickness of the sample reduces the time for mixing the reagents on the storage site with the sample.

In the method of paragraph X5, it further comprises a step of incubation while the plates are in the closed configuration, wherein the incubation time is selected in such that results in a significant number of the reagents dissolved in the sample are contained in the relevant volume of the sample, wherein the relevant volume is the volume of the sample that sits on the storage site and the incubation is a process to allow the reagent to dissolve and diffuse in the sample.

In the method of paragraph X5, it further comprises a step that, after (d) and while the plates are in the closed configuration, incubating for a time equal or less than a factor times the diffusion time of the reagent in the sample across the sample thickness regulated by the plates at the closed configuration, and then stopping the incubation; wherein the incubation allows the reagent to diffuse into the sample; and wherein the factor is 0.0001, 0.001, 0.01, 0.1, 1, 1.1, 1.2, 1.3, 1.5, 2, 3, 4, 5, 10, 100, 1000, 10,000, or a range between any to the values. For example, if the factor is 1.1 and the diffusion time is 20 seconds, then the incubation time is equal to or less than 22 second. In one preferred embodiment, the factor is 0.1, 1, 1.5 or a range between any to the values.

X6. A device for reducing the time to add a reagent stored on a plate surface into a sample, as illustrated in FIGS. 1-4 and 15c, comprising:
a first plate and a second plate that are movable relative to each other into different configurations, wherein the first plate has, on its surface, a storage site that contains reagents to be added into a sample, the reagents are capable of being dissolving into the sample and diffusing in the sample; and wherein one or both of the plates comprise spacers and each of the spacers is fixed with its respective plate and has a predetermined height;
wherein one of the configurations is an open configuration, in which: the two plates are either partially or completely separated apart, the spacing between the plates is not regulated by the spacers, and the sample is deposited on one or both of the plates;
wherein another of the configuration is a closed configuration, which is configured after the transfer medium deposition in the open configuration; and in the closed configuration: the plates are facing each other, the spacers, the storage site, and at least a portion of the sample are between the plates, the sample contacts at least a portion of the storage site, the thickness of the sample on the storage site is regulated by the plates and the spacers, is thinner than the maximum thickness of the sample when the plates are in the open configuration;
wherein the reduced thickness of the sample reduces the time for mixing the reagents on the storage site with the sample.

In the method or the devices of any of paragraphs X1-6, in some embodiments, the relevant volume of the sample is the volume of the sample that sits on (i.e. on top of) the binding site or the storage site.

In the method or the devices of any of paragraphs X1-6, in some embodiments, the relevant volume of the sample is the volume of the sample that sits on (i.e. on top of) the entire area or a partial area of the binding site or the storage site.

In the method or the devices of any of paragraphs X1-6, in some embodiments, the ratio of the lateral dimension of the binding site or the storage site to the sample thickness at the closed configuration is 1.5 3 or larger, 3 or larger, 5 or larger, 10 or larger, 20 or larger, 30 or larger, 50 or larger, 100 or larger, 200 or larger, 1000 or larger, 10,000 or larger, or a range between any two of the values.

In the method or the devices of any of paragraphs X1-6, the ratio of the lateral dimension of the binding site or the storage site to the sample thickness at the closed configuration is between 3 and 20 in a preferred embodiment, 20 and 100 in another preferred embodiment, and 100 and 1000 in another preferred embodiment, and 1000 and 10,000 in another preferred embodiment.

In the method of any of paragraphs X1 and X3, in some embodiments, the final reduced sample thickness is significantly smaller than that of the area of the binding site, so that the entity in the sample area that is outside of the binding site will take longer time to bind to the binding site. With a proper selection of the incubation time, the entity that bind to the binding sites will be primarily the entity in the sample volume that sites on the binding site (i.e. the sample volume that is just above the binding area). Then the calculation of the concentration of the entity in the sample would be based on the sample thickness and the binding site area.

In the method of paragraph X5, in some embodiments, the final reduced sample thickness is significantly smaller than that of the area of the storage site, so that the entity In the sample area that is outside of the binding site will take longer time to bind to the binding site. With a proper selection of the incubation time, the entity that bind to the binding sites will be primarily the entity in the sample volume that sites on the binding site (i.e. the sample volume that is just above the binding area). Then the calculation of the concentration of the entity in the sample would be based on the sample thickness and the binding site area.

In the method of any of paragraphs X2, X4, X6, it further comprises a compressing device that bring the plates from an open configurations to a closed configurations. In some embodiments, the compressing device is one or any combination of the embodiments described in the disclosures In the method of any of paragraphs X2, X4, X6, it further comprises a compressing device that bring the plates from an open configurations to a closed configurations, and a holding device that is configured to hold the plates are in the closed configuration. In some embodiments, the holding device is one or any combination of the embodiments described in the disclosures.

In the method of any of paragraphs X2, X4, X6, it further comprises a compressing device that bring the plates from an open configurations to a closed configurations, and a holding device that is configured to hold the plates are in the closed configuration for a time of 0.001 sec or less, 0.01 sec or less, 0.1 sec or less, 1 sec or less, 5 sec or less, 10 sec or less, 20 sec or less, 30 sec or less, 40 sec or less, 1 min or less, 2 min or less, 3 min or less, 5 min or less, 10 min or less, 20 min or less, 30 min or less, 60 min or less, 90 min or less, 120 min or less, 180 min or less, 250 min or less, or a range between any two of these values.

In the method of any of paragraphs X2, X4, X6, it further comprises a compressing device that bring the plates from an open configurations to a closed configurations, and a holding device that is configured to hold the plates are in the closed configuration for a time of, in a preferred embodiment, 0.001 sec or less, 0.01 sec or less, 0.1 sec or less, 1 sec or less, 5 sec or less, 10 sec or less, 20 sec or less, 30 sec or less, 40 sec or less, 1 min or less, 2 min or less, 3 min or less, or a range between any two of these values.

Incubation Time. In the method of any of paragraphs X1 and X3, it further comprises a step that, after (d) and while the plates are in the closed configuration, incubating for a time equal or less than a factor times the diffusion time of the entity in the sample diffusing across the sample thickness regulated by the plates at the closed configuration, and then stopping the incubation; wherein the incubation allows binding of the entity to the binding site; and wherein the factor is 0.0001, 0.001, 0.01, 0.1, 1, 1.1, 1.2, 1.3, 1.5, 2, 3, 4, 5, 10, 100, 1000, 10,000, or a range between any to the values. For example, if the factor is 1.1 and the diffusion time is 20 seconds, then the incubation time is equal to or less than 22 second. In one preferred embodiment, the factor is 0.1, 1, 1.5 or a range between any to the values.

In the method of paragraphs X5, it further comprises a step that, after (d) and while the plates are in the closed configuration, incubating for a time equal or less than a factor times the diffusion time of the reagents diffusing across the sample thickness regulated by the plates at the closed configuration, and then stopping the incubation; wherein the incubation allows binding of the entity to the binding site; and wherein the factor is 0.0001, 0.001, 0.01, 0.1, 1, 1.1, 1.2, 1.3, 1.5, 2, 3, 4, 5, 10, 100, 1000, 10,000, or a range between any to the values. For example, if the factor is 1.1 and the diffusion time is 20 seconds, then the incubation time is equal to or less than 22 second. In one preferred embodiment, the factor is 0.1, 1, 1.5 or a range between any to the values.

The method of any of paragraphs of X1, X3 and X5, or the device of any of paragraph of X2, X4, and X6, wherein at least one of the spacers is inside the sample contact area.

The method of any of paragraphs of X1, X3 and X5, or the device of any of paragraph of X2, X4, and X6, wherein spacers that have a predetermined inter-spacer distance.

In the method of any of paragraphs X1, X3, X5, it further comprises a step of incubation while the plates are in the closed configuration, the saturation incubation time is 0.001 sec or less, 0.01 sec or less, 0.1 sec or less, 1 sec or less, 5 sec or less, 10 sec or less, 20 sec or less, 30 sec or less, 40 sec or less, 1 min or less, 2 min or less, 3 min or less, 5 min or less, 10 min or less, 20 min or less, 30 min or less, 60 min or less, 90 min or less, 120 min or less, 180 min or less, 250 min or less, or a range between any two of these values.

In the method of any of paragraphs X1, X3, X5, the saturation incubation time at the reduced sample thickness at the closed configuration is 0.001 sec or less, 0.01 sec or less, 0.1 sec or less, 1 sec or less, 5 sec or less, 10 sec or less, 20 sec or less, 30 sec or less, 40 sec or less, 1 min or less, 2 min or less, 3 min or less, 5 min or less, 10 min or less, 20 min or less, 30 min or less, 60 min or less, 90 min or less, 120 min or less, 180 min or less, 250 min or less, or a range between any two of these values.

In some embodiments, capture agents are first immobilized at the binding site, then the sample are in contact with the binding site and the entity in the sample are captured by the capture agents, and finally detection agents are added to be bound with the captured entity and the a signal from the detection agents will be read (e.g. by optical methods or electrical methods or a combination). In some embodiments, other reagents besides of capture agents and detection agents are added (e.g. blocking agent).

In many applications such as PoC, it is desirable to have simple and/or low-cost devices and methods to add additional reagents into a sample. One aspect of the present invention is related to simple and/or low-cost devices and methods to add additional reagents into a sample. The added additional reagents include detection agents, blocking agents, light signal enhancers, light signal quenchers, or others. In some embodiments of the present invention, it controls the assay processes by using different release time of the reagents stored on the same location. The different release time can be attached by adding other materials that have different dissolve rate.

In certain embodiments, the reagent concentration mixed in the sample can be controlled by controlling the sample thickness (e.g. control the ratio of the sample thickness to the storage site area and/or the mixing time).

2. Plates, Spacers, Scale-Marks, Sample Thickness Regulation 2.1 Plate Configurations and Sample Thickness Regulation Open Configuration.

In some embodiments, in the open configuration, the two plates (i.e. the first plate and the second plate) are separated from each other. In certain embodiments, the two plates have one side connected together during all operations of the plates (including the open and closed configuration), the two plates open and close similar to a book. In some embodiments, the two plates have rectangle (or square) shape and have two sides of the rectangle connected together during all operations of the plates.

In some embodiments, the open configuration comprises a configuration that the plates are far away from each other, so that the sample is deposited onto one plate of the pair without a hindrance of the other plate of the pair.

In some embodiments, the open configuration comprises a configuration that the plates are far way, so that the sample is directly deposited onto one plate, as if the other plate does not exist.

In some embodiments, the open configuration comprises a configuration that the pair of the plates are spaced apart by a distance at least 10 nm, at least 100 nm, at least 1000 nm, at least 0.01 cm, at least 0.1 cm, at least 0.5 cm, at least 1 cm, at least 2 cm, or at least 5 cm, or a range of any two of the values.

In some embodiments, the open configuration comprises a configuration that the pair of plates are oriented in different orientations. In some embodiments, the open configuration comprises a configuration that defines an access gap between the pair of plates that is configured to permit sample addition.

In some embodiments, the open configuration comprises a configuration, wherein each plate has a sample contact surface and wherein at least one of the contact surfaces of the plates is exposed when the plates are in the one open configuration.

Closed Configuration and Sample Thickness Regulation.

In present invention, a closed configuration of the two plates is the configuration that a spacing (i.e. the distance) between the inner surfaces of the two plates is regulated by the spacers between the two plates. Since the inner surfaces (also termed "sample surface") of the plates are in contact with the sample during the compression step of a CROF process, hence at the closed configuration, the sample thickness is regulated by the spacers.

During the process of bring the plates from an open configuration to a closed configuration, the plates are facing each other (at least a part of the plates are facing each other) and a force is used to bring the two plates together. When the two plates are brought from an open configuration to a closed configuration, the inner surfaces of the two plate compress the sample deposited on the plate(s) to reduce the sample thickness (while the sample has an open flow laterally between the plates), and the thickness of a relevant volume of the sample is determined by the spacers, the plates, and the method being used and by the sample mechanical/fluidic property. The thickness at a closed configuration can be predetermined for a given sample and given spacers, plates and plate pressing method.

The term "regulation of the spacing between the inner surfaces of the plates by the spacers" or "the regulation of the sample thickness by the plates and the spacer", or a thickness of the sample is regulated by the spacers and the plates" means that the thickness of the sample in a CROF process is determined by a given plates, spacers, sample, and pressing method.

In some embodiments, the regulated sample thickness at the closed configuration is the same as the height of a spacer; in this case, at the closed configuration, the spacers directly contact both plates (wherein one plate is the one that the spacer is fixed on, and the other plate is the plate that is brought to contact with the spacer).

In certain embodiments, the regulated sample thickness at the closed configuration is larger than the height of a spacer; in this case, at the closed configuration, the spacers directly contacts only the plate that has the spacers fixed or attached on its surface, and indirectly contact the other plate (i.e. indirect contact). The term "indirect contact" with a plate means that the spacer and the plate is separated by a thin sample layer, which is termed "residual sample layer" and its thickness is termed "the residue thickness". For given spacers and plates, a given plate pressing method, and a given sample, the residual thickness can be predetermined (pre-determined means prior to reach the closed configuration), leading to a predetermination of the sample thickness at the closed configuration. This is because the residue layer thickness is the same for the given conditions (the sample, spacers, plates, and pressing force) and can be pre-calibrated and/or calculated. The regulated sample thickness is approximately equal to the spacer height plus the sample residue thickness.

In many embodiments, the size and shape of the pillars are pre-characterized (i.e. pre-determined) before their use. And the pre-determined information are used to for later assaying, such as determination of the sample volume (or relevant volume) and others.

In some embodiments, the regulating of the sample thickness includes applying a closing (compression) force to the plates to maintain the spacing between the plates.

In some embodiments, the regulating of the sample thickness includes establishing the spacing between the plates with the spacers, a closing force applied to the plates, and physical properties of the sample, and optionally wherein the physical properties of the sample include at least one of viscosity and compressibility.

2.2 Plates

In present invention, generally, the plates of CROF are made of any material that (i) is capable of being used to regulate, together with the spacers, the thickness of a portion or entire volume of the sample, and (ii) has no significant adverse effects to a sample, an assay, or a goal that the plates intend to accomplish. However, in certain embodiments, particular materials (hence their properties) are used for the plate to achieve certain objectives.

In some embodiments, the two plates have the same or different parameters for each of the following parameters: plate material, plate thickness, plate shape, plate area, plate flexibility, plate surface property, and plate optical transparency.

Plate Materials.

The plates are made a single material, composite materials, multiple materials, multilayer of materials, alloys, or a combination thereof. Each of the materials for the plate is an inorganic material, am organic material, or a mix, wherein examples of the materials are given in paragraphs of Mat-1 and Mat-2.

Mat-1. The inorganic materials for the plates include, not limited to, glass, quartz, oxides, silicon-dioxide, silicon-nitride, hafnium oxide (HfO), aluminum oxide (A1O), semi-conductors: (silicon, GaAs, GaN, etc.), metals (e.g. gold, silver, cooper, aluminum, Ti, Ni, etc.), ceramics, or any combinations of thereof.

Mat-2 The organic materials for the spacers include, not limited to, polymers (e.g. plastics) or amorphous organic materials. The polymer materials for the spacers include, not limited to, acrylate polymers, vinyl polymers, olefin polymers, cellulosic polymers, noncellulosic polymers, polyester polymers, Nylon, cyclic olefin copolymer (COC), poly (methyl methacrylate) (PMMA), polycarbonate (PC), cyclic olefin polymer (COP), liquid crystalline polymer (LCP), polyamide (PA), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFA), polydimethylsiloxane (PDMS), rubbers, or any combinations of thereof.

In some embodiments, the plates are each independently made of at least one of glass, plastic, ceramic, and metal. In some embodiments, each plate independently includes at least one of glass, plastic, ceramic, and metal.

In some embodiments, one plate is different from the other plate in lateral area, thickness, shape, materials, or surface treatment. In some embodiments, one plate is the same as the other plate in lateral area, thickness, shape, materials, or surface treatment.

The materials for the plates are rigid, flexible or any flexibility between the two. The rigid (i.e. stiff) or flexibility is relative to a give pressing forces used in bringing the plates into the closed configuration.

In some embodiments, a selection of rigid or flexible plate are determined from the requirements of controlling a uniformity of the sample thickness at the closed configuration.

In some embodiments, at least one of the two plates are transparent (to a light). In some embodiments at least a part or several parts of one plate or both plates are transparent. In some embodiments, the plates are non-transparent.

Plate Thickness.

In some embodiments, the average thicknesses for at least one of the pates are 2 nm or less, 10 nm or less, 100 nm or less, 500 nm or less, 1000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, or a range between any two of the values.

In some embodiments, the average thicknesses for at least one of the plates are at most 3 mm (millimeter), at most 5 mm, at most 10 mm, at most 20 mm, at most 50 mm, at most 100 mm, at most 500 mm, or a range between any two of the values.

In some embodiments, the thickness of a plate is not uniform across the plate. Using a different plate thickness at different location can be used to control the plate bending, folding, sample thickness regulation, and others.

Plate Shape and Area.

Generally, the plates can have any shapes, as long as the shape allows a compress open flow of the sample and the regulation of the sample thickness. However, in certain embodiments, a particular shape may be advantageous. The shape of the plate can be round, elliptical, rectangles, triangles, polygons, ring-shaped, or any superpositions of these shapes.

In some embodiments, the two plates can have the same size or shape, or different. The area of the plates depend on the application. The area of the plate is at most 1 mm2 (millimeter square), at most 10 mm2, at most 100 mm2, at most 1 cm2 (centimeter square), at most 5 cm2, at most 10 cm2, at most 100 cm2, at most 500 cm2, at most 1000 cm2, at most 5000 cm2, at most 10,000 cm2, or over 10,000 cm2, or any arrange between any of the two values. The shape of the plate can be rectangle, square, round, or others.

In certain embodiments, at least one of the plate is in the form of a belt (or strip) that has a width, thickness, and length. The width is at most 0.1 cm (centimeter), at most 0.5 cm, at most 1 cm, at most 5 cm, at most 10 cm, at most 50 cm, at most 100 cm, at most 500 cm, at most 1000 cm, or a range between any two of the values. The length can be as long it needed. The belt can be rolled into a roll.

Plate Surface Flatness.

In many embodiments, an inner surface of the plates are flat or significantly flat, planar. In certain embodiments, the two inner surfaces are, at the closed configuration, parallel with each other. Flat inner surfaces facilitates a quantification and/or controlling of the sample thickness by simply using the predetermined spacer height at the closed configuration. For non-flat inner surfaces of the plate, one need to know not only the spacer height, but also the exact the topology of the inner surface to quantify and/or control the sample thickness at the closed configuration. To know the surface topology needs additional measurements and/or corrections, which can be complex, time consuming, and costly.

A flatness of the plate surface is relative to the final sample thickness (the final thickness is the thickness at the closed configuration), and is often characterized by the term of "relative surface flatness" is the ratio of the plate surface flatness variation to the final sample thickness.

In some embodiments, the relative surface is less than 0.01%, 0.1%, less than 0.5%, less than 1%, less than 2%, less than 5%, less than 10%, less than 20%, less than 30%, less than 50%, less than 70%, less than 80%, less than 100%, or a range between any two of these values.

Plate Surface Parallelness.

In some embodiments, the two surfaces of the plate is significantly parallel with each other. In certain embodiments, the two surfaces of the plate is not parallel with each other.

Plate Flexibility.

In some embodiments, a plate is flexible under the compressing of a CROF process. In some embodiments, both plates are flexible under the compressing of a CROF process. In some embodiments, a plate is rigid and another plate is flexible under the compressing of a CROF process. In some embodiments, both plates are rigid. In some embodiments, both plate are flexible but have different flexibility.

Plate Optical Transparency.

In some embodiments, a plate is optical transparent. In some embodiments, both plates are optical transparent. In some embodiments, a plate is optical transparent and another plate is opaque. In some embodiments, both plates are opaque. In some embodiments, both plate are optical transparent but have different optical transparency. The optical transparency of a plate refers a part or the entire area of the plate.

Surface Wetting Properties.

In some embodiments, a plate has an inner surface that wets (i.e. contact angle is less 90 degree) the sample, the transfer liquid, or both. In some embodiments, both plates have an inner surface that wets the sample, the transfer liquid, or both; either with the same or different wettability. In some embodiments, a plate has an inner surface that wets the sample, the transfer liquid, or both; and another plate has an inner surface that does not wet (i.e. the contact angle equal to or larger than 90 degree). The wetting of a plate inner surface refers a part or the entire area of the plate.

In some embodiments, the inner surface of the plate has other nano or microstructures to control a lateral flow of a sample during a CROF. The nano or microstructures include, but not limited to, channels, pumps, and others. Nano and microstructures are also used to control the wetting properties of an inner surface.

2.3 Spacers

Spacers' Function.

In present invention, the spacers are configured to have one or any combinations of the following functions and properties: the spacers are configured to (1) control, together with the plates, the thickness of the sample or a relevant volume of the sample (Preferably, the thickness control is precise, or uniform or both, over a relevant area); (2) allow the sample to have a compressed regulated open flow (CROF) on plate surface; (3) not take significant surface area (volume) in a given sample area (volume); (4) reduce or increase the effect of sedimentation of particles or analytes in the sample; (5) change and/or control the wetting propertied of the inner surface of the plates; (6) identify a location of the plate, a scale of size, and/or the information related to a plate, or (7) do any combination of the above.

Spacer Architectures and Shapes.

To achieve desired sample thickness reduction and control, in certain embodiments, the spacers are fixed its respective plate. In general, the spacer can have any shape, as long as the spacers are capable of regulating the sample thickness during a CROF process, but certain shapes are preferred to achieve certain functions, such as better uniformity, less overshoot in pressing, etc.

The spacer(s) is a single spacer or a plurality of spacers. (e.g. an array). Some embodiments of a plurality of spacers is an array of spacers (e.g. pillars), where the inter-spacer distance is periodic or aperiodic, or is periodic or aperiodic in certain areas of the plates, or has different distances in different areas of the plates.

There are two kinds of the spacers: open-spacers and enclosed-spacers. The open-spacer is the spacer that allows a sample to flow through the spacer (i.e. the sample flows around and pass the spacer. For example, a post as the spacer.), and the enclosed spacer is the spacer that stop the sample flow (i.e. the sample cannot flow beyond the spacer. For example, a ring shape spacer and the sample is inside the ring.). Both types of spacers use their height to regular the final sample thickness at a closed configuration.

In some embodiments, the spacers are open-spacers only. In some embodiments, the spacers are enclosed-spacers only. In some embodiments, the spacers are a combination of open-spacers and enclosed-spacers.

The term "pillar spacer" means that the spacer has a pillar shape and the pillar shape refers to an object that has height and a lateral shape that allow a sample to flow around it during a compressed open flow.

In some embodiments, the lateral shapes of the pillar spacers are the shape selected from the groups of (i) round, elliptical, rectangles, triangles, polygons, ring-shaped, star-shaped, letter-shaped (e.g. L-shaped, C-shaped, the letters from A to Z), number shaped (e.g. the shapes like 0, 1, 2, 3, 4, . . . to 9); (ii) the shapes in group (i) with at least one rounded corners; (iii) the shape from group (i) with zig-zag or rough edges; and (iv) any superposition of (i), (ii) and (iii). For multiple spacers, different spacers can have different lateral shape and size and different distance from the neighboring spacers.

In some embodiments, the spacers may be and/or may include posts, columns, beads, spheres, and/or other suitable geometries. The lateral shape and dimension (i.e., transverse to the respective plate surface) of the spacers can be anything, except, in some embodiments, the following restrictions: (i) the spacer geometry will not cause a significant error in measuring the sample thickness and volume; or (ii) the spacer geometry would not prevent the out-flowing of the sample between the plates (i.e. it is not in enclosed form). But in some embodiments, they require some spacers to be closed spacers to restrict the sample flow.

In some embodiments, the shapes of the spacers have rounded corners. For example, a rectangle shaped spacer has one, several or all corners rounded (like a circle rather 90 degree angle). A round corner often make a fabrication of the spacer easier, and in some cases less damage to a biological material.

The sidewall of the pillars can be straight, curved, sloped, or different shaped in different section of the sidewall. In some embodiments, the spacers are pillars of various lateral shapes, sidewalls, and pillar-height to pillar lateral area ratio.

In a preferred embodiment, the spacers have shapes of pillars for allowing open flow.

Spacers' Materials.

In the present invention, the spacers are generally made of any material that is capable of being used to regulate, together with the two plates, the thickness of a relevant volume of the sample. In some embodiments, the materials for the spacers are different from that for the plates. In some embodiments, the materials for the spaces are at least the same as a part of the materials for at least one plate.

The spacers are made a single material, composite materials, multiple materials, multilayer of materials, alloys, or a combination thereof. Each of the materials for the spacers is an inorganic material, am organic material, or a mix, wherein examples of the materials are given in paragraphs of Mat-1 and Mat-2. In a preferred embodiment, the spacers are made in the same material as a plate used in CROF.

Spacer's Mechanical Strength and Flexibility.

In some embodiments, the mechanical strength of the spacers are strong enough, so that during the compression and at the closed configuration of the plates, the height of the spacers is the same or significantly same as that when the plates are in an open configuration. In some embodiments, the differences of the spacers between the open configuration and the closed configuration can be characterized and predetermined.

The material for the spacers is rigid, flexible or any flexibility between the two. The rigid is relative to a give pressing forces used in bringing the plates into the closed configuration: if the space does not deform greater than 1% in its height under the pressing force, the spacer material is regarded as rigid, otherwise a flexible. When a spacer is made of material flexible, the final sample thickness at a closed configuration still can be predetermined from the pressing force and the mechanical property of the spacer.

Spacer Inside Sample.

To achieve desired sample thickness reduction and control, particularly to achieve a good sample thickness uniformity, in certain embodiments, the spacers are placed inside the sample, or the relevant volume of the sample. In some embodiments, there are one or more spacers inside the sample or the relevant volume of the sample, with a proper inter spacer distance. In certain embodiments, at least one of the spacers is inside the sample, at least two of the spacers inside the sample or the relevant volume of the sample, or at least of "n" spacers inside the sample or the relevant volume of the sample, where "n" may be determined by a sample thickness uniformity or a required sample flow property during a CROF.

Spacer Height.

In some embodiments, all spacers have the same pre-determined height. In some embodiments, spacers have different pre-determined height. In some embodiments, spacers can be divided into groups or regions, wherein each group or region has its own spacer height. And in certain embodiments, the predetermined height of the spacers is an average height of the spacers. In some embodiments, the spacers have approximately the same height. In some embodiments, a percentage of number of the spacers have the same height.

The height of the spacers is selected by a desired regulated final sample thickness and the residue sample thickness. The spacer height (the predetermined spacer height) and/or sample thickness is 3 nm or less, 10 nm or less, 50 nm or less, 100 nm or less, 200 nm or less, 500 nm or less, 800 nm or less, 1000 nm or less, 1 µm or less, 2 µm or less, 3 µm or less, 5 µm or less, 10 µm or less, 20 µm or less, 30 µm or less, 50 µm or less, 100 µm or less, 150 µm or less, 200 µm or less, 300 µm or less, 500 µm or less, 800 µm or less, 1 mm or less, 2 mm or less, 4 mm or less, or a range between any two of the values.

The spacer height and/or sample thickness is between 1 nm to 100 nm in one preferred embodiment, 100 nm to 500 nm in another preferred embodiment, 500 nm to 1000 nm in a separate preferred embodiment, 1 µm (i.e. 1000 nm) to 2 µm in another preferred embodiment, 2 µm to 3 µm in a separate preferred embodiment, 3 µm to 5 µm in another preferred embodiment, 5 µm to 10 µm in a separate preferred embodiment, and 10 µm to 50 µm in another preferred embodiment, 50 µm to 100 µm in a separate preferred embodiment.

In some embodiments, the spacer height and/or sample thickness (i) equal to or slightly larger than the minimum dimension of an analyte, or (ii) equal to or slightly larger than the maximum dimension of an analyte. The "slightly larger" means that it is about 1% to 5% larger and any number between the two values.

In some embodiments, the spacer height and/or sample thickness is larger than the minimum dimension of an analyte (e.g. an analyte has an anisotropic shape), but less than the maximum dimension of the analyte.

For example, the red blood cell has a disk shape with a minim dimension of 2 μm (disk thickness) and a maximum dimension of 11 μm (a disk diameter). In an embodiment of the present invention, the spacers is selected to make the inner surface spacing of the plates in a relevant area to be 2 μm (equal to the minimum dimension) in one embodiment, 2.2 μm in another embodiment, or 3 (50% larger than the minimum dimension) in other embodiment, but less than the maximum dimension of the red blood cell. Such embodiment has certain advantages in blood cell counting. In one embodiment, for red blood cell counting, by making the inner surface spacing at 2 or 3 μm and any number between the two values, a undiluted whole blood sample is confined in the spacing, on average, each red blood cell (RBC) does not overlap with others, allowing an accurate counting of the red blood cells visually. (Too many overlaps between the RBC's can cause serious errors in counting).

In the present invention, in some embodiments, it uses the plates and the spacers to regulate not only a thickness of a sample, but also the orientation and/or surface density of the analytes/entity in the sample when the plates are at the closed configuration. When the plates are at a closed configuration, a thinner thickness of the sample gives a less the analytes/entity per surface area (i.e. less surface concentration).

Spacer Lateral Dimension.

For an open-spacer, the lateral dimensions can be characterized by its lateral dimension (sometime being called width) in the x and y-two orthogonal directions. The lateral dimension of a spacer in each direction is the same or different. In some embodiments, the lateral dimension for each direction (x or y) is . . . .

In some embodiments, the ratio of the lateral dimensions of x to y direction is 1, 1.5, 2, 5, 10, 100, 500, 1000, 10,000, or a range between any two of the value. In some embodiments, a different ratio is used to regulate the sample flow direction; the larger the ratio, the flow is along one direction (larger size direction).

In some embodiments, the different lateral dimensions of the spacers in x and y direction are used as (a) using the spacers as scale-markers to indicate the orientation of the plates, (b) using the spacers to create more sample flow in a preferred direction, or both.

In a preferred embodiment, the period, width, and height.

In some embodiments, all spacers have the same shape and dimensions. In some embodiments, each spacers have different lateral dimensions.

For enclosed-spacers, in some embodiments, the inner lateral shape and size are selected based on the total volume of a sample to be enclosed by the enclosed spacer(s), wherein the volume size has been described in the present disclosure; and in certain embodiments, the outer lateral shape and size are selected based on the needed strength to support the pressure of the liquid against the spacer and the compress pressure that presses the plates.

Aspect Ratio of Height to the Average Lateral Dimension of Pillar Spacer.

In certain embodiments, the aspect ratio of the height to the average lateral dimension of the pillar spacer is 100,000, 10,000, 1,000, 100, 10, 1, 0.1, 0.01, 0.001, 0.0001, 0, 00001, or a range between any two of the values.

Spacer Height Precisions.

The spacer height should be controlled precisely. The relative precision of the spacer (i.e. the ratio of the deviation to the desired spacer height) is 0.001% or less, 0.01% or less, 0.1% or less; 0.5% or less, 1% or less, 2% or less, 5% or less, 8% or less, 10% or less, 15% or less, 20% or less, 30% or less, 40% or less, 50% or less, 60% or less, 70% or less, 80% or less, 90% or less, 99.9% or less, or a range between any of the values.

Inter-Spacer Distance.

The spacers can be a single spacer or a plurality of spacers on the plate or in a relevant area of the sample. In some embodiments, the spacers on the plates are configured and/or arranged in an array form, and the array is a periodic, non-periodic array or periodic in some locations of the plate while non-periodic in other locations.

In some embodiments, the periodic array of the spacers has a lattice of square, rectangle, triangle, hexagon, polygon, or any combinations of thereof, where a combination means that different locations of a plate has different spacer lattices.

In some embodiments, the inter-spacer distance of a spacer array is periodic (i.e. uniform inter-spacer distance) in at least one direction of the array. In some embodiments, the inter-spacer distance is configured to improve the uniformity between the plate spacing at a closed configuration.

The distance between neighboring spacers (i.e. the inter-spacer distance) is 1 μm or less, 5 μm or less, 10 μm or less, 20 μm or less, 30 μm or less, 40 μm or less, 50 μm or less, 60 μm or less, 70 μm or less, 80 μm or less, 90 μm or less, 100 μm or less, 200 μm or less, 300 μm or less, 400 μm or less, or a range between any two of the values.

In certain embodiments, the inter-spacer distance is at 400 or less, 500 or less, 1 mm or less, 2 mm or less, 3 mm or less, 5 mm or less, 7 mm or less, 10 mm or less, or any range between the values. In certain embodiments, the inter-spacer distance is a 10 mm or less, 20 mm or less, 30 mm or less, 50 mm or less, 70 mm or less, 100 mm or less, or any range between the values.

The distance between neighboring spacers (i.e. the inter-spacer distance) is selected so that for a given properties of the plates and a sample, at the closed-configuration of the plates, the sample thickness variation between two neighboring spacers is, in some embodiments, at most 0.5%, 1%, 5%, 10%, 20%, 30%, 50%, 80%, or any range between the values; or in certain embodiments, at most 80%, 100%, 200%, 400%, or a range between any two of the values.

Clearly, for maintaining a given sample thickness variation between two neighboring spacers, when a more flexible plate is used, a closer inter-spacer distance is needed.

Specify the accuracy of the inter spacer distance.

In a preferred embodiment, the spacer is a periodic square array, wherein the spacer is a pillar that has a height of 2 to 4 μm, an average lateral dimension of from 5 to 20 μm, and inter-spacer spacing of 1 μm to 100 μm.

In a preferred embodiment, the spacer is a periodic square array, wherein the spacer is a pillar that has a height of 2 to 4 μm, an average lateral dimension of from 5 to 20 μm, and inter-spacer spacing of 100 μm to 250 μm.

In a preferred embodiment, the spacer is a periodic square array, wherein the spacer is a pillar that has a height of 4 to 50 μm, an average lateral dimension of from 5 to 20 μm, and inter-spacer spacing of 1 μm to 100 μm.

In a preferred embodiment, the spacer is a periodic square array, wherein the spacer is a pillar that has a height of 4 to 50 μm, an average lateral dimension of from 5 to 20 μm, and inter-spacer spacing of 100 μm to 250 μm.

The period of spacer array is between 1 nm to 100 nm in one preferred embodiment, 100 nm to 500 nm in another preferred embodiment, 500 nm to 1000 nm in a separate preferred embodiment, 1 μm (i.e. 1000 nm) to 2 μm in another preferred embodiment, 2 μm to 3 μm in a separate preferred embodiment, 3 μm to 5 μm in another preferred embodiment, 5 μm to 10 μm in a separate preferred embodiment, and 10 μm to 50 μm in another preferred embodiment, 50 μm to 100 μm in a separate preferred embodiment, 100 μm to 175 μm in a separate preferred embodiment, and 175 μm to 300 μm in a separate preferred embodiment.

Spacer Density.

The spacers are arranged on the respective plates at a surface density of greater than one per $\mu m^2$, greater than one per 10 $\mu m^2$, greater than one per 100 $\mu m^2$, greater than one per 500 $\mu m^2$, greater than one per 1000 $\mu m^2$, greater than one per 5000 $\mu m^2$, greater than one per 0.01 $mm^2$, greater than one per 0.1 $mm^2$, greater than one per 1 $mm^2$, greater than one per 5 $mm^2$, greater than one per 10 $mm^2$, greater than one per 100 $mm^2$, greater than one per 1000 $mm^2$, greater than one per 10000 $mm^2$, or a range between any two of the values.

(3) the spacers are configured to not take significant surface area (volume) in a given sample area (volume);

Ratio of Spacer Volume to Sample Volume.

In many embodiments, the ratio of the spacer volume (i.e. the volume of the spacer) to sample volume (i.e. the volume of the sample), and/or the ratio of the volume of the spacers that are inside of the relevant volume of the sample to the relevant volume of the sample are controlled for achieving certain advantages. The advantages include, but not limited to, the uniformity of the sample thickness control, the uniformity of analytes, the sample flow properties (i.e. flow speed, flow direction, etc.).

In certain embodiments, the ratio of the spacer volume r) to sample volume, and/or the ratio of the volume of the spacers that are inside of the relevant volume of the sample to the relevant volume of the sample is less than 100%, at most 99%, at most 70%, at most 50%, at most 30%, at most 10%, at most 5%, at most 3% at most 1%, at most 0.1%, at most 0.01%, at most 0.001%, or a range between any of the values.

Spacers Fixed to Plates.

The inter spacer distance and the orientation of the spacers, which play a key role in the present invention, are preferably maintained during the process of bringing the plates from an open configuration to the closed configuration, and/or are preferably predetermined before the process from an open configuration to a closed configurations.

Some embodiments of the present invention is that the spacers are fixed on one of the plates before bring the plates to the closed configuration. The term "a spacer is fixed with its respective plate" means that the spacer is attached to a plate and the attachment is maintained during a use of the plate. An example of "a spacer is fixed with its respective plate" is that a spacer is monolithically made of one piece of material of the plate, and the position of the spacer relative to the plate surface does not change. An example of "a spacer is not fixed with its respective plate" is that a spacer is glued to a plate by an adhesive, but during a use of the plate, the adhesive cannot hold the spacer at its original location on the plate surface (i.e. the spacer moves away from its original position on the plate surface).

In some embodiments, at least one of the spacers are fixed to its respective plate. In certain embodiments, at two spacers are fixed to its respective plates. In certain embodiments, a majority of the spacers are fixed with their respective plates. In certain embodiments, all of the spacers are fixed with their respective plates.

In some embodiments, a spacer is fixed to a plate monolithically.

In some embodiments, the spacers are fixed to its respective plate by one or any combination of the following methods and/or configurations: attached to, bonded to, fused to, imprinted, and etched.

The term "imprinted" means that a spacer and a plate are fixed monolithically by imprinting (i.e. embossing) a piece of a material to form the spacer on the plate surface. The material can be single layer of a material or multiple layers of the material.

The term "etched" means that a spacer and a plate are fixed monolithically by etching a piece of a material to form the spacer on the plate surface. The material can be single layer of a material or multiple layers of the material.

The term "fused to" means that a spacer and a plate are fixed monolithically by attaching a spacer and a plate together, the original materials for the spacer and the plate fused into each other, and there is clear material boundary between the two materials after the fusion.

The term "bonded to" means that a spacer and a plate are fixed monolithically by binding a spacer and a plate by adhesion.

The term "attached to" means that a spacer and a plate are connected together.

In some embodiments, the spacers and the plate are made in the same materials. In other embodiment, the spacers and the plate are made from different materials. In other embodiment, the spacer and the plate are formed in one piece. In other embodiment, the spacer has one end fixed to its respective plate, while the end is open for accommodating different configurations of the two plates.

In other embodiment, each of the spacers independently is at least one of attached to, bonded to, fused to, imprinted in, and etched in the respective plate. The term "independently" means that one spacer is fixed with its respective plate by a same or a different method that is selected from the methods of attached to, bonded to, fused to, imprinted in, and etched in the respective plate.

In some embodiments, at least a distance between two spacers is predetermined ("predetermined inter-spacer distance" means that the distance is known when a user uses the plates.).

In some embodiments of all methods and devices described herein, there are additional spacers besides to the fixed spacers.

Specific Sample Thickness.

In present invention, it was observed that a larger plate holding force (i.e. the force that holds the two plates together) can be achieved by using a smaller plate spacing (for a given sample area), or a larger sample area (for a given plate-spacing), or both.

In some embodiments, at least one of the plates is transparent in a region encompassing the relevant area, each plate has an inner surface configured to contact the sample in the closed configuration; the inner surfaces of the plates are substantially parallel with each other, in the closed configuration; the inner surfaces of the plates are substantially planar, except the locations that have the spacers; or any combination of thereof.

2.4 Final Sample Thickness and Uniformity

In some embodiments, significantly flat is determined relative to the final sample thickness, and has, depending upon on embodiments and applications, a ratio of to the sample thickness of less than 0.1%, less than 0.5%, less than 1%, less than 2%, less than 5%, or less than 10%, or a range between any two of these values.

In some embodiments, flatness relative to the sample thickness may be less than 0.1%, less than 0.5%, less than 1%, less than 2%, less than 5%, less than 10%, less than 20%, less than 50%, or less than 100%, or a range between any two of these values.

In some embodiments, significantly flat may mean that the surface flatness variation itself (measured from an average thickness) is less than 0.1%, less than 0.5%, less than 1%, less than 2%, less than 5%, or less than 10%, or a range between any two of these values. Generally, flatness relative to the plate thickness may be less than 0.1%, less than 0.5%, less than 1%, less than 2%, less than 5%, less than 10%, less than 20%, less than 50%, or less than 100%, or a range between any two of these values.

2.5 Spacer Fabrication Methods.

The spacers can be fabricated on a plate in a variety of ways, using lithography, etching, embossing (nanoimprint), depositions, lift-off, fusing, or a combination of thereof. In some embodiments, the spacers are directly embossed or imprinted on the plates. In some embodiments, the spacers imprinted into a material (e.g. plastics) that is deposited on the plates. In certain embodiments, the spacers are made by directly embossing a surface of a CROF plate. The nanoimprinting may be done by roll to roll technology using a roller imprinter, or roll to a planar nanoimprint. Such process has a great economic advantage and hence lowering the cost.

In some embodiments, the spacers are deposited on the plates. The deposition can be evaporation, pasting, or a lift-off. In the pasting, the spacer is fabricated first on a carrier, then the spacer is transferred from the carrier to the plate. In the lift-off, a removable material is first deposited on the plate and holes are created in the material; the hole bottom expose the plate surface and then a spacer material is deposited into the hole and afterwards the removable material is removed, leaving only the spacers on the plate surface. In some embodiments, the spacers deposited on the plate are fused with the plate. In some embodiments, the spacer and the plates are fabricated in a single process. The single process includes imprinting (i.e. embossing, molding) or synthesis.

In some embodiments, at least two of the spacers are fixed to the respective plate by different fabrication methods, and optionally wherein the different fabrication methods include at least one of being deposition, bonded, fuse, imprinted, and etched.

In some embodiments, one or more of the spacers are fixed to the respective plate(s) is by a fabrication method of being bonded, being fused, being imprinted, or being etched, or any combination of thereof.

In some embodiments, the fabrication methods for forming such monolithic spacers on the plate include a method of being bonded, being fused, being imprinted, or being etched, or any combination of thereof.

2.6 Scale-Markers

The term "scale-marker(s) refers to the scale-marker(s) that able to assist a quantification (i.e. dimension measurement) or a control of the relevant area and/or the relative volume of a sample. In some embodiments, the scale-markers are on the first plate or the second plate, on both on plates, on one surface of the plate, on both surfaces of the plate, between the plates, near the plates, or any combination of thereof. In some embodiments, the scale-markers are fixed on the first plate or the second plate, on both on plates, on one surface of the plate, on both surfaces of the plate, between the plates, near the plates, or any combination of thereof. In some embodiments, the scale-markers are deposited on the first plate or the second plate, on both on plates, on one surface of the plate, on both surfaces of the plate, between the plates, near the plates, or any combination of thereof. In some embodiments, some of spacers are fixed and some spacers are deposited.

In some embodiments, the scale-marks are etched scale-marks, deposited materials, or printed materials. In certain embodiments, the materials that absorbing the light, reflecting light, emitting light, or any combination of thereof.

In some embodiments, the scale-markers are a or a plurality of object(s) with known dimensions and/or known separation distances. Examples of the objects include, not limited to, rectangles, cylinders, or circles.

In some embodiments, the scale-markers have a dimension of in the range of nanometers (nm), microns (µm) or millimeters (mm) or other sizes.

In some embodiments, the scale-markers are a ruler, which has scale scale-marks that are configured to measure a dimension of an object. In some embodiments, the scale-marks are in the scale of nanometer (nm), microns (µm) or millimeter (mm) or other sizes. In some embodiments, the scale marks are etched scale-marks, deposited materials, or printed materials. In some embodiments, the materials for the scale-markers are the materials that absorbing the light, reflecting light, scattering light, interfering light, diffracting light, emitting light, or any combination of thereof.

In some embodiments, the makers are the spacers, which server dual functions of "regulating sample thickness" and "providing scale-marking and/or dimension scaling". For examples, a rectangle spacer with a known dimension or two spacers with a known separation distance can be used to measure a dimension related to the sample round the spacer (s). From the measured sample dimension, one can calculate the volume of the relevant volume of the sample.

In some embodiments, the scale-markers is configured to at least partially define a boundary of the relevant volume of the sample.

In some embodiments, at least one of the scale-markers is configured to have a known dimension that is parallel to a plane of the lateral area of the relevant volume of the sample.

In some embodiments, at least a pair of the scale-markers are separated by a known distance that is parallel to a plane of the lateral area.

In some embodiments, the scale-markers are configured for optical detection.

In some embodiments, each scale-marker independently is at least one of light absorbing, light reflecting, light scattering, light diffracting, and light emitting.

In some embodiments, the scale-markers are arranged in a regular array with a known lateral spacing.

In some embodiments, each scale-marker independently has a lateral profile that is at least one of square, rectangular, polygonal, and circular.

In some embodiments, at least one of the scale-markers is attached to, bonded to, fused to, imprinted in, and etched in one of the plates.

In some embodiments, at least one of the scale-markers is one of the spacers.

In some embodiments, some spacers also play a role of scale-marker to quantification of a relevant volume of the sample.

In certain embodiments, a binding site(s) (that immobilizes the analytes), storage sites, or alike, serves as a scale-marker(s). In one embodiment, the site with a known lateral dimension interacts with light generating a detectable signal, that reals the known lateral dimension of the site, hence serving a scale-marker(s).

In another embodiment, the dimension of the sites are predetermined before a CROF process and the thickness of the portion of the sample sitting on the site is, when the plates are at the closed configuration, significantly smaller than the lateral average dimension of the site, then by controlling the incubation time so that, after the incubation, (1) the majority of the analytes/entity that bind to the binding site come from the sample volume that sites on top of the binding site, or (2) the majority of the reagent that is mixed (diffused) into the sample volume that sites on top of the binding site come from the storage site. In these cases, the relevant volume of the sample to the binding or the reagent mixing is the volume that is approximately equal to the predetermined site area multiplies the sample thickness at the site. A key reason for this be possible is that, for the given incubation time, the analytes/entity in the sample volume outside the relevant volume do not have enough time to diffuse into the binding site, or the reagents on the storage site do not have enough time to diffuse into in the sample volume outside the relevant volume.

An example to illustrate the method of measuring and/or controlling the relevant area and volume by using a site with known dimension and by limiting the incubation time is that an assay has a binding site (i.e. the area with capture agents) of 1,000 μm by 1000 μm on a first plate of a CROF process (which has a surface large than the binding site); at the closed configuration of the plates, a sample with analytes is over the binding site, has a thickness of about 20 μm (in the bind site area) and an area larger than the binding site and is incubated for a time equal to the target analyte/entity diffusion time across the sample thickness. In this case, the majority of the analytes/entity that bind to the binding site come from the sample volume that sites on top of the binding site, which is 1,000 μm by 1000 μm by 20 μm=0.02 p, because the analytes in the sample portion that is 20 μm away from the binding site do not have time to diffuse to the binding site (statistically). In this case, if the signal, due to the analytes/entity captured by the binding site, is measured after the incubation, one can determine the analyte/entity concentration in the relevant area and relevant volume of the sample from the information (provided by the binding site) of the relevant area and relevant volume. The analyte concentration is quantified by the number of analytes captured by the binding site divided the relevant volume.

In some embodiments, the relevant volume is approximately equal to the binding site area times the sample thickness, and the target analyte concentration in the sample is approximately equal to the number of analyte captured by the binding site divided by the relevant sample volume. This accuracy of the method of quantification of target analyte volume gets better as the ratio of the binding site dimension to the sample thickness gets larger (assuming the incubation time is about the target analyte diffusion time in the sample for a distance of the sample thickness).

Spreading Times in CROF.

In the present invention, in the methods and the devices of all paragraphs that spread the sample by two plates, the time for spreading the sample to the final thickness at a closed configuration is 0.001 sec or less, 0.01 sec, 0.1 sec, 1 sec, 5 sec, 10 sec, 20 sec, 30 sec, 60 sec, 90 sec, 100 sec, 150 sec, 200 sec, 300 sec, 500 sec, 1000 sec, or a range between any two of the values.

In the methods and the devices of all paragraphs that spread the sample by two plates, in a preferred embodiment, the time for spreading the sample to the final thickness at a closed configuration is 0.001 sec or less, 0.01 sec, 0.1 sec, 1 sec, 3 sec, 5 sec, 10 sec, 20 sec, 30 sec, 60 sec, 90 sec, 100 sec, 150 sec, or a range between any two of the values.

In the methods and the devices of all paragraphs that spread the sample by two plates, in a preferred embodiment, the time for spreading the sample to the final thickness at a closed configuration is 0.001 sec or less, 0.01 sec, 0.1 sec, 1 sec, 3 sec, 5 sec, 10 sec, 20 sec, 30 sec, 60 sec, 90 sec, or a range between any two of the values.

In the methods and the devices of all paragraphs that spread the sample by two plates, in a preferred embodiment, the time for spreading the sample to the final thickness at a closed configuration is 0.001 sec or less, 0.01 sec, 0.1 sec, 1 sec, 3 sec, 5 sec, 10 sec, 20 sec, 30 sec, or a range between any two of the values.

In the methods and the devices of all paragraphs that spread the sample by two plates, in a preferred embodiment, the time for spreading the sample to the final thickness at a closed configuration is 0.001 sec or less, 0.01 sec, 0.1 sec, 1 sec, 3 sec, 5 sec, 10 sec, or a range between any two of the values.

In the methods and the devices of all paragraphs that spread the sample by two plates, in a preferred embodiment, the time for spreading the sample to the final thickness at a closed configuration is 0.001 sec or less, 0.01 sec, 0.1 sec, 1 sec, 3 sec, or a range between any two of the values.

The embodiments and any of their combinations described in the Section 3 are applied to (i.e. are combined with) other embodiments in the entire description of the present invention.

In one preferred embodiment, the spacers are monolithically made on the X-Plate by embossing (e.g. nanoimprinting) a thin plastic film using a mold, and are made of the same materials.

In one preferred embodiment, the spacers are monolithically made on the X-Plate by embossing (e.g. nanoimprinting) a thin plastic film using a mold, and are made of the same materials, and the thickness of the X-Plate is from 50 μm to 500 μm.

In one preferred embodiment, the spacers are monolithically made on the X-Plate by embossing (e.g. nanoimprinting) a thin plastic film using a mold, and are made of the same materials, and the thickness of the X-Plate is from 50 μm to 250 μm.

In one preferred embodiment, the spacers are monolithically made on the X-Plate and are made of the same materials, and the thickness of the X-Plate is from 50 μm to 500 μm.

In one preferred embodiment, the spacers are monolithically made on the X-Plate a thin plastic film using a mold, and are made of the same materials, and the thickness of the X-Plate is from 50 μm to 250 μm.

In one preferred embodiment, the spacers are monolithically made on the X-Plate by embossing (e.g. nanoimprinting) a thin plastic film using a mold, and are made of the same materials, where the plastic film are either PMMA (polymethyl methacrylate) of PS (polystyrene).

In one preferred embodiment, the spacers are monolithically made on the X-Plate by embossing (e.g. nanoimprinting) a thin plastic film using a mold, and are made of the same materials, where the plastic film are either PMMA (polymethyl methacrylate) of PS (polystyrene) and the thickness of the X-Plate is from 50 µm to 500 µm.

In one preferred embodiment, the spacers are monolithically made on the X-Plate by embossing (e.g. nanoimprinting) a thin plastic film using a mold, and are made of the same materials, where the plastic film are either PMMA (polymethyl methacrylate) of PS (polystyrene) and the thickness of the X-Plate is from 50 µm to 250 µm.

In one preferred embodiment, the spacers are monolithically made on the X-Plate by embossing (e.g. nanoimprinting) a thin plastic film using a mold, and are made of the same materials, where the plastic film are either PMMA (polymethyl methacrylate) of PS (polystyrene), and the spacers have either a square or rectangle shape, and have the same spacer height.

In one preferred embodiment, the spacers have a square or rectangle shape (with or without round corners).

In one preferred embodiment, the spacers have square or rectangle pillars with the pillar width (spacer width in each lateral direction) between 1 µm to 200 µm; pillar period (i.e. spacer period) from 2 µm-2000 µm, and pillar height (i.e. spacer height) from 1 µm-100 µm.

In one preferred embodiment, the spacers made of PMMA or PS have square or rectangle pillars with the pillar width (spacer width in each lateral direction) between 1 µm to 200 µm; pillar period (i.e. spacer period) from 2 µm-2000 µm, and pillar height (i.e. spacer height) from 1 µm-100 µm.

In one preferred embodiment, the spacers are monolithically made on the X-Plate and are made of plastic materials, and the spacers have square or rectangle pillars with the pillar width (spacer width in each lateral direction) between 1 µm to 200 µm; pillar period (i.e. spacer period) from 2 µm-2000 µm, and pillar height (i.e. spacer height) from 1 µm-100 µm.

In one preferred embodiment, the spacers are monolithically made on the X-Plate and are made of the same materials, and the spacers have square or rectangle pillars with the pillar width (spacer width in each lateral direction) between 1 µm to 200 µm; pillar period (i.e. spacer period) from 2 µm-2000 µm, and pillar height (i.e. spacer height) from 1 µm-10 µm.

In one preferred embodiment, the spacers are monolithically made on the X-Plate and are made of the same materials selected from PS or PMMA or other plastics, and the spacers have square or rectangle pillars with the pillar width (spacer width in each lateral direction) between 1 µm to 200 µm; pillar period (i.e. spacer period) from 2 µm-2000 µm, and pillar height (i.e. spacer height) from 10 µm-50 µm.

In one preferred embodiment of a CROF device, one plate is X-Plate and the other plate is a planar thin film, wherein the thickness of at least one of the plates is in a range of from 10 µm to 250 µm; wherein the spacers are fixed on the X-Plate, and wherein the plates and the spacers can have the same materials or different materials and are made of PMMA (polymethyl methacrylate), PS (polystyrene), or a material of similar mechanical properties as PMMA or PS.

In one preferred embodiment of a CROF device, one plate is X-Plate and the other plate is a planar thin film, wherein the thickness of at least one of the plates is in a range of from 250 µm to 500 µm; wherein the spacers are fixed on the X-Plate, and wherein the plates and the spacers can have the same materials or different materials and are made of PMMA (polymethyl methacrylate), PS (polystyrene), or a material of similar mechanical properties as PMMA or PS.

In one preferred embodiment of a CROF device, one plate is X-Plate and the other plate is a planar thin film, wherein the thickness of at least one of the plates is in a range of from 10 µm to 250 µm; wherein the spacers are fixed on the X-Plate, and are an array of square or rectangle pillars with the pillar width (spacer width in each lateral direction) between 1 µm to 200 µm; pillar period (i.e. spacer period) from 2 µm-2000 µm, and pillar height (i.e. spacer height) from 1 µm-100 µm, and wherein the plates and the spacers can have the same materials or different materials and are made of PMMA (polymethyl methacrylate), PS (polystyrene), or a material of similar mechanical properties as PMMA or PS.

The "similar" in above paragraphs means that the difference in mechanical properties within 60%.

Guard Ring.

Some embodiments have a guard ring to prevent sample flow out of the plate surface. Some embodiments of the guard ring is an enclosed wall around the sample area. The wall has a height equal to the spacer height or different from the spacer height. The wall ca be a significant distance away from the sample measurement area.

The movable plates in a CROF process may include and/or may be coupled to a hinge, a stage, or some other positioning system that is configured to transition the plates between an open configuration and a closed configuration. Movable plates may be coupled together with one or more joints in a manner that leaves an opening to access the space between the plates (e.g., to insert and/or remove sample), provided that at least one of the joints and/or at least one of the plates is flexible enough to achieve the described open and closed configurations. A membrane pump is not considered to be a movable plate(s).

3. Analytes, Entity, Binding Site, Storage Site

In present invention, the entity include, but not limited to, one of a protein, an amino acid, a nucleic acid, a lipid, a carbohydrate, a metabolite, a cell, or a nanoparticle.

In some embodiments, the binding site includes a binding partner configured to bind to the respective entity.

In some embodiments, the binding site includes an entity bound to the binding site. In some embodiments, the placing the sample includes placing the sample within the binding site.

In some embodiments, the reagent includes at least one of a protein, an amino acid, a nucleic acid, a lipid, a carbohydrate, and a metabolite.

In certain embodiments, the storage site includes dried reagent.

In some embodiments, the storage site includes reagent configured to be released from the storage site upon contact with the sample.

In some embodiments, the first storage site and the second storage site are in a common storage site.

In some embodiments, the transfer media is a sample. In some embodiments, the transfer media is a liquid, wherein the reagent or the entity can be dissolved and diffuse in the liquid.

In some embodiments, a plate has multiple storage sites. In another embodiment, one storage site has multiple reagent.

Different Release Time.

In some embodiments, a plate has multiple storage sites on different locations of the plate or one storage site stores multiple reagent, and upon in touch with the sample by the storage sites, the reagents are released but released at different time for different reagents on the same storage site or reagents on different storage sites.

In some embodiments, the first reagent is configured to be released from the first storage site upon contact with the sample in a first average release time and the second reagent is configured to be released from the second storage site upon contact with the sample in a second average release time, and wherein the first average release time is less than the second average release time.

In some embodiments, the first reagent is configured to be released from the first storage site upon contact with the sample and wherein the second reagent is a bound reagent.

In some embodiments, the depositing includes binding at least one of the reagents to the respective plate.

In some embodiments, the contacting includes releasing at least one of the reagents from the respective plate.

In some embodiments, the depositing includes depositing a first reagent and a second reagent, and wherein the contacting includes releasing the first reagent before the second reagent.

In some embodiments, at least one of the plates comprises a storage site that includes a reagent that is to be added to the relevant volume of the sample.

In some embodiments, wherein the reagent includes at least one of a protein, an amino acid, a nucleic acid, a lipid, a carbohydrate, and a metabolite.

In some embodiments, the storage site includes dried reagent.

In some embodiments, the storage site includes reagent configured to be released from the storage site upon contact with the sample.

In some embodiments, the storage site is a first storage site and the reagent is a first reagent, wherein the device includes a second storage site including a second reagent that is to be added into the relevant volume of the sample, wherein the second storage site is on one of the plates.

In some embodiments, the first storage site and the second storage site are in a common storage site.

In some embodiments, the first reagent is configured to be released from the first storage site upon contact with the sample in a first average release time and the second reagent is configured to be released from the second storage site upon contact with the sample in a second average release time, and wherein the first average release time is less than the second average release time.

In some embodiments, at least one of the reagents is dried on the respective plate.

In some embodiments of a kit, at least one of the reagents is bound to the respective plate.

In some embodiments of a kit, at least one of the reagents is configured to be released from the respective plate upon contact with the sample.

In some embodiments of a kit, a first reagent is on one or both of the plates and a second reagent is on one or both of the plates, wherein the first reagent is configured to be released from the respective plate upon contact with the sample in a first average release time and the second reagent is configured to be released from the respective plate upon contact with the sample in a second average release time, and wherein the first average release time is less than the second average release time.

In some embodiments of the devices, the storage site is a first storage site and the reagent is a first reagent, wherein the device includes a second storage site including a second reagent that is to be added into the relevant volume of the sample, wherein the second storage site is on one of the plates.

4. Locally Binding or Mixing in a Portion of a Sample (P)

In some applications, it is desirable to have a binding site to capture (i.e. bind) the analytes only in a portion of a sample, not in the entire sample. It is also desirable in some cases that a reagent is added (i.e. mixed) into a port of a sample, not the entire sample. It is often desirable that there is no fluidic separation between the portion of the sample and the rest of the sample. Such requirements are preferable or necessary in certain multiplexed detections.

The present invention offers a solution to the above requirements by using a CROF method and device to reshape a sample into a ultra-thin film of a thickness, that is smaller than the lateral dimension of the portion of the sample, wherein only an analyte inside that portion of the sample will be captured, or only the portion of the sample will be mixed with a reagent. The working principle for such approach is that when the thickness of the sample is smaller than the lateral dimension of the portion of the sample, a capture of an analyte by a surface or a mixing of reagent placed on a surface can be primarily limited by the diffusion of the analytes and the reagent in the thickness direction, where the diffusion in the lateral diffusion is relatively insignificant. For example, if a sample is reshaped in to a thin film of 5 μm thick, if the portion of the sample that an analyte should be captured or a reagent should be mixed has a lateral dimension of 5 mm by 5 mm, and if the diffusion time of analyte or reagent across the 5 μm is 10 sec, then the lateral diffusion of the analyte or the reagent across the 5 mm distance is 1,000,000 sec (since the diffusion time is proportional to the square of the diffusion distance). This means that by selecting a proper ratio of the lateral dimension of the interested portion of the sample to the sample thickness, in certain time interval, the analytes captured primarily come from the sample portion interested, or the regent is mixed primarily into the portion of the sample of interest.

4.1 Locally Binding of Entity in a Portion of a Sample to a Surface (P: Volume to Surface)

P1. A method for locally bind target entities in a relevant volume of a sample to a binding site on a surface, comprising:
 (i) perform the steps of (a) to (d) in the method of paragraph X1, wherein the sample thickness at the closed configuration is significantly less than the average linear dimension of the binding site; and wherein the relevant volume is the volume of the sample that sits on the binding site when the plates are in the closed configuration;
 (ii) after (i) and while the plates are in the closed configuration, either:
  (1) incubating the sample for a relevant time length and then stopping the incubation; or
  (2) incubating the sample for a time that is equal or longer than the minimum of a relevant time length, and then assessing, within a time period that is equal or less than the maximum of the relevant length of time, the binding of target entity to in the binding site;
 wherein the relevant time length is:
 i. equal to or longer than the time that it takes for the target entity to diffuse across the thickness of the uniform thickness layer at the closed configuration; and
 ii. significantly shorter than the time that it takes the target entity to laterally diffuse across the minimum lateral dimension of the binding site;

wherein at the end of the incubation in (1) or during the assessing in (2), the majority of the target entity bound to the binding site is from a relevant volume of the sample;

wherein the incubation allows the target entity to bind to the binding site, and wherein the relevant volume is a portion of the sample that is above the binding site at the closed configuration.

The method of paragraph P2, wherein the term "the thickness of a relevant volume of the sample is significantly less than the minimum average dimension of the binding site" means that the ratio of the minimum average dimension of the binding site to the sample thickness (termed "length to thickness ratio") is at least 3, at least 5, at least 10, at least 20, at least 50, at least 100, at least 500, at least 1,000, at least 10,000, at least 100,000, or any range between the values. In preferred embodiments, the length to thickness ratio is at least 3, at least 5, at least 10, at least 20, at least 50, at least 100, at least 500, or any range between the values.

The method of paragraph P2, wherein the term "significantly shorter than the time that it takes the target entity to laterally diffuse across the minimum lateral dimension of the binding site" means that the ratio of the time for diffusing across the minimum lateral dimension of the binding site to the time for diffusion across the sample thickness (termed "length to thickness diffusion time ratio") is at least 3, at least 10, at least 50, at least 10, at least 100, at least 1,000, at least 10,000, at least 100,000, at least 100,000, or any range between the values. In preferred embodiments, the length to thickness diffusion time ratio is at least 3, at least 10, at least 50, at least 10, at least 100, at least 1,000, at least 10,000, or any range between the values.

P2. A device for locally binding entity in a relevant volume of a sample to a binding site on surface, comprising:
  a first plate and a second plate, that are movable relative to each other into different configurations,
  wherein the first plate has, on its surface, a binding site that has an area smaller than that of the plate and is configured to bind target entity in a sample, wherein the target entity are capable of diffusing in the sample, and wherein one or both of the plates comprise spacers and each of the spacers is fixed with its respective plate and has a predetermined height;
  wherein one of the configurations is an open configuration, in which: the two plates are either partially or completely separated apart, the spacing between the plates is not regulated by the spacers, and the sample is deposited on one or both of the plates,
  wherein another of the configuration is a closed configuration, which is configured after the sample deposition in the open configuration; and in the closed configuration: the plates are facing each other, the spacers, the binding site, and at least a portion of the sample are between the plates, the sample contacts at least a part of the binding site, the thickness of a relevant volume of the sample is regulated by the plates and the spacers, is thinner than the maximum thickness of the sample when the plates are in the open configuration, wherein the relevant volume is the volume of the sample that sits on the binding site;
  wherein the spacer height is selected to regulate the thickness of the relevant volume at the closed configuration to be at least 3 times less than the average linear dimension of the binding site.

The regulation of the thickness of the relevant volume to 3 times less than the average linear dimension of the binding site makes the diffusion time of the entity across the sample thickness is 9 times less than that across a distance equal to the average linear dimension of the binding site. Such thickness regulation makes it possible to select an incubation time, such that the incubation results in (i) a significant number of target entity in the relevant volume are bound to the binding site and (ii) a significant number of the target entity bound to the binding site are from the relevant volume of the sample, and wherein the incubation is a process to allow the target entity to bind to the binding site.

For example, if the incubation time is set to be the time that equals to the diffusion time of the entity across the thickness of the relevant volume of the sample, then after the incubation, most of the entity inside the relevant volume are already reached the binding site and being bound according to the rate equation, while the entity originally (i.e. before the incubation) outside of the relevant volume can only diffuse into the peripheral of the relevant volume (relative small volume) and such volume becomes less significant, as the ratio of the average linear dimension of the binding site to the relevant volume thickness gets larger.

4.2 Locally Binding Entity Stored on a Plate Surface to a Binding-Site on Other Plate Surface (Surface to Surface)

P3. A method for locally binding entity stored on a storage site of one plate to a binding site on another plate, comprising:
  (a) obtaining a first plate and a second plate that are movable relative to each other into different configurations, wherein a surface of first plate has a binding site; and a surface of the second plate has a storage site that comprises entity to be bound to the binding site; wherein the area of the binding site and the area of the reagent site is less than that of respective plates; and wherein one or both of the plates comprise spacers and each of the spacers is fixed with its respective plate and has a predetermined height;
  (b) obtaining a transfer medium, wherein the entity are capable of being dissolving into the transfer medium and diffusing in the transfer medium;
  (c) depositing, when the plates are configured in an open configuration, the transfer medium on one or both of the plates; wherein the open configuration is a configuration in which the two plates are partially or completely separated apart and the spacing between the plates is not regulated by the spacers;
  (d) after (c), spreading the transfer medium by bringing the plates into a closed configuration, wherein, in the closed configuration: the plates are facing each other, the spacers, the binding site, the storage site and at least a portion of the transfer medium are between the plates; at least a portion of the storage site is directly facing the binding site with a portion of the transfer medium between them, and the thickness of a relevant volume of the transfer medium is regulated by the plates and the spacers, is thinner than the maximum thickness of the sample when the plates are in the open configuration, and is significantly less than the average linear dimension of the relevant volume in the plate surface direction; and
  (e) after (d) and while the plates are in the closed configuration, incubating for a time and stopping the incubation, wherein the incubation time is selected in such that results in a significant number of the entity bound to the binding site are from the storage site, wherein the relevant volume is the volume of the transfer medium that sits on the binding site and the incubation is a process to allow the entity to bind to the binding site.

The term of "at least a port of the storage site is directly facing the binding site" means that the shortest distance from a point in the portion to the binding site is the same as the thickness of the relevant volume at the closed configuration of the plates.

P4. A device for binding entity stored on a storage site of one plate to a relevant binding site on another plate, comprising:

a first plate and a second plate that are movable relative to each other into different configurations, wherein a surface of first plate has a binding site; and a surface of the second plate has a storage site that contains entity to be bound to the binding site; wherein the area of the binding site and the area of the storage site is less than that of respective plates; and wherein one or both of the plates comprise spacers and each of the spacers is fixed with its respective plate and has a predetermined height;

wherein one of the configurations is an open configuration, in which: the two plates are either partially or completely separated apart, the spacing between the plates is not regulated by the spacers, and a transfer medium is deposited on one or both of the plates, wherein the entity on the storage site are capable of being dissolving into the transfer medium and diffusing in the transfer medium, wherein another of the configuration is a closed configuration, which is configured after the transfer medium deposition in the open configuration; and in the closed configuration: the plates are facing each other, the spacers, the binding site, the storage site and at least a portion of the transfer medium are between the plates; at least a portion of the storage site is directly facing the binding site with a portion of the transfer medium between them, and the thickness of a relevant volume of the transfer medium is regulated by the plates and the spacers, and is thinner than the maximum thickness of the sample when the plates are in the open configuration;

wherein the relevant volume is the volume of the transfer medium that sits on the storage site when the plates are in closed configuration; and wherein the spacer height is selected to regulate the thickness of the relevant volume at the closed configuration to be at least 3 times less than the average linear dimension of the binding site.

wherein at least one of the spacers is inside the sample contact area;

and the spacers that have a predetermined inter-spacer distance and height.

4.3 A Method for Locally Binding Entity on Multiple Storage Sites of One Plate to Multiple Corresponding Binding Sites on Another Plate P5. A method for locally binding entity stored on multiple storage sites of one plate to multiple corresponding binding sites on another plate, comprising:

(a) obtaining a first plate and a second plate that are movable relative to each other into different configurations; wherein a surface of first plate has multiple binding sites, and a surface of the second plate has multiple corresponding storage sites; wherein each corresponding storage site is located in a location on the second plate that is corresponding to the location of a binding site, so that when the two plates are placed face-to-face, each binding site overlaps only one storage site; and wherein one or both of the plates comprise spacers and each of the spacers is fixed with its respective plate and has a predetermined height;

(b) obtaining a transfer medium, wherein the entity on the storage sites are capable of being dissolving into the transfer medium and diffusing in the transfer medium;

(c) depositing, when the plates are configured in an open configuration, the transfer medium on one or both of the plates; wherein the open configuration is a configuration in which the two plates are partially or completely separated apart and the spacing between the plates is not regulated by the spacers;

(d) after (c), spreading the transfer medium by bringing the plates into a closed configuration, wherein, in the closed configuration: the two plates are facing each other, the spacers, the binding sites, the storage sites and at least a portion of the transfer medium are between the plates, each binding site directly faces only one corresponding storage site, the transfer medium contacts at least a part of each of the binding sites and a part of each of the storage sites, the thickness of a relevant volume of the transfer medium is regulated by the plates and the spacers, is thinner than the maximum thickness of the transfer medium when the plates are in the open configuration, and is significantly less than the average linear dimension of the binding sites; and (e) after (d) and while the plates are in the closed configuration, incubating for a time and stopping the incubation, wherein the incubation time is selected in such that results in a significant number of the entity bound to each binding site are from a corresponding storage site, wherein the relevant volume is the volume of the transfer medium that sits on the binding sites, and the incubation is a process to allow the entity to be bound to the binding site.

In some embodiments the spacing is limited to the binding sample area.

In some embodiments of the method P5, the transfer medium is a sample with target analyte, the binding site comprises capture agent, and the entity in the storage site is detection agent, wherein the target analyte binds the capture agent and the detection agent to form a capture agent-analyte-detection agent sandwich. The method P5 simplify an assay steps and can reduce the assay time by using smaller spacer height to have a thinner sample thickness and shorter vertical diffusion time for both analytes and detection agents for a shorter saturation assay time.

P6. A device for locally binding entity stored on multiple storage sites of one plate to multiple corresponding binding sites on another plate, comprising:

a first plate and a second plate that are movable relative to each other into different configurations;

wherein a surface of first plate has multiple binding sites, and a surface of the second plate has multiple corresponding storage sites; wherein each corresponding storage site is located in a location on the second plate that is corresponding to the location of a binding site, so that when the two plates are placed face-to-face, each binding site overlaps only one storage site; and wherein one or both of the plates comprise spacers and each of the spacers is fixed with its respective plate and has a predetermined height;

wherein one of the configurations is an open configuration, in which: the two plates are either partially or completely separated apart, the spacing between the plates is not regulated by the spacers, and a transfer medium is deposited on one or both of the plates, wherein the entity on the storage site are capable of being dissolving into the transfer medium and diffusing in the transfer medium, wherein another of the configuration is a closed configuration, which is configured after the transfer medium deposition in the open configuration; and in the closed configuration: the two plates are facing each other, the spacers, the binding sites, the storage sites and at least a portion of the transfer medium are between the plates, each binding site directly faces only one corresponding storage site, the transfer medium contacts at least a part of each of the binding sites and a part of each of the storage sites, the thickness of a relevant volume of the transfer medium is regulated by the plates and the spacers, and is thinner than the maximum thickness of the transfer medium when the plates are in the open configuration;

wherein the relevant volume is the volume of the transfer medium that sits on the storage site when the plates are in closed configuration; and wherein the predetermined spacer height is selected to regulate the thickness of the relevant volume at the closed configuration to be significantly less than the average linear dimension of the binding sites.

4.4 Locally Adding Reagent Stored on a Surface to a Portion of a Sample (Surface to Volume)

P7. A method for locally adding a reagent into a relevant volume of a sample, comprising:
  (a) obtaining a first plate and a second plate that are movable relative to each other into different configurations, wherein the first plate has, on its surface, a storage site that contains reagents to be added into a relevant volume of a sample, the reagents are capable of being dissolving into the sample and diffusing in the sample, and the area of the storage site is less than that of the plate; and wherein one or both of the plates comprise spacers and each of the spacers is fixed with its respective plate and has a predetermined height;
  (b) obtaining the sample;
  (c) depositing, when the plates are configured in an open configuration, the sample on one or both of the plates; wherein the open configuration is a configuration in which the two plates are partially or completely separated apart and the spacing between the plates is not regulated by the spacers;
  (d) after (c), spreading the sample by bringing the plates into a closed configuration; wherein, in the closed configuration: the plates are facing each other; the spacers, the storage site, and at least a portion of the sample are between the plates; the sample contacts at least a portion of the storage site and contacts the plates over an area that is larger than that of the storage site; the thickness of a relevant volume of the sample is regulated by the plates and the spacers, is thinner than the maximum thickness of the sample when the plates are in the open configuration, and is significantly less than the average linear dimension of the relevant volume in the plate surface direction; and
  (e) after (d) and while the plates are in the closed configuration, incubating for a time and stopping the incubation, wherein the incubation time is selected in such that results in (i) a significant number of the reagents dissolved in the sample are contained in the relevant volume of the sample and (ii) the reagents are in the significant part of the relevant volume, and wherein the relevant volume is the volume of the sample that sits on the storage site when the plates are in closed configuration, and the incubation is a process to allow the reagent to dissolve and diffuse in the sample.

P8. A device for locally adding a reagent stored on a plate surface into a relevant volume of a sample, comprising:
  a first plate and a second plate that are movable relative to each other into different configurations,
  wherein the first plate has, on its surface, a storage site that contains reagents to be added into a relevant volume of a sample, the reagents are capable of being dissolving into the sample and diffusing in the sample; and wherein one or both of the plates comprise spacers and each of the spacers is fixed with its respective plate and has a predetermined height;
  wherein one of the configurations is an open configuration, in which: the two plates are either partially or completely separated apart, the spacing between the plates is not regulated by the spacers, and the sample is deposited on one or both of the plates;
  wherein another of the configuration is a closed configuration, which is configured after the sample deposition in the open configuration; and in the closed configuration: the plates are facing each other, the spacers, the storage site, and at least a portion of the sample are between the plates, the sample contacts at least a portion of the storage site and at least a port of plate surface outside the storage site, the thickness of a relevant volume of the sample is regulated by the plates and the spacers, is thinner than the maximum thickness of the sample when the plates are in the open configuration, and wherein the relevant volume is the volume of the sample that sits on the storage site when the plates are in closed configuration;
  wherein the spacer height is selected to regulate the thickness of the relevant volume at the closed configuration of the plates to be at least 3 times less than the average linear dimension of the relevant volume in the plate surface direction.

5. Formation of Capture-Analyte-Detection Sandwich on a Binding Site (W)

One aspect of the present invention is to form a capture-analyte-detection sandwich on a binding site on a solid surface in a single step by using a CROF process and by putting the binding site on one plate and a storage site which stores the detection agent on the corresponding location of the other plate.

5.1 Forming Capture-Analyte-Detection Sandwich on a Binding Site in a Single Step of Incubation (General) (W)

W1. A method for forming a capture-analyte-detection sandwich on a binding site of a plate, comprising:
  (a) obtaining a sample that contains a target analyte, wherein the target analyte is capable of diffusion in the sample;
  (b) obtaining capture agents and obtaining detection agents, wherein the capture agents and the detection agents (are capable to) bind to the target analyte to form a capture agent-target analyte-detection agent sandwich;
  (c) obtaining a first plate and a second plate that are movable relative to each other into different configurations; wherein the first plates has a binding site that has the capture agents being immobilized on the site, and the second plate has a storage site that stores the detection agents; wherein when the storage site is in contact with the sample, the detection agents are capable to be dissolved into the sample and diffuse in the sample; and wherein one or both of the plates comprise spacers and each of the spacers is fixed with its respective plate and has a predetermined height;

(d) depositing, when the plates are configured in an open configuration, the sample on one or both of the plates; wherein the open configuration is a configuration in which the two plates are partially or completely separated apart and the spacing between the plates is not regulated by the spacers;

(e) after (d), spreading the sample by bringing the plates into a closed configuration, wherein, in the closed configuration: the plates are facing each other, the spacers and a relevant volume of the sample are between the plates, the thickness of the relevant volume of the sample is regulated by the plates and the spacers, and is thinner than the sample thickness when the plates are in the open configuration, and the sample is in contact with the binding site and the storage site; and (f) after (e), while the plates are in the closed configuration, incubating for a time to allow a formation of capture agent-target analyte-detection agent sandwich; wherein the relevant volume is at least a portion or an entire volume of the sample.

W2. A device for forming a capture-analyte-detection sandwich on a binding site of a plate, comprising:

a first plate and a second plate that are movable relative to each other into different configurations;

wherein the first plates has a binding site that has capture agents being immobilized on the site, and the second plate has a storage site that stores detection agents; wherein the capture agents and the detection agents (are capable to) bind to a target analyte in a sample to form a capture agent-target analyte-detection agent sandwich; wherein when the storage site is in contact with the sample, the detection agents are capable to be dissolved into the sample and diffuse in the sample; and wherein one or both of the plates comprise spacers and each of the spacers is fixed with its respective plate and has a predetermined height;

wherein one of the configurations is an open configuration, in which: the two plates are either partially or completely separated apart, the spacing between the plates is not regulated by the spacers, and the sample is deposited on one or both of the plates;

wherein another of the configuration is a closed configuration, which is configured after the sample deposition in the open configuration; and in the closed configuration: the plates are facing each other, the spacers and a relevant volume of the sample are between the plates, the thickness of the relevant volume of the sample is regulated by the plates and the spacers and is thinner than the sample thickness when the plates are in the open configuration, and the sample is in contact with the binding site and the storage site; and wherein the relevant volume is at least a portion or an entire volume of the sample.

5.2 Forming Capture-Analyte-Detection Sandwich on a Binding Site in a Single Step Incubation Using the Analyte that is from a Portion of the Sample (i.e. Locally).

W3. A method for forming a capture-analyte-detection sandwich on a binding site of a plate using the analytes that are from a portion of the sample, comprising:

(a) obtaining a sample that contains a target analyte, wherein the target analyte is capable of diffusion in the sample;

(b) obtaining capture agents and obtaining detection agents, wherein the capture agents and the detection agents are capable to bind to the target analyte to form a capture agent-target analyte-detection agent sandwich;

(c) obtaining a first plate and a second plate that are movable relative to each other into different configurations; wherein the first plates has a binding site that has the capture agents being immobilized on the site, and the second plate has a storage site that stores the detection agents, which, when the reagent a storage site is in contact with the sample, are capable to be dissolved into the sample and diffuse in the sample; and wherein one or both of the plates comprise spacers and each of the spacers is fixed with its respective plate and has a predetermined height;

(d) depositing, when the plates are configured in an open configuration, the sample on one or both of the plates; wherein the open configuration is a configuration in which the two plates are partially or completely separated apart and the spacing between the plates is not regulated by the spacers;

(e) after (d), spreading the sample by bringing the plates into a closed configuration, wherein, in the closed configuration: the plates are facing each other, the spacers, the binding site, and the storage site are between the plates, the binding site and the storage site are in contact with a relevant volume of the sample, and the thickness of the relevant volume of the sample is regulated by the plates and the spacers and is thinner than the sample thickness when the plates are in the open configuration; and is significantly less than the average linear dimension of the binding site; and (f) after (e) and while the plates are in the closed configuration, incubating for a time and stopping the incubation, wherein the incubation time is selected in such that results in a significant number of the capture-analyte-detection sandwich formed at the binding site contain the analytes that come from the relevant volume of the sample, wherein the relevant volume is the volume of the sample that sits on the binding site, and the incubation is a process to allow a formation of a capture-analyte-detection sandwich.

In some embodiments the ratio of the spacing to the site dimension may be less than ⅕.

W4. A device for forming a capture-analyte-detection sandwich on a binding site of a plate with the analytes that are from a portion of the sample, comprising:

a first plate and a second plate that are movable relative to each other into different configurations;

wherein the first plates has a binding site that has capture agents being immobilized on the site, and the second plate has a storage site that stores detection agents; wherein the capture agents and the detection agents (are capable to) bind to a target analyte in a sample to form a capture agent-target analyte-detection agent sandwich; wherein when the storage site is in contact with the sample, the detection agents are capable to be dissolved into the sample and diffuse in the sample; and wherein one or both of the plates comprise spacers and each of the spacers is fixed with its respective plate and has a predetermined height;

wherein one of the configurations is an open configuration, in which: the two plates are either partially or completely separated apart, the spacing between the plates is not regulated by the spacers, and the sample is deposited on one or both of the plates;

wherein another of the configuration is a closed configuration, which is configured after the sample deposition in the open configuration; and in the closed configuration: the plates are facing each other, the spacers, the binding site, and the storage site are between the plates, the binding site and the storage site are in contact with a relevant volume of the sample, and the thickness of the relevant volume of the sample is regulated by the plates and the spacers and is thinner than the sample thickness when the plates are in the open configuration; and wherein the relevant volume is the volume of the sample that sits on the binding site; and wherein the spacer height is selected to regulate the thickness of the relevant volume at the closed configuration to be significantly less than the average linear dimension of the binding site.

5.3 A Method for Reducing the Time of Forming Capture-Analyte-Detection Sandwich on a Binding Site by Reducing the Diffusion Distance (W, X).

W5. A method for reducing the time of forming a capture-analyte-detection sandwich on a binding site of a plate, comprising:

(a) obtaining a sample that contains a target analyte, wherein the target analyte is capable of diffusion in the sample;

(b) obtaining capture agents and obtaining detection agents, wherein the capture agents and the detection agents are capable to bind to the target analyte to form a capture agent-target analyte-detection agent sandwich;

(c) obtaining a first plate and a second plate that are movable relative to each other into different configurations; wherein the first plates has a binding site that has the capture agents being immobilized on the site, and the second plate has a storage site that stores the detection agents, which, when the reagent a storage site is in contact with the sample, are capable to be dissolved into the sample and diffuse in the sample; and wherein one or both of the plates comprise spacers and each of the spacers is fixed with its respective plate and has a predetermined height;

(d) depositing, when the plates are configured in an open configuration, the sample on one or both of the plates; wherein the open configuration is a configuration in which the two plates are partially or completely separated apart and the spacing between the plates is not regulated by the spacers;

(e) after (d), spreading the sample by bringing the plates into a closed configuration, wherein, in the closed configuration: the plates are facing each other, the spacers, the binding site, and the storage site are between the plates, the binding site overlaps the storage site, the binding site and the storage site are in contact with a relevant volume of the sample, and the thickness of the relevant volume of the sample is regulated by the plates and the spacers and is thinner than the sample thickness when the plates are in the open configuration; and thereby the reduced thickness of the sample reduces the time for the analytes and the detection agents diffusing vertically across the thickness of the sample, wherein the relevant volume is at least a portion of an entire volume of the sample.

wherein the time period to allow the target entity in the relevant volume to bind to the binding site is shorter than that without the closed configuration.

the method may further comprise a wash step to remove the sample between the plates, and the wash step is performed when the plates are in either a closed configuration or an open configuration.

The methods further comprise a read step that reads the signal from the capture-analyte-detection sandwich immobilized on the binding site. The read is performed either after a wash or without any wash.

The method may further be multiplexed, as described above or below.

W6. A device for reducing the time of forming a capture-analyte-detection sandwich on a binding site of a plate, comprising:

a first plate and a second plate that are movable relative to each other into different configurations;

wherein the first plates has a binding site that has capture agents being immobilized on the site, and the second plate has a storage site that stores detection agents; wherein the capture agents and the detection agents (are capable to) bind to a target analyte in a sample to form a capture agent-target analyte-detection agent sandwich; wherein when the storage site is in contact with the sample, the detection agents are capable to be dissolved into the sample and diffuse in the sample; and wherein one or both of the plates comprise spacers and each of the spacers is fixed with its respective plate and has a predetermined height;

wherein one of the configurations is an open configuration, in which: the two plates are either partially or completely separated apart, the spacing between the plates is not regulated by the spacers, and the sample is deposited on one or both of the plates;

wherein another of the configuration is a closed configuration, which is configured after the sample deposition in the open configuration; and in the closed configuration: the plates are facing each other, the spacers, the binding site, and the storage site are between the plates, the binding site overlaps the storage site, the binding site and the storage site are in contact with a relevant volume of the sample, and the thickness of the relevant volume of the sample is regulated by the plates and the spacers and is thinner than the sample thickness when the plates are in the open configuration; and thereby the reduced thickness of the sample reduces the time for the analytes and the detection agents diffusing vertically across the thickness of the sample, wherein the relevant volume is at least a portion of an entire volume of the sample.

In these embodiments, the method may comprise attaching a capture agent a plate, wherein the attaching is done via a chemical reaction of the capture agent with a reactive group on the plate. The other plate may contain a patch of a dried detection reagent at a location such that, after the plates are closed, the affixed capture agent and the patch of detection reagent are facing each other. Next, the method may comprise contacting a sample containing a target-analyte with the device and closing the plates, as described above. The detection reagent dissolves and diffuses into the sample. Since the target analyte is in solution, the target analyte will be bound by the capture agent and immobilized to the surface of one of the plates. The detection agent can bind to the target analyte before or after it is bound to the capture agent. In some cases, the method may comprises removing any target-analytes that are not bound to the capture agent, or any unbound detection reagent (e.g., by washing the surface of a plate in binding buffer); The detection agent may be conjugated with an optical detectable label, thereby providing a way to detect the target analyte. After optionally removing the detection agent that are not bound to the target-analyte, the system can be read, e.g., using a reading system, to read a light signal (e.g., light at a wavelength that is in the range of 300 nm to 1200 nm) from detection agent that is bound to the plate. Further, as mentioned above, the detection agent may be labeled directly (in which case the detection agent may be strongly linked to a light-emitting label prior to deposition onto one of the plates), or labeled indirectly (i.e., by binding the detection agent to a second capture agent, e.g., a secondary antibody that is labeled or a labeled nucleic acid, that specifically binds to the detection agent and that is linked to a light-emitting label). In some embodiments, the method may comprise a blocking agent, thereby preventing non-specific binding of the capture agents to non-target analytes. Suitable conditions for the specific binding of target analytes to other agents, include proper temperature, time, solution pH level, ambient light level, humidity, chemical reagent concentration, antigen-antibody ratio, etc., are all well known or readily derivable from the present disclosure. General methods for methods for molecular interactions between capture agents and their binding partners (including analytes) are well known in the art (see, e.g., Harlow et al., *Antibodies: A Laboratory Manual*, First Edition (1988) Cold spring Harbor, N.Y.; Ausubel, et al, *Short Protocols in Molecular Biology*, 3rd ed., Wiley & Sons, 1995). The methods described above and below are exemplary; the methods herein are not the only ways of performing an assay.

In certain embodiments, a nucleic acid capture agent can be used to capture a protein analyte (e.g., a DNA or RNA binding protein). In alternative embodiments, the protein capture agent (e.g., a DNA or RNA binding protein) can be used to capture a nucleic acid analyte.

The sample may be a clinical sample derived from cells, tissues, or bodily fluids. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate.

In one embodiment of this assay, a plate is contacted with a sample containing a target analyte (e.g., a target protein) and the plates are closed. The sample contains, or is amended to contain, all necessary reagents (e.g., salts and the like) conditions suitable for specific binding. The capture agents (e.g., antibodies) and detection agent specifically bind to a target analyte in the sample, thereby leading to a patch of labeled analyte that can be detected.

As in any embodiment, the amount of target analyte in the sample can be measured to provide a qualitative or quantitative measure of the amount of target analyte in the sample. In some embodiments, the magnitude of the signal provides a quantitative determination of the amount of target analyte in the sample. In some cases, the evaluation may be compared to a standard curve (e.g., of a second analyte or a spiked-in analyte) that may in certain cases be at a known concentration. This comparison may be facilitated by depositing capture agents at different densities (e.g., different concentrations) and reading the signal from each patch of capture agent.

6 Binding and Adding Using Samples and Reagent with Small Volume (V)

It is highly desirable, in many applications, to use as small volume of a sample or reagent as possible. However, in microfluidic channel devices (the most popular approach today for using small samples), a significant volume of the sample is wasted in flowing from an inlet to a testing (detection) region of the device, resulting a need to a sample volume larger than the volume in the testing location. One aspect of the present invention is to significantly reduce the volume of the sample or reagent used in a testing, by depositing a tiny volume of a sample or a reagent on a plate and then reshaping the volume into a thin film with a smaller thickness but larger area than before. Such reshaping also allows faster reaction.

6-1 Binding Target Entity in a Small Volume Sample on a Surface Binding Site by Spreading the Sample.

V1. A method for binding target entity in a sample to a binding site, comprising:
 (a) obtaining a first plate and a second plate that are movable relative to each other into different configurations, wherein the first plate has, on its surface, a binding site, and wherein one or both of the plates comprise spacers and each of the spacers is fixed with its respective plate and has a predetermined height;
 (b) obtaining a sample that contains a target entity to be bound to the binding site;
 (c) depositing, when the plates are configured in an open configuration, the sample on one or both of the plates; wherein, in the open configuration: the two plates are partially or completely separated apart, the spacing between the plates is not regulated by the spacers, and the sample, as deposited, covers either no area or a partial area of the binding site;
 (d) after (c), spreading the sample by bringing the plates into a closed configuration; wherein, in the closed configuration: the plates are facing each other, the spacers and a relevant volume of the sample are between the plates, the sample contacts more area of the binding site than that when the plates are in the open configuration, and the thickness of the relevant volume of the sample on the binding site is regulated by the plates and the spacers, wherein the relevant volume is a portion or an entire volume of the sample.

V2. A device for binding target entity in a sample to a surface binding site, comprising:
 a first plate and a second plate that are movable relative to each other into different configurations;
 wherein the first plate has, on its surface, a binding site that binds target entity in a sample, and wherein the binding site has an area larger than the contact area of the sample when the sample is deposited on only one of the plates and without contacting the other plate;
 wherein one or both of the plates comprise spacers and each of the spacers is fixed with its respective plate and has a predetermined height;
 wherein one of the configurations is an open configuration, in which: the two plates are either partially or completely separated apart, the spacing between the plates is not regulated by the spacers, and the sample is deposited on one or both of the plates and covers, as deposited, either no area or a partial area of the binding site;
 wherein another of the configuration is a closed configuration, which is configured after the sample deposition in the open configuration; and in the closed configuration: the plates are facing each other, the spacers and the sample are between the plates, the sample contacts more area of the binding site than that when the plates are in the open configuration, and the thickness of the sample on the binding site is regulated by the plates and the spacers.

6-2 Adding Reagents into a Small Volume Sample by Spreading the Sample

V3. A method for binding target entity in a sample to a binding site, comprising:
  (a) obtaining a first plate and a second plate that are movable relative to each other into different configurations, wherein the first plate has, on its surface, a storage site that contains the reagents to be added into the sample, and wherein one or both of the plates comprise spacers and each of the spacers is fixed with its respective plate and has a predetermined height;
  (b) depositing, when the plates are configured in an open configuration, the sample on one or both of the plates; wherein, in the open configuration: the two plates are partially or completely separated apart, the spacing between the plates is not regulated by the spacers, and the sample, as deposited, contacts either no area or a partial area of the storage site;
  (c) after (b), spreading the sample by bringing the plates into a closed configuration; wherein, in the closed configuration: the plates are facing each other, the spacers and a relevant volume of the sample are between the plates, the sample contacts more area of the storage site than that when the plates are in the open configuration, and the thickness of the relevant volume of the sample is regulated by the spacer; and wherein the relevant volume is a portion of the sample that site on the storage site.

V4. A device for binding target entity in a sample to a binding site, comprising:
  a first plate and a second plate that are movable relative to each other into different configurations,
  wherein the first plate has, on its surface, a storage site that contains reagents and the reagents are to be added into the sample, and wherein one or both of the plates comprise spacers and each of the spacers is fixed with its respective plate and has a predetermined height;
  wherein one or both of the plates comprise spacers and each of the spacers is fixed with its respective plate and has a predetermined height;
  wherein one of the configurations is an open configuration, in which: the two plates are either partially or completely separated apart, the spacing between the plates is not regulated by the spacers, and the sample is deposited on one or both of the plates,
  wherein another of the configuration is a closed configuration, which is configured after the sample deposition in the open configuration; and in the closed configuration: the plates are facing each other, the spacers and a relevant volume of the sample are between the plates, the sample contacts more areas of the storage site than that when the plates are in the open configuration, and the thickness of the relevant volume of the sample is regulated by the spacer; and wherein the relevant volume is a portion of the sample that site on the storage site.

In the methods of paragraph V1 and V2 and the devices of V3 and V4, in some cases, even a sample is deposited in the binding site area or the storage area, due to the small volume of the sample and a wetting property of the surface, the contact area of as-deposited sample with a plate will be less than the area of the binding site or the storage site. Hence, a spreading, particular precisely spreading is needed.

Drops of a sample can be multiple drops, and in the closed configuration, the drops merged into a film with a thickness less than the maximum thickness.

In present invention, in the method in paragraph V1 to V7 and the devices in paragraph of V2 to V8, the volume of the sample that is deposited on the plate or the plates ("sample volume") is at most 0.001 pL (pico liter), at most 0.01 pL, at most 0.1 pL, at most 1 pL, at most 10 pL, at most 100 pL, at most 1 nL (nano liter), at most 10 nL, at most 100 nL, at most 1 uL (micro liter), at most 10 uL, at most 100 uL, at most 1 mL (milliliter), at most 10 mL, or a range of any two of these values.

7 Uniform Binding or Adding Reagents Using Uniform Sample Thickness (UAB)

For assays and chemical reactions, it is advantageous to make a thin sample thickness uniform over a significant area. The examples include binging of entity of sample to a surface binding site, adding reagents into a sample, quantification a relevant volume of the sample, quantification of analytes, and others. For the methods that use two plates to reduce and regulate a thickness of a relevant volume (a portion or an entire volume) of a sample, it is essential to be precise, uniform and easy-to-use.

One aspect of the present invention is to improve the precision, uniformity, or easy-to-use of the methods and/or devices that regulate a thickness of a relevant volume of a sample by compressing the sample with two plates.

7.1 A Method for Uniformly Binding an Entity in a Sample into a Binding Site of a Plate UAB1. A method for uniformly binding an entity in a sample into a binding site of a plate, comprising:
  (a) obtaining a sample that contains target entity which are capable of diffusing in the sample;
  (b) obtaining a first plate and a second plate that are movable relative to each other into different configurations, wherein the first plate has, on its surface, a binding site that is configured to bind the target entity, wherein one or both of the plates comprise spacers and each of the spacers is fixed with its respective plate and has a predetermined height;
  (c) depositing, when the plates are configured in an open configuration, the sample on one or both of the plates; wherein the open configuration is a configuration in which the two plates are either partially or completely separated apart and the spacing between the plates is not regulated by the spacers;
  (d) after (c), spreading the sample by bringing the plates into a closed configuration, wherein, in the closed configuration: the plates are facing each other, the spacers and the relevant volume of the sample are between the plates, the binding site is in contact with the relevant volume, the thickness of the relevant volume of the sample is regulated by the plates and the spacers and is, compared to the plates are in the open configuration, thinner than the maximum thickness of the sample and more uniform over the binding site;
  wherein the spacers and the plate are configured to make the regulated thickness of the relevant volume at the plate closed configuration more uniform than that in the plate open configuration; and wherein the relevant volume is a portion or an entire volume of the sample.
  It further has a storage site on the plate opposite to the binding site for forming a uniform sandwich.

UAB2. A device for uniformly binding an entity in a sample into a binding site on a plate, comprising:
- a first plate and a second plate that are movable relative to each other into different configurations;
- wherein the first plate has, on its surface, a binding site that is configured to bind the target entity, wherein one or both of the plates comprise spacers and each of the spacers is fixed with its respective plate and has a predetermined height;
- wherein one of the configurations is an open configuration, in which: the two plates are either partially or completely separated apart, the spacing between the plates is not regulated by the spacers, and the sample is deposited on one or both of the plates;
- wherein another of the configuration is a closed configuration, which is configured after the sample deposition in the open configuration; and in the closed configuration: the plates are facing each other, the spacers and the relevant volume of the sample are between the plates, the binding site is in contact with the relevant volume, the thickness of the relevant volume of the sample is regulated by the plates and the spacers and is, compared to the plates are in the open configuration, thinner than the maximum thickness of the sample and more uniform over the binding site;
- wherein the spacers and the plates are configured to make the regulated thickness of the relevant volume at the plate closed configuration more uniform than that in the plate open configuration; and wherein the relevant volume is a portion or an entire volume of the sample.

7.2 A Method for Uniformly Adding a Regent on a Plate into a Sample

UAB3. A method for uniformly adding a reagent into a relevant volume of a sample, comprising:
(a) obtaining a first plate and a second plate that are movable relative to each other into different configurations, wherein the first plate has, on its surface, a storage site that contains reagents to be added into a relevant volume of a sample, the reagents are capable of being dissolving into the sample and diffusing in the sample; and wherein one or both of the plates comprise spacers and each of the spacers is fixed with its respective plate and has a predetermined height;
(b) obtaining the sample;
(c) depositing, when the plates are configured in an open configuration, the sample on one or both of the plates; wherein the open configuration is a configuration in which the two plates are partially or completely separated apart and the spacing between the plates is not regulated by the spacers;
(d) after (c), spreading the sample by bringing the plates into a closed configuration, wherein, in the closed configuration: the plates are facing each other, the spacers and the relevant volume of the sample are between the plates, the storage site is in contact with the relevant volume, and the thickness of the relevant volume of the sample is regulated by the plates and the spacers and is thinner than the maximum thickness of the sample when the plates are in the open configuration;
  - wherein the spacers and plates are configured to make the thickness of the relevant volume of the sample more uniform over the area of the relevant volume at the plate closed configuration than that at the plate open configuration; and wherein the relevant volume is a portion or an entire volume of the sample.

UAB4. A device for uniformly adding a reagent into a relevant volume of a sample, comprising:
- a first plate and a second plate that are movable relative to each other into different configurations;
- wherein the first plate has, on its surface, a storage site that contains reagents to be added into a relevant volume of a sample, the reagents are capable of being dissolving into the sample and diffusing in the sample; and wherein one or both of the plates comprise spacers and each of the spacers is fixed with its respective plate and has a predetermined height;
- wherein one of the configurations is an open configuration, in which: the two plates are either partially or completely separated apart, the spacing between the plates is not regulated by the spacers, and the sample is deposited on one or both of the plates;
- wherein another of the configuration is a closed configuration, which is configured after the sample deposition in the open configuration; and in the closed configuration: the plates are facing each other, the spacers and the relevant volume of the sample are between the plates, the storage site is in contact with the relevant volume, and the thickness of the relevant volume of the sample is regulated by the plates and the spacers and is thinner than the maximum thickness of the sample when the plates are in the open configuration;
- wherein the spacers and plates are configured to make the thickness of the relevant volume of the sample more uniform over the area of the relevant volume at the plate closed configuration than that at the plate open configuration; and wherein the relevant volume is a portion or an entire volume of the sample.

7.3 A Method for Uniformly Forming a Capture-Analyte-Detection Sandwich

UAB5. A method for uniformly a capture-analyte-detection sandwich on a binding site of a plate, comprising:
(a) obtaining a sample that contains a target analyte;
(b) obtaining capture agents and obtaining detection agents, wherein the capture agents and the detection agents (are capable to) bind to the target analyte to form a capture agent-target analyte-detection agent sandwich;
(c) obtaining a first plate and a second plate that are movable relative to each other into different configurations; wherein the first plates has a binding site that has the capture agents being immobilized on the site, and the second plate has a storage site that stores the detection agents, which, when the storage site is in contact with the sample, are capable to be dissolved into the sample and diffuse in the sample; and wherein one or both of the plates comprise spacers and each of the spacers is fixed with its respective plate and has a predetermined height;
(d) depositing, when the plates are configured in an open configuration, the sample on one or both of the plates; wherein the open configuration is a configuration in which the two plates are partially or completely separated apart and the spacing between the plates is not regulated by the spacers;
(e) after (d), spreading the sample by bringing the plates into a closed configuration, wherein, in the closed configuration: the plates are facing each other, the spacers and a relevant volume of the sample are between the plates, the thickness of the relevant volume of the sample is regulated by the plates and the spacers and is thinner than the sample thickness when the plates are in the open configuration, and the sample is in contact with the binding site and the storage site;

wherein the spacers and plates are configured to make the thickness of the relevant volume of the sample more uniform over the area of the relevant volume at the plate closed configuration than that at the plate open configuration; and wherein the relevant volume is a portion or an entire volume of the sample.

UAB6. A device for uniformly a capture-analyte-detection sandwich on a binding site of a plate, comprising:

a first plate and a second plate that are movable relative to each other into different configurations;

wherein the first plates has a binding site that has capture agents being immobilized on the site, and the capture agents are capable of binding to a target analyte in a sample;

wherein the second plate has a storage site that stores the detection agents, which, are capable of (a) when the storage site is in contact with the sample, being dissolved into the sample and diffuse in the sample; and (b) binding to the target analyte and form a capture agent-target analyte-detection agent sandwich;

wherein one or both of the plates comprise spacers and each of the spacers is fixed with its respective plate and has a predetermined height;

wherein one of the configurations is an open configuration, in which: the two plates are either partially or completely separated apart, the spacing between the plates is not regulated by the spacers, and the sample is deposited on one or both of the plates;

wherein another of the configuration is a closed configuration, which is configured after the sample deposition in the open configuration; and in the closed configuration: the plates are facing each other, the spacers and a relevant volume of the sample are between the plates, the thickness of the relevant volume of the sample is regulated by the plates and the spacers and is thinner than the sample thickness when the plates are in the open configuration, and the sample is in contact with the binding site and the storage site;

wherein the spacers and plates are configured to make the thickness of the relevant volume of the sample more uniform over the area of the relevant volume at the plate closed configuration than that at the plate open configuration; and wherein the relevant volume is a portion or an entire volume of the sample.

7.4 Uniform Regulating a Thickness of a Relevant Volume of a Sample Between Two Plates.

UAB7. A method for regulating a thickness of a relevant volume of a sample, comprising:

(a) obtaining a sample, wherein a thickness of a relevant volume of the sample is to be regulated;

(b) obtaining two plates that are movable relative to each other into different configurations, wherein one or both of the plates comprise spacers, the spacers have a predetermined inter-spacer distance and height, and each of the spacers is fixed with its respective plate;

(c) depositing, when the plates are configured in an open configuration, the sample on one or both of the plates; wherein the open configuration is a configuration in which the two plates are either partially or completely separated apart and the spacing between the plates is not regulated by the spacers;

(d) after (c), spreading the sample by bringing the plates into a closed configuration, wherein, in the closed configuration: the plates are facing each other, the spacers and the relevant volume of the sample are between the plates, the thickness of the relevant volume of the sample is regulated by the plates and the spacers and is thinner than the maximum thickness of the sample when the plates are in the open configuration;

wherein the spacers and plates are configured to make the thickness of the relevant volume of the sample more uniform over the area of the relevant volume at the plate closed configuration than that at the plate open configuration; and wherein the relevant volume is a portion or an entire volume of the sample.

UAB8. A device for regulating a thickness of a relevant volume of a sample, comprising:

a first plate and a second plate that are movable relative to each other into different configurations;

wherein one or both of the plates comprise spacers, the spacers have a predetermined inter-spacer distance and height, and each of the spacers is fixed with its respective plate;

wherein one of the configurations is an open configuration, in which: the two plates are either partially or completely separated apart, the spacing between the plates is not regulated by the spacers, and the sample is deposited on one or both of the plates;

wherein another of the configuration is a closed configuration, which is configured after the sample deposition in the open configuration; and in the closed configuration: the plates are facing each other, the spacers and the relevant volume of the sample are between the plates, the thickness of the relevant volume of the sample is regulated by the plates and the spacers and is thinner than the maximum thickness of the sample when the plates are in the open configuration;

wherein the spacers and plates are configured to make the thickness of the relevant volume of the sample more uniform over the area of the relevant volume at the plate closed configuration than that at the plate open configuration; and wherein the relevant volume is a portion or an entire volume of the sample In the methods and the devices in the paragraphs of U1 to U8, the configuration of the spacers and plates that make the thickness of the relevant volume of the sample uniform has an embodiment described in the disclosure.

Uniformity of Sample Thickness.

In the methods and the devices in the paragraphs of U1 to U8, the uniformity of the thickness of the relevant volume of the sample is such that the sample thickness at the closed configuration has a relative variation of at most 0.001%, at most 0.01%, at most 0.05%, at most 0.1%, at most 0.5%, at most 1%, at most 2%, at most 5%, at most 10%, at most 20%, at most 30%, at most 50%, at most 75%, at most 90%, less than 100%, or a range between any two of these values.

In a preferred embodiment of the methods and the devices in the paragraphs of U1 to U8, the uniformity of the thickness of the relevant volume of the sample is such that the sample thickness at the closed configuration has a relative variation of at most 0.1%, at most 0.5%, at most 1%, at most 2%, at most 5%, at most 10%, at most 20%, at most 30%, at most 50%, or a range between any two of these values.

Another parameter that can be important to reduce the saturation incubation time is the uniformity of the sample thickness. If the thickness has a large variation over the binding site, the saturation incubation time can vary from location to location in the binding site, forcing a longer saturation incubation time to ensure all locations in the binding site having reached the saturation.

8 Amplification Surface

One of current major obstacles for PoC diagnostics and for any assays which use a small sample volume is poor sensitivities. It is desirable to enhance the signal of an assay. One aspect of the present invention is related to the devices and methods that put the binding site on a signal amplification surface (SAS) to amplify the signal for achieving higher sensitivity. Signal amplification surfaces may also be referred to as signal amplification layers (SAL).

The general structures of SAL comprise nanoscale metal-dielectric/semiconductor-metal structures, which amplifies local surface electric field and gradient and light signals. The amplification are the high at the location where there are the sharp (i.e. large curvature) edges of a metal structure and the between a small gaps of the two metal structures. The highest enhancement regions are those having both the sharp edges and the small gaps. Furthermore, the dimensions for all metallic and non-metallic micro/nanostructures generally are less than the wavelength of the light the SAL amplifies (i.e., subwavelength).

In some embodiments, a SAL layer has as many of the metallic sharp edges and the small gaps as possible. This requires having a dense group of metallic nanostructures with small gaps between the nanostructures. SAL structures may include several different layers. Furthermore, the SAL layer itself can be further improved by a process that can further cover the portions of the metallic materials that do not have sharp edges and small gaps, as described in U.S. provisional application Ser. No. 61/801,424, filed on Mar. 15, 2013, and PCT application WO2014197096, filed on Mar. 15, 2014, which are incorporated by reference for all purposes, as well as PCT/US2014/028417 (Chou et al, "Analyte Detection Enhancement By Targeted Immobilization, Surface Amplification, And Pixelated Reading And Analysis"), which is incorporated by reference herein for all purposes.

M1. In some embodiments, the amplification surface is a metal layer on or near the binding site surface. A method for amplifying the signal of assaying a target entity in a relevant volume of a sample, comprising:

(a) obtaining a sample that contains a target entity;
(b) obtaining two plates that are movable relative to each other into different configurations, wherein one of the plates comprises, on its surface, one binding site that comprises a signal amplification surface that is configured to bind the target entity and to amplify an optical signal which is on or near the signal amplification surface; and wherein one or both of the plates comprise spacers and each of the spacers is on its respective plate and has a predetermined height;
(c) depositing, when the plates are configured in an open configuration, the sample on one or both of the plates; wherein the open configuration is a configuration in which the two plates are separated apart and the spacing between the plates is not regulated by the spacers;
(d) after (c), spreading the sample by bringing the plates into a closed configuration, wherein, in the closed configuration: the plates are facing each other, the spacers and the relevant volume of the sample are between the plates, the thickness of the relevant volume of the sample is regulated by the plates and the spacers and is thinner than that when the plates are in the open configuration, and the relevant volume of the sample is in contact with the binding site; and
(e) after (e), incubating, while the plates are in the closed configuration, for a time period to allow the target entity in the relevant volume of the sample to bind to the binding site; wherein the relevant volume is a portion of the sample that contact to the binding site when the plates are in the closed configuration.

M2. A device for amplifying the signal in assaying a target entity in a relevant volume of a sample, comprising:

a first plate and a second plate that are movable relative to each other into different configurations,
wherein the first plate comprises, on its surface, one binding site, and the binding site comprises a signal amplification surface that is configured to (i) bind a target entity in a sample and (ii) amplify an optical signal which is on or near the signal amplification surface;
wherein one or both of the plates comprise spacers and each of the spacers is on its respective plate and has a predetermined height;
wherein one of the configurations is an open configuration, in which: the two plates are either partially or completely separated apart, the spacing between the plates is not regulated by the spacers, and the sample is deposited on one or both of the plates,
wherein another of the configuration is a closed configuration, which is configured after the sample deposition in the open configuration; and in the closed configuration: the plates are facing each other, the spacers and the relevant volume of the sample are between the plates, the thickness of the relevant volume of the sample is regulated by the plates and the spacers and is thinner than that when the plates are in the open configuration;
wherein the relevant volume is a portion of the sample that contact to the binding site when the plates are in the closed configuration.

In some embodiments, the signal amplification surface includes at least one of a metal-dielectric nanostructure, a metal-semiconductor nanostructure, and a disk-coupled dots-on-pillar antenna array.

In some embodiments, the signal amplification surface includes a metal layer.

9 Detection and/or Quantification of Volume and/or Concentration (Q)

Quantification and/or control of a relevant volume of a sample is useful for quantification and/or control of the concentration of chemical compounds (including analytes, entity, reagents, etc.) in the sample.

Common methods for a sample volume quantification include a use of a metered pipette (e.g., Eppendorf's "Research plus pipette, adjustable, 0.5-10 µL", SKU #3120000020), or a geometry. For PoC (point of care) or home uses, such metering devices are inconvenient to use and/or expensive. There are needs for simpler and cheaper methods and devices for the quantification and/or control of the sample volume and/or the concentration.

One aspect of the present invention is related to the methods, devices, and systems that quantify and/or control a relevant volume of a sample that deposited on a plate, without using a metered pipette and/or a fixed microfluidic channel. The relevant volume, which can be a portion or the entire volume of the sample, is relevant to the quantification and/or control of the concentration of target analyte and/or entity in the sample. The methods, devices and systems in the present invention are easy to use and low cost.

9.1 A Method for Quantifying a Relevant Volume of a Sample

Q1. A method for quantifying a relevant volume of a sample, comprising:
   (a) obtaining a sample, wherein a relevant volume of the sample is to be quantified;
   (b) obtaining two plates that are movable relative to each other into different configurations, wherein one or both of the plates comprise spacers and the spacers have a predetermined inter-spacer distance and height, and each of the spacers is fixed with its respective plate;
   (c) depositing, when the plates are configured in an open configuration, the sample on one or both of the plates; wherein the open configuration is a configuration in which the two plates are either partially or completely separated apart and the spacing between the plates is not regulated by the spacers;
   (d) after (c), spread the sample by bringing the plates into a closed configuration, wherein, in the closed configuration: the plates are facing each other, the spacers and the relevant volume of the sample are between the plates, the thickness of the relevant volume of the sample is regulated by the plates and the spacers and is thinner than the maximum thickness of the sample when the plates are in the open configuration, and at least one of the spacers is inside the sample;
   (e) quantifying the relevant volume of the sample while the plates are in the closed configuration;
      wherein the relevant volume is at least a portion of an entire volume of the sample.

Q2. In some embodiments, a method for quantifying a relevant volume in a sample, comprises:
   (a) obtaining a first plate and a second plate;
   (b) making a sample to quantified between the two plates;
   (c) deforming the shape of the sample by compressing the two plate that reduces the sample thickness and spreading the sample between the plates laterally; and
   (d) quantifying the relevant volume of the sample while the plates are in the closed configuration;
   wherein the relevant volume is at least a portion of an entire volume of the sample.

9.2 A Plate for Use in Quantifying a Relevant Volume in a Sample

Q3. A plate for use in quantifying a relevant volume in a sample, comprising:
   a plate that comprises, on its surface, (i) spacers that have a predetermined inter-spacer distance and height and are fixed on the surface, and (ii) a sample contact area for contacting a sample with a relevant volume to be quantified, wherein at least one of the spacers is inside the sample contact area.

9.3 A Device for Use in Quantifying a Relevant Volume in a Sample

Q4. A device for quantifying a relevant volume in a sample, comprising:
   a first plate and a second plate that (a) are movable relative to each other into different configurations and (b) each has a sample contact area for contacting a sample with a relevant volume to be quantified,
   wherein one or both of the plates comprise, on its surface, spacers that have a predetermined inter-spacer distance and height, and the spacers are fixed with respective plates;
   wherein one of the configurations is an open configuration, in which: the two plates are separated apart, the spacing between the plates is not regulated by the spacers, and the sample is deposited on one or both of the plates,
   wherein another of the configuration is a closed configuration, which is configured after the sample deposition in the open configuration; and in the closed configuration: the plates are facing each other, the spacers and the relevant volume of the sample are between the plates, the thickness of the relevant volume of the sample is regulated by the plates and the spacers and is thinner than that when the plates are in the open configuration, and at least one of the spacers is inside the sample; and
   wherein the relevant volume of the sample is quantified in the closed configuration, and the relevant volume is at least a portion of an entire volume of the sample.

9-5. Measuring a Relevant Volume of a Sample

MS1. In the present invention, the quantifying of a relevant volume of the sample while the plates are at a closed configuration includes, but not limited to, each of the following five embodiments:
   (a) measuring the relevant volume of the sample by a method of mechanical, optical, electrical, or any combination of thereof;
   (b) measuring one or several parameter(s) related to the relevant volume of the sample independently using a method selected from a method that is mechanical, optical, electrical, or any combination of thereof;
   (c) using predetermined one or several parameter(s) related to the relevant volume of the sample (i.e. the parameter(s) of the sample determined prior to the plates are at the closed configuration);
   (d) determining the relevant volume of the sample by (i) measuring one or several parameters related to the revel vent volume when the plates are at a closed configuration and (ii) predetermining other parameters related to the relevant volume before the plates are at the closed configuration;
   (e) determining none-sample volume
   (f) any combinations of the above (i.e. a, b and c).

In the method of paragraph MS1, the mechanical methods include, but not limited to, a use of the spacers (i.e. the mechanical device that regulate the spacing between the inner surfaces of the substrate and the cover-plate to a predetermined value), mechanical probe or rulers, sound waves (e.g. reflection and/or interference of ultrasound wave to measure the spacing), or any combination of thereof.

In the method of paragraph MS1, the optical methods include, but not limited to, a use of light interference, or optical imaging (e.g. taking a 2D (two-dimensional)/3D (three-dimensional) image of the sample, optical imaging of multiple times (with different viewing angles, different wavelength, different phase, and/or different polarization), image processing, or any combination of thereof.

The electrical methods include, but not limited to, capacitive, or resistive or impedance measurements, or any combination of thereof.

In the method of paragraph MS1, in some embodiments, the measurement of the sample thickness is to measure the spacing between the inner surfaces of the two plate.

In the method of paragraph MS1, in some embodiments, the use of predetermined one or several parameter(s) related to the relevant volume of the sample, wherein the predetermined parameter is the predetermined sample thickness that is regulated by the spacers when the plates are in a closed configuration.

In the method of paragraph MS1, in some embodiments, the use of predetermined one or several parameter(s) related to the relevant volume of the sample, wherein the predetermined parameter is the predetermined the spacer height.

In the method of paragraph of MS1, in some embodiments, the parameters related to the relevant volume of the sample are the parameters at a closed configuration, that include, but not limited to, (i) the spacing between the inner surfaces of the first plate and the second plate (in CROF), (ii) the sample thickness, (iii) the entire or a relevant portion of the sample area, (iv) the entire or a relevant portion of the sample volume, or (v) any combination of thereof.

In the method of paragraph MS1, in some embodiments, the quantification of the sample volume or a relevant sample volume, comprising steps of (i) multiplying the sample thickness by the entire sample area to get the entire sample volume, (ii) multiplying the sample thickness by the relevant sample area to get the relevant sample volume, or (iii) multiplying the relevant sample thickness by the entire or relevant sample area to get the relevant sample volume.

In the method of paragraph MS1, in some embodiments, the measurement is to take 3D (three-dimensional) image of the relevant volume.

In the method of paragraph MS1, in some embodiments, the quantification of the relevant volume of the sample by measuring the lateral area of the relevant volume of the sample, then using it with the thickness of the relevant volume to determine the volume of the relevant volume of the sample, wherein the thickness of the relevant volume is determined from the information of the spacer, and the information of the spacer include the spacer height;

In the method of paragraph MS1, in some embodiments, the quantification of the relevant volume of the sample by measuring the lateral area of the relevant volume of the sample and the spacer together, then using it with the thickness of the relevant volume and the volume of the spacers to determine the volume of the relevant volume of the sample, wherein the thickness of the relevant volume is determined from the inform of the spacer;

In the method of paragraph MS1, in some embodiments, the quantification of the relevant volume of the sample by measuring the lateral area and the thickness of the relevant volume of the sample;

In the method of paragraph MS1, in some embodiments, the quantification of the relevant volume of the sample by measuring the volume of the relevant volume of the sample optically.

In the method of paragraph MS1, in some embodiments, scale marks are used to assist the quantification of a relevant volume of the sample while the plates are at a closed configuration, wherein some embodiments of the scale markers, their use and measurements, etc. are described in Section 2.

In the method of paragraph MS1, in some embodiments, the quantification of the relevant volume of the sample comprises a step of subtracting the none-sample volume, wherein the none-sample volume is determined, in some embodiments, by the embodiments described in in the disclosures 9-4. A Method for Quantifying Analytes Concentration in a Relevant Volume of a Sample Q5. A method for quantifying analytes in a relevant volume of a sample, comprising:
(a) perform the steps in the method of paragraph Q1; and
(b) measuring, after step (a), a signal related to the analytes from the relevant volume, wherein the relevant volume is at least a portion of an entire volume of the sample.

Q6. A method for quantifying analytes in a relevant volume of a sample, comprising:
(a) perform the steps in the method of paragraph Q2; and
(b) measuring, after step (a), a signal related to the analytes from the relevant volume,
wherein the relevant volume is at least a portion of an entire volume of the sample.

In the method of any of paragraphs Q5-6, in some embodiments, it further comprises a step of calculating the analytes concentration by dividing the signal related to the analytes from the relevant volume of the sample by the volume of the relevant volume.

In the method of any of paragraphs Q5-6, one or both plates further comprise a binding site, a storage site, or both.

In the method of any of paragraphs Q5-6, in some embodiments, the signal related to the analyte is a signal directly from the analytes or a label attached to the analyte.

Q7. A method for quantifying analytes in a relevant volume of a sample, comprising:
(a) perform the steps in the method of paragraph Q1, wherein one or both plates further comprise a binding site; and
(b) measuring, after step (a), a signal related to the analytes from the relevant volume, wherein the relevant volume is at least a portion of an entire volume of the sample.

Q8. A method for quantifying analytes in a relevant volume of a sample, comprising:
(a) perform the steps in the method of paragraph Q2, wherein one or both plates further comprise a binding site; and
(b) measuring, after step (a), a signal related to the analytes from the relevant volume, wherein the relevant volume is at least a portion of an entire volume of the sample.

In the method of any of paragraphs Q7-8, in some embodiments, the signal related to the analyte is a signal directly from the analytes that binds to the binding site or a label attached to the analyte that binds to the binding site.

9.5 A Plate for Use in Quantifying Analyte Concentration in a Relevant Volume in a Sample Q9. A plate for use in quantifying analyte concentration in a relevant volume in a sample, comprising:
a plate that comprises, on its surface, (i) spacers that have a predetermined inter-spacer distance and height, and (ii) a sample contact area for contacting a sample with analyte concentration in a relevant volume to be quantified, wherein at least one of the spacers is inside the sample contact area.

9.6 A Device for Use in Quantifying Analyte Concentration in a Relevant Volume in a Sample The concentration of target analytes and/or entity in a sample can be quantified or controlled, if the number of target analytes and/or entity in the sample are quantified, as well as the relevant volume of the sample is quantified.

Q10. A device for quantifying analyte concentration in a relevant volume in a sample, comprising:
a first plate and a second plate that (a) are movable relative to each other into different configurations and (b) each has a sample contact area for contacting a sample with analyte concentration in a relevant volume to be quantified, wherein one or both of the plates comprise, on its surface(s), spacers that have a predetermined inter-spacer distance and height, and each of the spacers are fixed with respective plates;
wherein one of the configurations is an open configuration, in which: the two plates are separated apart, the spacing between the plates is not regulated by the spacers, and the sample is deposited on one or both of the plates, wherein another of the configuration is a closed configuration, which is configured after the sample deposition in the open configuration; and in the closed configuration: the plates are facing each other, the spacers and the relevant volume of the sample are between the plates, the thickness of the relevant volume of the sample is regulated by the plates and the spacers and is thinner than that when the plates are in the open configuration, and at least one of the spacers is inside the sample; and wherein analyte concentration in the relevant volume of the sample is quantified in the closed configuration, and the relevant volume is at least a portion of an entire volume of the sample.

In the device of any of paragraphs Q9 and Q10, the plate further comprises a binding site, or a storage site, or both. One embodiment of the binding site is a binding site that bind the analytes in the sample.

In the device of any of paragraphs Q9 and Q10, the plate further comprises a or a plurality of scale-markers, wherein some embodiments of the scale-markers described in Section 2.

In the method or the device of any of paragraphs of Q1-10, in some embodiments, the measuring device includes at least one of an imager and a camera.

In the method or the device of any of paragraphs of Q1-10, in some embodiments, the measuring device is configured to image the lateral area of the relevant volume of the sample.

In the method or the device of any of paragraphs of Q1-10, in some embodiments, the measuring device includes a light source to illuminate the lateral area of the relevant volume of the sample.

In the method or the device of any of paragraphs of Q1-10, in some embodiments, the step of calculating the concentration is to divide the total target analytes or the entity by the relevant sample volume.

In the method or the device of any of paragraphs of Q1-10, in some embodiments, measuring signal is to use an optical imager to count the number of target analytes or entity. For example, the measurement can be a use of optical microscope to measure blood cells (red cell, white cells, platelets) in a blood sample.

In the method or the device of any of paragraphs of Q1-10, in some embodiments, measuring the number of target analytes or entity in a sample can be an embodiment of surface-immobilization assay that catch the target analytes or the entity on the surface.

In some embodiments, an apparatus for quantifying a volume of a sample or detecting/quantifying an analyte in a sample comprises any of the devices in paragraphs Q1-10, plus (1) optical imagers, and/or (2) a light source and optical imagers, etc. The optical imager includes a photosensor, optical lenses, filters, polarizers, waveplates, beam splitters, mechanical mounts, or any combination of thereof.

In some embodiments, the measuring of the relevant sample area or volume comprises (i) having a marker on the first plate, the cover plate, between them, or any combination of thereof, (ii) taking optical imaging (e.g. taking a 2D (two-dimensional)/3D (three-dimensional) image of the sample and the image taking can be multiple times with different viewing angles, different wavelength, different phase, and/or different polarization) and (iii) image processing based on the maker and the sample images. The relevant means to be related to the determination of target analyte concentration.

Scanning.

In some embodiments, the reading of a signal from a sample uses a scanning method, where a reader (e.g. photodetectors or camera) reads a portion of the sample (or plate) and then moves to another portion of the sample (or plate), and such process continues until certain pre-specified port of the sample (or plate) being read. The scan reading of a sample covers all part of the sample (or the plate) or a fraction of the sample (or the plate). In some embodiments, the scan reading are assisted by the location markers that indicate a location of the sample (or the plate). One example of the location markers is the periodic spacers, which has a fixed period and location, or the markers for the relevant area which also has predetermined location and size for indicating a location of the sample or plate.

10 Detection and Quantification of Analytes and Others (D)

In certain embodiments, an analyte is detected and/or quantified (i.e. assayed) by measuring a signal related to the analyte, wherein the signal is an optical signal, electrical signal, mechanical signal, chemi-physical signal, or any combination of thereof. In some embodiments, the analyte assaying are performed when the two plates in a CROF device are close to each other. In some embodiments, the analyte assaying are performed when the two plates in a CROF device are separated from each other.

The optical signal includes, but not limited to, light reflection, scattering, transmission, absorption, spectrum, color, emission, intensity, wavelength, location, polarization, luminescence, fluorescence, electroluminescence, chemoluminescence, eletrochemoluminescence, or any combination of thereof. The optical signal is in the form of optical image (i.e. light signal vs location of the sample or device) or a lump sum of all photons coming from a given area or volume. A preferred wavelength of the light is in a range of 400 nm to 1100 nm, a range of 50 nm to 400 nm, a range of 1 nm to 50 nm, or a range of 1100 to 30,000 nm. Another preferred wavelength is in terahertz.

The electrical signal includes, but not limited to, charge, current, impedance, capacitance, resistance, or any combination of thereof. The mechanical signal includes, but not limited to, mechanical wave, sound wave, shock wave, or vibration. The chemi-physical signal includes, but not limited to, PH value, ions, heat, gas bubbles, color change, that are generated in an reaction.

For example, the label is a bead and the label is attached to the label through an analyte specific binding process (e.g. use detection agent to bind the bead to the analyte, use capture agent to capture the analyte with bead, use a capture agent to bind the analyte and then use detection agent to attach the bead, or other approaches. Note the capture and detection agents bind the analyte specifically), then a measurement is used to identify each of the beads that are attached to the analytes, and count them.

In some embodiments, each of the analyte or the beads are sensed and counted by optical means (such as (i) optical labels and reading of the labels, (ii) surface plasmon resonance, (iii) optical interferences, (iv) electrical methods (e.g. capacitance, resistance, impedance, etc.), or others. The sensors can be on the surface of the first plate and/or the second plate.

Certain embodiments may include determining the analyte concentration in (a) surface immobilization assay, (b) bulk assay (e.g., blood cell counting), and (c) others. In some embodiments, the methods of the sample volume, the relevant volume of the sample, or the concentration uses a smart-phone.

In the method or the device of any of paragraphs of Q1-10, in some embodiments, the measuring a signal is to measure the number of the analytes in the sample, or measure the number of a label being attached to the analytes in the sample. In another embodiment of paragraph Q5, the "measuring signal" is to (a) identify each of the analyte or the label attached to each analyte, and (b) count their number.

In some embodiments, the analytes detection is an electrical method when electrodes are put on one or both of the first and second plates (this applies to any of the methods and devices that uses CROF). The electrodes measure the charge, current, capacitance, impedance, or resistance of a sample, or any combination of thereof. The electrodes measure an electrolyte in a sample. The electrodes have a thickness equal or less than the thickness spacer. In some embodiments, the electrode serve as a part of the spacers. The electrodes are made of various conducting materials. A preferred electrode material is gold, silver, aluminum, copper, platinum, carbon nanotubes, or any combination of thereof.

In the method or the device of any of paragraphs of Q1-10, in some embodiments, the measuring uses the devices that is a camera or photodetector plus an optional processor configured to make the measurement.

In the method or the device of any of paragraphs of Q1-10, in some embodiments, the concentration determining devices comprises a processor configured to determine the concentration from the measurements (volume, area, thickness, number of analytes, intensity)

In the method or the device of any of paragraphs of Q1-10, in some embodiments, it further comprising a concentration determining device is configured to determine the concentration of the target analytes in the relevant volume from the measured lateral area, the thickness, and the measured amount of the target molecules.

More on Signal Detection Using Pixelated Reading and Analysis

In present invention, in some embodiments, the signals from the sample, analytes, and entity, binding sites, reagents, CROF plates, or any combinations of thereof are detected and analytes. Some embodiments of the signal detection using pixelated reading and analysis are described in the disclosure, while some other embodiments are described in Publication Number: WO2014144133 A and Application Number: PCT/US2014/028417 (Chou et al, "Analyte Detection Enhancement By Targeted Immobilization, Surface Amplification, And Pixelated Reading And Analysis"), which is incorporated by reference herein for all purposes.

In some embodiments, the signal is electromagnetic signal, including electrical and optical signals with different frequencies, light intensity, fluorescence, chromaticity, luminescence (electrical and chemo-luminescence), Raman scattering, time resolved signal (including blinking). The signals also can be the forces due to local electrical, local mechanical, local biological, or local optical interaction between the plate and the reading device. The signal also includes the spatial (i.e. position), temporal and spectral distribution of the signal. The detection signal also can be absorption.

The analyte include proteins, peptides, DNA, RNA, nucleic acid, small molecules, cells, nanoparticles with different shapes. The targeted analyte can be either in a solution or in air or gas phase. The sensing includes the detection of the existence, quantification of the concentration, and determination of the states of the targeted analyte.

In some embodiments, electric field is used to assist molecular selectivity, or bonding, and detection.

Detection/Reading Methods

In some embodiments of optical detection (i.e. detection by electromagnetic radiation), the methods include, but not limited to, far-field optical methods, near-field optical methods, epi-fluorescence spectroscopy, confocal microscopy, two-photon microscopy, and total internal reflection microscopy, where the target analytes are labelled with an electromagnetic radiation emitter, and the signal in these microscopies can be amplified by the amplification surface of a CROF plate.

In some embodiments, the signal comprises the information of the position, local intensity, local spectrum, local polarization, local phase, local Raman signature of said signals, or any combination of thereof.

In some embodiments, the detection of a signal is to measure a lump-sum signal from an area (i.e. the signal from the area, regardless which location in the area).

In certain embodiments, the detection of signal is to measure an signal image of an area (i.e. signal vs location); namely, the area is divided into pixels and the signal from each pixel of the area is individually measured, which is also termed "PIX" or "pixelated imaging detection". The individual measurement of each pixel can be in parallel or sequential or a mix.

In some embodiments, the reading uses appropriate detecting systems for the signal to be detected in sequence or in parallel or their combination. In a sequential detection, one or several pixels are detected a time, and scanner will be used to move the detection into other areas of the SAL. In a parallel detection, a multipixel detector array, such as imaging camera (e.g. CCD's), will be used to take detect the signals from different pixels at the same time. The scan can be single path or multi-path with a different pixel size for each path. FIG. 2C of PCT/US2014/028417 schematically illustrates pixelated reading on an x, y, z stage.

The pixel size for the reading/detection will be adjusted to for the balance of optical resolution and total reading time. A smaller pixel size will take a longer time for reading/scanning the entire or fraction of the SAL. A typical pixel size is 1 µm to 10 µm in size. The pixel has different shapes: round, square and rectangle. The lower limit of the pixel size is determined by the optical resolution of the microscope system, and the higher limit of the pixel size is determined in order to avoid reading error from the uneven optical response of the imager (optical aberration, illumination uniformity, etc.).

Reading System

Referred to the Figures in of PCT/US2014/028417, an embodiment of a reading system comprises (a) a plate or plates used for CROF; (b) a reading device 205 for producing an image of signals emanating from a surface of said plate, wherein signals represent individual targeted analyte binding events; (c) a device assembly 300 that holds the plate and the imager; (d) an electronics and a data storage 301 for storing said image; and (e) a computer comprising programming for identifying and counting individual binding events in an area of the image.

The device assembly 300 controls or changes the relative position between the plate and the reading device, in at least one of the three (x, y, z) orthogonal directions, for reading the signal. An embodiment of the device assembly comprises a scanner 301. In some embodiments, the scanner 301 scans in in at least one of the three (x, y, z) orthogonal directions.

In some embodiments, the reading device 302 is a CCD camera. In some embodiments, the reading device 302 is a photodetector comprising one or more other optical devices that are selected from optical filters 303, spectrometer, lenses 304, apertures, beam splitter 305, mirrors 306, polarizers 307, waveplates, and shutters. In some embodiments, he reading device 302 is a smartphone or mobile phone, which have the capability of local and remote communications. The reading device collects the position, local intensity, local spectrum, local Raman signature of said signals, or any combination of thereof.

In some embodiments, optical filters 303, light beam splitters 305, optical fibers, a photodetector (e.g. pn junction, a diode, PMT (photomultiplier tube), or APD (Avalanch Photo Diode), imaging camera (e.g. CCD's, or cellphone camera) and spectrometer together with a scanner provided by the device assembly 301 are coupled to a microscope system which uses a far-field confocal setting or a wide-field view setting.

In some embodiments, in confocal setting, the reading is performed by recording the brightness, temporal change and spectral change of one or a few pixels a time and raster scanning the entire interested area of the SAL. In some embodiments, in wide-field view setting, a camera is used to record the brightness and temporal change of the entire or a fraction of SAL area a time. In some embodiments, proper optical filters and light beam manipulators (polarizer, beam splitters, optical fibers, etc.) is need to ensure only the desired signal is collected and detected. FIG. 9 of PCT/US2014/028417 schematically illustrates one arrangement of components for this system. In some embodiments, the analysis comprises of an imaging processing methods, including, not limited to, the methods in Open-CV or Image-J.

Pixelated Analysis (PIX).

In some embodiments of PIX, the signals detected in a pixelated manner are analyzed to determine the number and/or types of the particular molecules at a particular pixel or several pixels, which, in turn is used to quantify the type and/or concentration of the targeted analytes. The term "signal detected in a pixelated manner" refers to the method where the area that has signal(s) is divided into pixels and the signal from each pixel of the area is individually measured, which is also termed "PIX" or "pixelated imaging detection". The individual measurement of each pixel can be in parallel or sequential or a mix.

In some embodiments, the analysis comprises to analyze the spatial, tempo, spectral information of the signal. In some embodiments, the analysis include, but not limited to, statistical analysis, comparison, integration, and others. FIG. 5 of PCT/US2014/028417 shows a flow chart for one embodiment of this method.

11 Labels

One or any combinations of the embodiments of the optical labels described in the entire disclosure applies to all the methods and devices described in the entire description of the present invention.

In some embodiments, a label(s) is attached to a detection agent(s), an analyte(s) or an entity (ties). In certain embodiments, the label is an optical label, an electric label, enzymes that can be used to generate an optical or electrical signal, or any combination of thereof. In certain embodiments, a detection agent(s), an analyte(s) or an entity (ties) are attached a connection molecule (e.g. protein, nucleic acid, or other compounds) which later is attached to a label. In certain embodiments, cells (e.g. blood cells, bacteria, etc.) or nanoparticles are stained by a labels. In some embodiments, an optical label is an object that can generate an optical signal, wherein the generation of the optical signal includes, but not limited to, light (i.e. photon's) reflection, scattering, transmission, absorption, spectrum, color, emission, intensity, wavelength, location, polarization, luminescence, fluorescence, electroluminescence, photoluminescence (fluorescence), chemoluminescence, electrochemiluminescence, or any combination of thereof. In some embodiments, the optical signal is in the form of optical image (i.e. light signal vs location of the sample or device) or a lump sum of all photons coming from a given area or volume. A preferred wavelength of the light is in a range of 400 nm to 1100 nm, a range of 50 nm to 400 nm, a range of 1 nm to 50 nm, or a range of 1100 to 30,000 nm. Another preferred wavelength is in terahertz.

Beads, Nanoparticles, and Quantum Dots.

In some embodiments, the optical label is beads, nanoparticles, quantum dots, or any combination of thereof.

In some embodiments, the diameter of the bead, nanoparticles, or quantum dots is 1 nm or less, 2 nm or less, 5 nm or less, 10 nm or less, 20 nm or less, 30 nm or less, 40 nm or less, 50 nm or less, 60 nm or less, 70 nm or less, 80 nm or less, 100 nm or less, 120 nm or less, 200 nm or less, 300 nm or less, 500 nm or less, 800 nm or less, 1000 nm or less, 1500 nm or less, 2000 nm or less, 3000 nm or less, 5000 nm or less, or a range between any two of the values.

In some embodiments, the beads or quantum dots are used as labels and they are precoated on the plates of CROF and the inner spacing between the two plates are 1 μm or less, 10 μm or less, 50 μm or less, or a range between any two of the values.

In some embodiment, the separation between the beads in a solution
  Diffusion time. (The thickness of the relevant volume of the transfer medium leads to the diffusion time of an optical label across the thickness, to be less than 1 ms,
  The dissolving time can controlled. The control can use photon, heat or other exications and their combinations. The dissolving will not start until an excitation energy is applied.

In some embodiments of the label are nanoparticles that has a diameter of 10 nm or larger. The nanoparticles of such large diameter has less diffusion constant than small molecules (mass<1000 Da) and large molecules (mass=1,000 to 1,000,000 Dalton (da), leading to a longer diffusion time for a given solution and distance. To reduce the diffusion time, is to reduce the diffusion distance.

They have particular advantages over the prior art, when the optical labels are beads or other nanoparticles that have a diameter large than a few nanometers. This is because that the diffusion constant of an object in a liquid is, for the first order approximation, inversely proportional to the diameter of the object (according to Einstein-Stokes equation).

For example, a bead optical label with a diameter of 20 nm, 200, and 2000 nm respectively has a diffusion constant and hence a diffusion time 10, 100, and 1000 times larger and longer than that for a bead of 2 nm. For a typical diffusion distance used in current assays, this would lead to a long saturation incubation time that is in practical for PoC (Point of Care) applications.

However, the present invention has solved the long incubation time for optical labels with a diameter larger than a few nanometers. The present invention has the optical label stored on a plate surface, and then places the storage surface next to binding site with a separate distance (between the two) in sub-millimeter, microns or even nanometer scale and fill the separation gap by a transfer medium (where the stored optical label dissolved into the transfer medium and diffuse to the binding site). The present invention also able to control such small distance uniformly over large binding site area and easily by using spacer technologies.

Labeling the analyte may include using, for example, a labeling agent, such as an analyte specific binding member that includes a detectable label. Detectable labels include, but are not limited to, fluorescent labels, colorimetric labels, chemiluminescent labels, enzyme-linked reagents, multi-color reagents, avidin-streptavidin associated detection reagents, and the like. In certain embodiments, the detectable label is a fluorescent label. Fluorescent labels are labeling moieties that are detectable by a fluorescence detector. For example, binding of a fluorescent label to an analyte of interest may allow the analyte of interest to be detected by a fluorescence detector. Examples of fluorescent labels include, but are not limited to, fluorescent molecules that fluoresce upon contact with a reagent, fluorescent molecules that fluoresce when irradiated with electromagnetic radiation (e.g., UV, visible light, x-rays, etc.), and the like.

In certain embodiments, suitable fluorescent molecules (fluorophores) for labeling include, but are not limited to, IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120),7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-di-isothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM),5-(4,6-dichlorotriazin-2-yl)amino-fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from *Aequoria victoria* or a derivative thereof, e.g., a "humanized" derivative such as Enhanced GFP; a GFP from another species such as *Renilla reniformis, Renilla mulleri,* or *Ptilosarcus guernyi;* "humanized" recombinant GFP (hrGFP); any of a variety of fluorescent and colored proteins from Anthozoan species; combinations thereof; and the like.

In certain embodiments, the dyes can be used to stain the blood cells comprise Wright's stain (Eosin, methylene blue), Giemsa stain (Eosin, methylene blue, and Azure B), May-Grunwald stain, Leishman's stain ("Polychromed" methylene blue (i.e. demethylated into various azures) and eosin), Erythrosine B stain (Erythrosin B), and other fluorescence stain including but not limit to Acridine orange dye, 3,3-dihexyloxacarbocyanine (DiOC6), Propidium Iodide (PI), Fluorescein Isothiocyanate (FITC) and Basic Orange 21 (B021) dye, Ethidium Bromide, Brilliant Sulfaflavine and a Stilbene Disulfonic Acid derivative, Erythrosine B or trypan blue, Hoechst 33342, Trihydrochloride, Trihydrate, and DAPI (4',6-Diamidino-2-Phenylindole, Dihydrochloride).

In certain embodiments, the labeling agent is configured to bind specifically to the analyte of interest. In certain embodiments, a labeling agent may be present in the CROF device before the sample is applied to the CROF device. In other embodiments, the labeling agent may be applied to the CROF device after the sample is applied to the CROF device. In certain embodiments, after the sample is applied to the CROF device, the CROF device may be washed to remove any unbound components, e.g. un bound analyte and other non-analyte components in the sample, and the labeling agent may be applied to the CROF device after the washing to label the bound analyte. In some embodiments, the CROF device may be washed after the labeling agent is bound to the analyte-capture agent complex to remove from the CROF device any excess labeling agent that is not bound to an analyte-capture agent complex.

In certain embodiments, the analyte is labeled after the analyte is bound to the CROF device, e.g., using a labeled binding agent that can bind to the analyte simultaneously as the capture agent to which the analyte is bound in the CROF device, i.e., in a sandwich-type assay. In some embodiments, a nucleic acid analyte may be captured on the CROF device, and a labeled nucleic acid that can hybridize to the analyte simultaneously as the capture agent to which the nucleic acid analyte is bound in the CROF device.

In certain aspects, a CROF device enhances the light signal, e.g., fluorescence or luminescence, that is produced by the detectable label bound directly or indirectly to an analyte, which is in turn bound to the CROF device. In certain embodiments, the signal is enhanced by a physical process of signal amplification. In some embodiments, the light signal is enhanced by a nanoplasmonic effect (e.g., surface-enhanced Raman scattering). Examples of signal enhancement by nanoplasmonic effects is described, e.g., in Li et al, Optics Express 2011 19: 3925-3936 and WO2012/024006, which are incorporated herein by reference. In certain embodiments, signal enhancement is achieved without the use of biological/chemical amplification of the signal. Biological/chemical amplification of the signal may include enzymatic amplification of the signal (e.g., used in enzyme-linked immunosorbent assays (ELISAs)) and polymerase chain reaction (PCR) amplification of the signal. In other embodiments, the signal enhancement may be achieved by a physical process and biological/chemical amplification.

Sensitivity.

In certain embodiments, the CROF device is configured to have a detection sensitivity of 0.1 nM or less, such as 10 pM or less, or 1 pM or less, or 100 fM or less, such as 10 fM or less, including 1 fM or less, or 0.5 fM or less, or 100 aM or less, or 50 aM or less, or 20 aM or less. In certain embodiments, the CROF device is configured to have a detection sensitivity in the range of 10 aM to 0.1 nM, such as 20 aM to 10 pM, 50 aM to 1 pM, including 100 aM to 100 fM. In some instances, the CROF device is configured to be able to detect analytes at a concentration of 1 ng/mL or less, such as 100 pg/mL or less, including 10 pg/mL or less, 1 pg/mL or less, 100 fg/mL or less, 10 fg/mL or less, or 5 fg/mL or less. In some instances, the CROF device is configured to be able to detect analytes at a concentration in the range of 1 fg/mL to 1 ng/mL, such as 5 fg/mL to 100 pg/mL, including 10 fg/mL to 10 pg/mL. In certain embodiments, the CROF device is configured to have a dynamic range of 5 orders of magnitude or more, such as 6 orders of magnitude or more, including 7 orders of magnitude or more.

Reading.

In certain instances, the period of time from applying the sample to the CROF device to reading the CROF device may range from 1 second to 30 minutes, such as 10 seconds to 20 minutes, 30 seconds to 10 minutes, including 1 minute to 5 minutes. In some instances, the period of time from applying the sample to the signal enhancing detector to generating an output that can be received by the device may be 1 hour or less, 30 minutes or less, 15 minutes or less, 10 minutes or less, 5 minutes or less, 3 minutes or less, 1 minute or less, 50 seconds or less, 40 seconds or less, 30 seconds or less, 20 seconds or less, 10 seconds or less, 5 seconds or less, 2 seconds or less, 1 second or less, or even shorter. In some instances, the period of time from applying the sample to the signal enhancing detector to generating an output that can be received by the device may be 100 milliseconds or more, including 200 milliseconds or more, such as 500 milliseconds or more, 1 second or more, 10 seconds or more, 30 seconds or more, 1 minute or more, 5 minutes or more, or longer.

Any suitable method may be used to read the CROF device to obtain a measurement of the amount of analyte in the sample. In some embodiments, reading the CROF device includes obtaining an electromagnetic signal from the detectable label bound to the analyte in the CROF device. In certain embodiments the electromagnetic signal is a light signal. The light signal obtained may include the intensity of light, the wavelength of light, the location of the source of light, and the like. In particular embodiments, the light signal produced by the label has a wavelength that is in the range of 300 nm to 900 nm. In certain embodiments, the light signal is read in the form of a visual image of the CROF device.

In certain embodiments, reading the CROF device includes providing a source of electromagnetic radiation, e.g., light source, as an excitation source for the detectable label bound to the biomarker in the CROF device. The light source may be any suitable light source to excite the detectable label. Exemplary light sources include, but are not limited to, sun light, ambient light, UV lamps, fluorescent lamps, light-emitting diodes (LEDs), photodiodes, incandescent lamps, halogen lamps, and the like.

Reading the CROF device may be achieved by any suitable method to measure the amount of analyte that is present in the sample and bound to the CROF device. In certain embodiments, the CROF device is read with a device configured to acquire the light signal from the detectable label bound to the analyte in the CROF device. In some cases, the device is a handheld device, such as a mobile phone or a smart phone. Any suitable handheld device configured to read the CROF device may be used in the devices, systems and methods in the present invention. Certain device embodiments configured to read the CROF device are described in, e.g., U.S. Provisional Application Ser. No. 62/066,777, filed on Oct. 21, 2014, which is incorporated herein by reference.

In some embodiments, the device includes an optical recording apparatus that is configured to acquire a light signal from the CROF device, e.g., acquire an image of the CROF device. In certain instances, the optical recording apparatus is a camera, such as a digital camera. The term "digital camera" denotes any camera that includes as its main component an image-taking apparatus provided with an image-taking lens system for forming an optical image, an image sensor for converting the optical image into an electrical signal, and other components, examples of such cameras including digital still cameras, digital movie cameras, and Web cameras (i.e., cameras that are connected, either publicly or privately, to an apparatus connected to a network to permit exchange of images, including both those connected directly to a network and those connected to a network by way of an apparatus, such as a personal computer, having an information processing capability). In one example, reading the CROF device may include video imaging that may capture changes over time. For example, a video may be acquired to provide evaluation on dynamic changes in the sample applied to the CROF device.

In certain embodiments, the optical recording apparatus has a sensitivity that is lower than the sensitivity of a high-sensitivity optical recording apparatus used in research/clinical laboratory settings. In certain cases, the optical recording apparatus used in the subject method has a sensitivity that is lower by 10 times or more, such as 100 times or more, including 200 times or more, 500 times or more, or 1,000 times or more than the sensitivity of a high-sensitivity optical recording apparatus used in research/clinical laboratory settings.

In certain embodiments, the device may have a video display. Video displays may include components upon which a display page may be displayed in a manner perceptible to a user, such as, for example, a computer monitor, cathode ray tube, liquid crystal display, light emitting diode display, touchpad or touchscreen display, and/or other means known in the art for emitting a visually perceptible output. In certain embodiments, the device is equipped with a touch screen for displaying information, such as the image acquired from the detector and/or a report generated from the processed data, and allowing information to be entered by the subject.

12 Multiplexing

In any embodiment described herein, the system may be designed for performing a multiplex assay and, as such, may contain multiple storage sites, multiple binding sites, or multiple storage sites and multiple binding sites such that different assays can be performed on different areas on the surface of one of the plates. For example, in one embodiment, in one embodiment, one of the plates may contain multiple binding site that each contain a different capture agent, thereby allowing the detection of multiple analytes in the sample in the same assay. The sites may be spatially separated from, although proximal to, one another.

FIG. 16 schematically illustrates an exemplary embodiment of the present invention, a multiplexed detection in a single CROF device using one binding site one plate and a plurality of storage sites on the other plate. Panel (a) and (b) is a perspective and a cross-sectional view of an exemplary device, respectively. In the exemplary case, the multiplexed CROF device comprises a first plate and a second plate, wherein one surface of the first plate has one binding site; wherein one surface of the second plate has a plurality of storage sites; and wherein different storage sites can have the same detection agent but of different concentrations or can have different detection agents of the same or different concentrations. In some embodiments, the area of the binding site is larger that of each storage site. In some embodiments, the binding site area is larger than the total area of all storage sites, and/or the binding site area is aligned with the storage sites (i.e. they are top each other, namely, the shortest distance between the binding site and a point on the storages are the same or nearly the same).

FIG. 17 schematically illustrates a further exemplary embodiment of the present invention, a multiplexed detection in a single CROF device using one storage site on one plate and multiple binding sites on the other plate. Panel (a) and (b) is a perspective and a cross-sectional view of an exemplary device, respectively. In the exemplary case, the multiplexed CROF device comprises a first plate and a second plate, wherein one surface of the first plate has multiple binding sites; wherein one surface of the second plate has one storage site; and wherein different binding sites can have the same capture agent but of different concentrations or can have different capture agents of the same or different concentrations. In some embodiments, the area of the storage site is larger that of each storage site. In some embodiments, the storage site area is larger than the total area of all binding sites, and/or is aligned with the binding sites (i.e. they are top each other).

FIG. 18 schematically illustrates a further exemplary embodiment of the present invention, a multiplexed detection in a single CROF device with multiple binding sites on one plate and multiple corresponding storage sites on another plate. Panel (a) and (b) is a perspective and a cross-sectional view of an exemplary device, respectively. In the exemplary case, a multiplexed CROF device comprises a first plate and a second plate, wherein one surface of the first plate has a plurality of binding sites; wherein one surface of the second plate has a plurality of corresponding storage sites; wherein each corresponding storage site is located in a location on the second plate that is corresponding to the location of a binding site on the first plate, so that when the plates are placed face-to-face, each binding site overlaps with only one storage site and each storage site overlaps with only one storage site; wherein different storage sites can have the same detection agent but of different concentrations or can have different detection agents of the same or different concentrations; and wherein different storage sites can have the same capture agent but of different concentrations or can have different capture agents of the same or different concentrations.

In certain embodiments, the device of any of FIGS. 10, 11, and 12, wherein the first plate further comprises, on its surface, a first predetermined assay site and a second predetermined assay site, wherein the distance between the edges of the neighboring multiple assay sites is substantially larger than the thickness of the uniform thickness layer when the plates are in the closed position, wherein at least a part of the uniform thickness layer of the sample is over the predetermined assay sites, and wherein the sample has one or a plurality of analytes that are capable of diffusing in the sample. By making the distance between the edges of the neighboring multiple assay sites large than the sample thickness, it makes it possible to have multiple binding sites without fluidically isolated the different portion of a sample, since an saturation incubation of the assay can complete between a significant inter-diffusion between the two neighboring sites. By properly choosing the ratio of the neighboring distance to the sample thickness and properly selecting the measurement time between a time longer than the assay saturation incubation time but less than a time for a significant inter-diffusion between two neighboring sites, one can do multiplexing by CROF without isolating different part of a sample. In some embodiments, the ratio of the neighbor distance to the sample thickness at the closed configuration is 1.5 or larger, 3 or larger, 5 or larger, 10 or larger, 20 or larger, 30 or larger, 50 or larger, 100 or larger, 200 or larger, 1000 or larger, 10,000 or larger, or a range between any two of the values. The ratio is 3 or larger for a preferred embodiment, 5 or larger for another preferred embodiment, 10 or larger for a certain preferred embodiment, 30 or larger for another preferred embodiment, and 100 or larger for another preferred embodiment.

In certain embodiments, the device of any of FIGS. 10, 11, and 12, wherein the first plate has, on its surface, at least three analyte assay sites, and the distance between the edges of any two neighboring assay sites is substantially larger than the thickness of the uniform thickness layer when the plates are in the closed position, wherein at least a part of the uniform thickness layer is over the assay sites, and wherein the sample has one or a plurality of analytes that are capable of diffusing in the sample.

In certain embodiments, the device of any of FIGS. 10, 11, and 12, wherein the first plate has, on its surface, at least two neighboring analyte assay sites that are not separated by a distance that is substantially larger than the thickness of the uniform thickness layer when the plates are in the closed position, wherein at least a part of the uniform thickness layer is over the assay sites, and wherein the sample has one or a plurality of analytes that are capable of diffusing in the sample.

The method or the devices of any of paragraph of U1-6, X-6, P1-8, W1-6, V1-4, UAB1-8, M1-2, S1-2, Q110, and H1 as well as their any combination, wherein the first and second plate further comprise the binding site(s) and the storage site, as described in FIG. 10, FIG. 11, or FIG. 12 for multiplexed detection.

In these embodiments the device may for parallel, multiplex, assaying of a liquid sample without fluidic isolation (i.e., without their being a physical barrier between the assay regions). This device may comprise a first plate and a second plate, wherein: i. the plates are movable relative to each other into different configurations; one or both plates are flexible; ii. one or both of the plates comprise spacers that are fixed with a respective plate; and the spacers have a predetermined substantially uniform height and a predetermined constant inter-spacer distance; iii. each of the plates has, on its respective surface, a sample contact area for contacting a sample that contains a sample that contains one or more target analytes which is capable of diffusing in the sample, iii. the first plate has, on its surface, one or a plurality of binding sites that each has a predetermined area comprising a capture agent that binds and immobilizes a corresponding target analyte of the sample; and iv the second plate has, on its surface, one or a plurality of corresponding storage sites that each has a predetermined area and comprises a detection agent of a concentration that, upon contacting the sample, dissolves into the sample and diffuses in the sample, wherein each capture agent, target analyte and corresponding detection agent is capable of forming a capture agent-target analyte-detection agent sandwich in a binding site of the first plate; wherein one of the configurations is an open configuration, in which: the two plates are either partially or completely separated apart, the spacing between the plates is not regulated by the spacers, and the sample is deposited on one or both of the plates, and wherein another of the configurations is a closed configuration which is configured after the sample deposition in the open configuration; and in the closed configuration: i. at least part of the sample is compressed into a layer of uniform thickness that is in contact with and confined by the inner surfaces of the two plates and that covers the one or a plurality of binding sites and the one or a plurality of storage sites, ii the one or a plurality of corresponding storage sites are over the one or a plurality of binding sites, and iii. the uniform thickness of the layer is regulated by the spacers and the plates, is less than 250 µm, and is substantially less than the linear dimension of the predetermined area of each storage site; and iv. there is no fluidic isolation between the binding site and/or the storage sites, wherein the separation between the edges of the neighboring storage sites and the separation between the edges of the neighboring binding sites are larger than the distance that a target analyte or detection agent can diffuse in the relevant time, and wherein there is no fluidic isolation between the binding site sites and/or the storage sites.

In some embodiments, the first plate has, on its surface, a plurality of (at least 2, at least 4 or at least 16 or more) of the binding sites.

In some embodiments, each of said plurality of binding sites binds to a different target analyte.

In some embodiments, the second plate has, on its surface, a plurality (at least 2, at least 4 or at least 16 or more) of the corresponding storage sites.

In some embodiments, each of the plurality of corresponding storage sites binds to a different target analyte.

In some embodiments, the first plate has, on its surface, a plurality of said binding sites and the second plate has, on its surface, a plurality of said corresponding storage sites, wherein each binding site faces a corresponding storage site when the plates are in the closed configuration.

In some embodiments, the first plate has, on its surface, a plurality of said binding sites and the second plate has, on its surface, a storage site, wherein at least some of the binding sites face an area in the storage site when the plates are in the closed configuration.

In some embodiments the first plate has, on its surface, a binding site and the second plate has, on its surface, a plurality of storage sites, wherein at least some of the storage sites face an area in the binding site when the plates are in the closed configuration.

In some embodiments the first plate has, on its surface, a plurality of binding sites, wherein the binding sites contain different capture agents that bind and immobilize the same target analyte.

In some embodiments the first plate has, on its surface, a plurality of binding sites, wherein the binding sites contain the same capture agent.

In some embodiments, the capture agent is at different densities in the different binding sites. These embodiments may be used to provide a way to quantify the amount of analyte in a sample.

In some embodiments, there is a separation between two neighboring binding sites or two neighboring storage sites, and the ratio of the separation to the sample thickness in the closed configuration is at least 3, e.g., at least 5, at least 10, at least 20 or at least 50.

In some embodiments, the inter-spacer distance is in the range of 1 µm to 120 µm.

In some embodiments, the flexible plates have a thickness in the range of 20 µm to 250 µm (e.g., in the range of 50 µm to 150 µm) and Young's modulus in the range 0.1 to 5 GPa (e.g., in the range of 0.5-2 GPa).

In some embodiments, the thickness of the flexible plate times the Young's modulus of the flexible plate is in the range 60 to 750 GPa-µm.

In some embodiments, this method may comprise (a) obtaining a sample that contains one or more target analytes, which are capable of diffusing in the sample; (b) obtaining a first and second plates that are movable relative to each other into different configurations, wherein: i. one or both of the plates comprise spacers that are fixed with a respective plate and one or both plates are flexible, ii. the spacers have a predetermined substantially uniform height and a predetermined constant inter-spacer distance, iii. the first plate has, on its surface, one or a plurality of binding sites that each has a predetermined area comprising a capture agent that binds and immobilizes a corresponding target analyte of (a); and iv. the second plate has, on its surface, one or a plurality of corresponding storage sites that each has a predetermined area and comprises a detection agent of a concentration that, upon contacting the sample, dissolves into the sample and diffuses in the sample, wherein each capture agent, target analyte and corresponding detection agent is capable of forming a capture agent-target analyte-detection agent sandwich in a binding site of the first plate; (c) depositing the sample on one or both of the plates when the plates are configured in an open configuration, wherein the open configuration is a configuration in which the two plates are either partially or completely separated apart and the spacing between the plates is not regulated by the spacers; (d) after (c), compressing the sample by bringing the two plates into a closed configuration, wherein the closed configuration is a configuration in which: i. at least part of the sample is compressed into a layer of uniform thickness that is in contact with and confined by the inner surfaces of the two plates and that is in contact with the one or a plurality of binding sites and the one or a plurality of storage sites, ii the one or a plurality of corresponding storage sites are over the one or a plurality of binding sites, and iii. the uniform thickness of the layer is regulated by the spacers and the plates, is less than 250 μm, and is substantially less than the linear dimension of the predetermined area of each storage site; (e) after (d) and while the plates are in the closed configuration, either: (1) incubating the sample for a relevant time length and then stopping the incubation; or (2) incubating the sample for a time that is equal or longer than the minimum of a relevant time length and then assessing, within a time period that is equal or less than the maximum of the relevant length of time, the binding of each target analyte to a binding site; wherein the relevant time length is:

i.

equal to or longer than the time that it takes for a target analyte of (a) to diffuse across the thickness of the uniform thickness layer at the closed configuration; and ii. significantly shorter than the time that it takes a target analyte of (a) to laterally diffuse across the smallest linear dimension of the predetermined area of a storage site or binding site; thereby producing a reaction in which, at the end of the incubation in (1) or during the assessing in (2), the majority of the capture agent-target analyte-detection agent sandwich bound to each binding site is from a corresponding relevant volume of the sample; wherein the incubation allows each target analyte to bind to a binding site and a detection agent, wherein the corresponding relevant volume is a portion of the sample that is above the corresponding storage site at the closed configuration, wherein the separation between the edges of the neighboring storage sites and the separation between the edges of the neighboring binding sites are larger than the distance that a target analyte or detection agent can diffuse in the relevant time, and wherein there is no fluidic isolation between the binding site sites and/or the storage sites.

Any embodiment of the multiplex assay device described above may be used in this method.

13 Quantification by Correcting Effects Generated by None-Sample Volume (C)

In a CROF process, often a sample is mixed with a none-sample-volume(s) which is due to objects that are not the sample, that include, but not limited to, spacers, air bubbles, dusts, or any combinations of thereof. The air bubbles or dust can be introduced using the sample deposition or other process in the CROF process. These none-sample objects occupy volume and inside the sample, which should be corrected in determine a relevant volume (a volume of interest) of a sample. One aspect of the present invention is to correct the effects generated by the none-sample volume inside a relevant volume of the sample between two plates, where the thickness of the relevant volume is regulated by spacers.

C1. A method for correcting the effects generated by a none-sample material in determining a relevant volume of a sample between two plates, comprising:
(a) obtaining a sample, wherein a relevant volume of the sample is to be quantified;
(b) obtaining two plates that are movable relative to each other into different configurations, wherein one or both of the plates comprise spacers and the spacers have a predetermined inter-spacer distance and height, and each of the spacers is fixed with its respective plate;
(c) depositing, when the plates are configured in an open configuration, the sample on one or both of the plates; wherein the open configuration is a configuration in which the two plates are partially or completely separated apart and the spacing between the plates is not regulated by the spacers;
(d) after (c), bringing the plates into a closed configuration, wherein, in the closed configuration: the plates are facing each other, the spacers and the relevant volume of the sample are between the plates, the thickness of the relevant volume of the sample is regulated by the plates and the spacers and is thinner than the maximum thickness of the sample when the plates are in the open configuration, and the relevant volume may contain a volume of a none-sample material;
(e) measuring, while the plates are in the closed configuration, (i) the lateral area of the relevant volume of the sample and (ii) the volume of the none-sample material; and
(f) calculating the relevant volume of the sample by using the thickness of the relevant volume regulated by the spacers and correcting the effects of a none-sample material;

wherein the relevant volume is at least a portion of an entire volume of the sample, and the none-sample materials are the materials that are not from the sample.

the measuring of the none-sample volume is by imaging of the sample between the two plates.

14 Precision Quantification by Double Checking the Spacing

In a CROF, for a given set of conditions, even the spacers and the plates can give a predetermining sample thickness at a closed configuration, the actual set of conditions during a particular CROF may be different from the expected, which lead to errors in the predetermined final sample thickness. To reduce such errors, one aspect of the present invention is to double check the final sample thickness at a closed configuration.

C2. A method for determining and checking a thickness of a relevant volume of a sample between two plates, comprising:
(a) obtaining a sample, wherein a relevant volume of the sample is to be quantified;
(b) obtaining two plates that are movable relative to each other into different configurations, wherein one or both of the plates comprise spacers and the spacers have a predetermined inter-spacer distance and height, and each of the spacers is fixed with its respective plate;
(c) depositing, when the plates are configured in an open configuration, the sample on one or both of the plates; wherein the open configuration is a configuration in which the two plates are partially or completely separated apart and the spacing between the plates is not regulated by the spacers;
(d) after (c), bringing the plates into a closed configuration, wherein, in the closed configuration: the plates are facing each other, the spacers and the relevant volume of the sample are between the plates, the thickness of the relevant volume of the sample is regulated by the plates and the spacers and is thinner than the maximum thickness of the sample when the plates are in the open configuration, and the relevant volume may contain a volume of a none-sample material;

(e) measuring, while the plates are in the closed configuration, (i) the lateral area of the relevant volume of the sample and (ii) the volume of the none-sample material; and
(f) calculating the relevant volume of the sample by correcting the effects of a none-sample material;
wherein the relevant volume is at least a portion of an entire volume of the sample, and the none-sample materials are the materials that are not from the sample.

15 Wash (WS)

In the present invention, one or any combinations of the embodiments of the plate pressing and holding described herein are used in all the methods and devices described in the entire description of the present invention.

A method for a wash step in assaying, comprising:
(a) Performing the steps in one or any combination of the methods described in above and
(b) washing away the sample or the transfer media between the plates.

In the method that uses CROF, the wash is performed by keep the plates in the closed-configuration.

In the method that uses CROF, the wash is performed by separating the plates from the closed-configuration.

16 Assays with Multiple Steps (MA)

In the present invention, the embodiments descripted by the disclosures (i.e. all sections) can be used in a combined (a) by combining one embodiment with other embodiment(s), by using the same embodiment(s) more than one times, and (c) any combination of (a) and (b).

MA1. A method for assaying an analyte in a sample, comprising:
(a) obtaining a sample with an analyte;
(b) performing the method that uses CROF; and
(c) separating the plates and performing the method that uses CROF.

In the method of paragraph MA1, in some embodiments, it further comprises, after the step (c) of MA1, a step of repeating the same steps of all the steps in the method of MA1 at least once.

MA2. A method for assaying an analyte in a sample, comprising:
(a) obtaining a sample with an analyte;
(b) performing the method that uses CROF;
(c) separating the plates and performing the method (washing) that uses CROF; and
(d) performing the method that uses CROF.

In the method of paragraph MA2, in some embodiments, it further comprises, after the step (d) in MA2, a step of repeating the same steps of all the steps in the method of MA2 at least once.

In the method of paragraph MA2, in some embodiments, it further comprises, after the step (c) in MA2, a step of repeating the same steps of all the steps in the method of MA1 at least once.

MA3. A kit for assaying an analyte in a sample, comprising:
a first CROF device that uses CROF; and
a third plate that, when the plates of the first CROF device are separated, combines with one of the plates of the first CROF device to form a second CROF device.

MA4. A kit for assaying an analyte in a sample, comprising:
a first CROF device that uses CROF;
at least one binding site or storage site that is on the sample contact area of the plate of a CROF device; and
a third plate that, when the plates of the first CROF device are separated, combines with one of the plates of the first CROF device to form a second CROF device;
wherein the binding site binds a target analyte to the plate surface, and the storage site has a reagent that, upon in touch with the sample, can be dissolved into the sample and diffuse in the sample.

The imaging may comprise a use of a smart phone. The methods of this section may further comprise a step of illumination by a light source. The light source may be a laser, LED, a lamp, or a camera flash light.

A Kit (MQXA) for Performing Assay for Detecting a Target Entity in a Sample

A kit for assaying a target entity in a sample, may comprise:
a. a first plate, wherein one surface of the first plate has one or a plurality of binding site(s) that can immobilize a target entity and the binding site has binding partner that binds the target entity;
b. a cover plate;
c. a sample in the inner space between the cover plate and the first plate,
wherein the sample contains said target entity that is mobile in the sample, the shape of sample is deformable, the first plate and the second plate are movable relative to each other, the shape of the sample is substantially conformal to the inner surfaces, at least a part of the sample is in contact to the binding site, and the inner spacing is, during incubation, less than certain distance. the sample is in contact with said binding sites;
d. an imaging device that can image the first plate surface and/or the cover plate surface; and
e. a measuring device that can measure the spacing of the inner space.

The methods of this section may include use of a smart phone. The methods of this section may include use of an illuminating device. The illuminating device may comprise a laser, LED, a lamp, or a camera flash light.

17 Plate Pressing and Holding (H)

Compressing Forces.

In a CROF process, forces are used to compress the two plates to bring the plates from an open configuration to a closed configuration. The compressing forces reduce the spacing between the inner surfaces of the plates and hence a thickness of the sample that is between the plates. In the present invention, the compressing forces include, but not limited to, mechanical force, capillary forces (due to surface tensions), electrostatic force, electromagnetic force (including the light), and any combination of thereof.

In some embodiments of bring the plates from an open configuration to a closed configuration, an external force is applied to push the first plate and the second plate to toward each other.

In some embodiments of bring the plates from an open configuration to a closed configuration, an external pressure is applied to outside the first plate and the second plate to push the plates toward each other, and the pressure is higher than the pressure inside of the plate. A device is used to make the pressure of outside the plates higher than that inside the plate. The device include, in limited to, a sealing device.

In some embodiments, the compress force is at least partially provided by the capillary force, which is due to a liquid between the first plate and the second plate and the corresponding surface tensions and interactions with the plates. In some embodiments, the liquid is the sample itself, or the sample mixed with liquid. In certain embodiments, capillary force is used together with other forces. In many cases, a sample is often in liquid and the surface tensions are suited for inserting a capillary force. In some embodiments, the sample deformation by the plates can automatically stop when the capillary force equals to the force needed to deform the sample.

In certain embodiments, the compressing force (hence the sample deformation) is created by isolating the pressure between the first plate and the second plate (inside pressure) from that outside of the plates (outside pressure), and then make the inside pressure lower than the outside pressure. The isolation can be done using a vacuum seal or other devices.

In some embodiments, it is a combination of the methods described above.

Gradual Pressing.

In certain embodiments, the compressing force to bring the plates to a closed configuration is applied in a process, termed "gradual pressing", which comprises: pressing (i.e. applying the compressing the force) is applied at one location of the plate(s) first, then is applied gradually to other locations of the sample. In some embodiments of the gradual pressing, the compressing force (except the capillary forces by the sample itself) at one location is, after deformed the sample to a desired thickness at that location, (i) maintained during the entire process of the pressing and the sample deformation, (ii) removed while other locations being pressed, or (iii) a use of (i) for certain part of the plates and a use of (ii) for other part of the sample.

In one embodiment of the gradual pressing, a roller is being used to press the first plate and the second plate (the sample is between the plates, and the plates are slightly flexible) against another roller or a flat surface.

In another embodiment, the human fingers are the tool of the pressing the plates (hence the sample). The pressing is one part of human hand against another part of human body (including another part of human hand) or a human hand against an object (e.g. a table surface). In one embodiment, the pressing starts at one location of the sample and gradual moved to other locations of the sample.

In one embodiment of the gradual pressing, a pressed air jet is first directed to a location (e.g. the center) of the plate pair (which is between the first plate and the second plate, one of the plates is slightly flexible) and the pressure is gradually extended to other part of the plate pair. In another embodiment, one or both of the first plate and the second plate is flexible and is in contact with one location of the sample, then a capillary force in that location pulls the plate pair together (toward to each other) to deform the sample.

Advantage of the gradual pressing include: it allows one to use less force to deform the sample (because for the same force, the smaller press area, the larger the pressure); it helps motion (deformation) of the sample, and/or it reduces air bubble in the sample. The larger pressure is, the more sample deformation will be. A gradual pressing can improve the thickness uniformity of the deformed sample.

Pressing Devices.

The devices for asserting the compressing force(s) for the sample deformation in CROF have several implementations. Some embodiments are to use human hand to press, for example, to press by human fingers. Certain embodiments are to use a press device, where the press device includes, but not limited to, a human hand(s), a mechanical clip, a mechanical press, mechanical clamp, a mechanical slider, a mechanical device, ab electromagnetic device, roller that rolls on a surface, two rollers against each other, fluidic press, a hydraulic device, or any combination of thereof. Certain embodiments are use pressured liquid (including pressed air) to press the first plate and/or the second plate directly or indirectly. "Directly" means the pressured liquid is applied directly on the first plate and/or the second plate; and the "indirectly" means it is applied through a third object. Certain embodiments in pressing use a combination of the above embodiments of pressing devices and methods.

Furthermore, in some embodiments of the sample deformation, the pressing and the sample deformation are monitored. The monitoring can be used to control the pressing and the sample deformation. The monitoring of the deformation include, but not limited to, a mechanical method, electrical, optical, chemical, magnetic, and any combination of thereof. The mechanical methods include, but not limited to, mechanical gauges, spacer (mechanical stoppers, more discussed below), and sound waves.

In CROF, the spacing control device comprises mechanical press, mechanical translation stages, human fingers, liquid that provide capillary forces that pulls the plates toward each other, liquid (including air) that applies a pressure on the plates, or a combination of thereof.

In certain embodiments, the mechanical stages (translational and/or rotational) are used for the sample deformation and sample thickness control and work together with the monitoring systems.

In some embodiments, the compressing force is at least partly supplied by a press (which is a device that bring the plates to a closed configuration) configured to press the plates together into the closed configuration.

In some embodiments, the plate pressing is to use a human hand. The human can be the person being tested or a person who perform the test, or a person who collecting the sample.

In some embodiments, the plate pressing is to hold the two plates together is to use a capillary force. The capillary force is generated by making at least a portion of the inner surface of one plate or both hydrophilic. With a proper capillary force, the two plates is able to maintain the same plate-spacing and the same thickness of the relevant volume of the sample as that when the plates initially in the closed configuration, even a part or all of the forces (except the capillary force) that were used to compress the plate to the close configuration is removed.

In some embodiments, the device that applies a compressing force on the outer surface of the plates to reducing the plate inner surface spacing comprise a contacting surface that is comfortable to the outer surfaces of the plate, wherein the contacting surface of the device is the surface of the device that contacts the outer surface of the plates, and the "conformable to the outer surface of the plate" means that the device surface can deform, during the compressing, it shape to conform the shape of the plate outer surface. In one exemplary embodiment, the compressing device is human figures. In another exemplary embodiment, the compressing device has a contacting surface made of soft plastics or rubbers.

Self-Holding (Maintaining the Final Sample Thickness after Removing Compressing Forces).

In some embodiments of pressing in CROF, after the sample deformation at a closed configuration, some of the compressing forces are removed and the sample maintains the same final sample thickness as the compression forces still exist. Such situation is termed "self-holding". One reason for self-holding is that after removing the compressing forces that were inserted from outside of the plate pair, there are still other forces exist between the inner surfaces of the plates, such as a capillary force, which hold the plate pair together. The capillary force is the due to the wetting properties of the sample on the plates.

To have self-holding, one needs to control the plate surface wetting properties, the total contact area of the sample to the plates, the final sample thickness at a closed configuration, or a combination of thereof.

In some embodiments to achieve self-holding, one or both inner surfaces of the plates is hydrophilic. Namely, it is either one of plates have an inner surface that is hydrophilic or both of the plates have an inner surface that is hydrophilic.

The capillary force depends on the radius curvature of the liquid surface, smaller the curvature and higher the capillary force. A smaller curvature can be achieved by using smaller spacing between the two plates (i.e. plate pair) and hence a smaller sample thickness. In some embodiments, a final sample thickness for achieving self-holding is 10 nm or less, 100 nm or less, 100 nm or less, 500 nm or less, 1 µm (micrometer) or less, 2 µm or less, 3 µm or less, 5 µm or less, 10 µm or less, 20 µm or less, 50 µm or less, 70 µm or less, 100 µm or less, 150 µm or less, 300 µm or less, 500 µm or less, 700 µm or less, 1000 µm or less, 1200 µm or less, or a range between any two of the values.

In some embodiments, the area of the sample in contract with the plates for self-holding is at most 10 $\mu m^2$, at most 100 $\mu m^2$, at most 200 $\mu m^2$, at most 500 $\mu m^2$, at most 1000 $\mu m^2$, at most 2000 $\mu m^2$, at most 5000 $\mu m^2$, at most 8,000 $\mu m^2$, at most 0.01 $mm^2$, at most 0.05 $mm^2$, at most 0.1 $mm^2$, at most 0.5 $mm^2$, at most 1 $mm^2$, at most 5 $mm^2$, at most 10 $mm^2$, at most 50 $mm^2$, at most 100 $mm^2$, at most 500 $mm^2$, at most 1,000 $mm^2$, at most 2,000 $mm^2$, at most 5,000 $mm^2$, at most 10,000 $mm^2$, at most 100,000 $mm^2$, or a range between any two of the values.

In some embodiments, one or both of the plate inner surface's wetting properties is modified for better self-holding.

HS.1 In some embodiments, in a CROF process, a device is used to insert a compressing force to bring the plates into a closed configuration, and after the closed configuration is reached, the compressing force by the device is removed and the sample thickness and the inner surface spacing of the plates are remained approximately the same as that before removing the compressing force by the device. In some embodiments, in the methods of previous paragraph, it further comprises a step of reading a signal from the plates or between the plates, wherein the signal includes, but not limited to, a signal related to analytes, entity, labels, sample volume, concentration of a matter (i.e. chemicals), or any combination of thereof.

In the method of paragraph SH.1, the device is a human hand(s), a mechanical clip, a mechanical press, mechanical clamp, a mechanical slider, a mechanical device, ab electromagnetic device, roller that rolls on a surface, two rollers against each other, fluidic press, a hydraulic device, or any combination of thereof.

In the method of paragraph SH.1, in some embodiments, "the sample thickness and the inner surface spacing of the plates are remained approximately the same as that before removing the compressing force by the device" means that the relative difference of the sample thickness and the plate inner surface spacing before and after removing the compressing force is 0.001% or less, 0.01% or less, 0.1% or less; 0.5% or less, 1% or less, 2% or less, 5% or less, 8% or less, 10% or less, 15% or less, 20% or less, 30% or less, 40% or less, 50% or less, 60% or less, 70% or less, 80% or less, 90% or less, 99.9% or less, or a range between any two of the values.

In the method of paragraph SH.1, in some embodiments, the sample thickness and the inner surface spacing of the plates after removing the compressing force by the device care predetermined, wherein predetermined means that the thickness and the spacing after removing the compressing force is known before applying the compressing force for a given compressing conditions.

H1. A method for reducing the thickness of a relevant volume of a sample and maintain the reduced thickness, comprising:
  (a) obtaining a sample, wherein a thickness of a relevant volume of the sample is to be reduced;
  (b) obtaining two plates that are movable relative to each other into different configurations, wherein one or both of the plates comprise spacers and the spacers have a predetermined inter-spacer distance and height, and each of the spacers is fixed with its respective plate;
  (c) depositing, when the plates are configured in an open configuration, the sample on one or both of the plates; wherein the open configuration is a configuration in which the two plates are either partially or completely separated apart and the spacing between the plates is not regulated by the spacers;
  (d) after (c), spreading the sample by using a pressing device that brings the plates into a closed configuration, wherein, in the closed configuration: the plates are facing each other, the spacers and the relevant volume of the sample are between the plates, the thickness of the relevant volume of the sample is regulated by the plates and the spacers and is thinner than the maximum thickness of the sample when the plates are in the open configuration, and at least one of the spacers is inside the sample; and
  (e) after (d), releasing the device, wherein after releasing the pressing device, the spacing between the plates remains the same as or approximately same as that when the device is applied.
    wherein the relevant volume is at least a portion of an entire volume of the sample.

In the method of paragraph H1, the approximately same as the spacing between the plates is at most 1%, at most 2%, at most 5%, at most 10%, at most 20%, at most 50%, at most 60%, at most 70%, at most 80%, at most 90%, or a range between any two of the values.

For example, in CROF, a human hand or hands are used to compressed two plate to a closed position, then the hand(s) and hence the compressing force by hand(s) are removed, but the final sample thickness is still the same as that when the compressing force by hands exist.

18 Other Combinations

In the present invention, each of the embodiments in the disclosures (i.e. all sections) can be used (a) alone, (b) combined with other embodiment(s), (c) multiple times, and (d) any combination of (a) to (c).

The methods and devices in the present invention disclosed can be used alone or any combination of thereof. The term a "QMAX" method or device refers to a method or device of the embodiments described here.

In some embodiments, the methods and devices in the present invention disclosed can be used in the form of Q, X, A, M, QX, QA, QM, XA, XM, AM, QXA, QAM, XAM, and QXAM.

Some embodiments of application of the Q, X, A, and M to surface immobilization assay, comprising
a. having a first plate, wherein the first plate surface has at least one well of a known depth and volume, and bottom surface of the well has one or a plurality of binding site(s) that can immobilize a target entity in a sample;
b. depositing, into the well, the sample of a volume approximately the same as the well volume, wherein the sample contains the targeted entity, the targeted entity is mobile in the sample, the shape of sample is deformable, and the sample covers only a part of the well (hence have a simple thickness higher than the well depth);
c. having a cover plate;
d. facing the first plate and the cover plate to each other, wherein the sample is between the inner surfaces of the first plate and the second plate;
e. reducing the sample thickness by reducing the spacing between the inner surfaces of the first plate and the second plate; and
f. Incubating the sample at the reduced sample thickness for a period of time;

One variation of these methods is to apply one or more of the above steps to 96 well plates or other well plates.

The methods and devices in the present invention disclosed in Section 1, 2, 3, and 5, can be used alone or any combination of thereof. Specifically, we use Q for the inventions disclosed in Section 1 and 2, A for the inventions disclosed in Section 3 and 5, X for the inventions disclosed in Section 4 and 5, and M for the inventions disclosed in Section 6. Hence the methods and devices in the present invention disclosed in Section 1, 2, 3, and 5, can be used in the form of Q, X, A, M, QX, QA, QM, XA, XM, AM, QXA, QAM, XAM, and QXAM.

Some embodiments of application of the Q, X, A, and M to surface immobilization assay, comprising
a. having a first plate, wherein the first plate surface has at least one well of a known depth and volume, and bottom surface of the well has one or a plurality of binding site(s) that can immobilize a target entity in a sample;
b. depositing, into the well, the sample of a volume approximately the same as the well volume, wherein the sample contains the targeted entity, the targeted entity is mobile in the sample, the shape of sample is deformable, and the sample covers only a part of the well (hence have a simple thickness higher than the well depth);
c. having a cover plate;
d. facing the first plate and the cover plate to each other, wherein the sample is between the inner surfaces of the first plate and the second plate;
e. reducing the sample thickness by reducing the spacing between the inner surfaces of the first plate and the second plate; and
f. Incubating the sample at the reduced sample thickness for a period of time.

One variation of these methods is to apply one or more of the above steps to 96 well plates or other well plates.

Several embodiments of the methods, devices, and systems combine one or more of the features of sample volume quantification (Q), reagents addition (A), and/or assay acceleration (X) (and may be referred to as the corresponding acronyms QA, QX, AX, and QAX). Some experimental demonstrations of Q, A, X, QA, QX, AX, and QAX methods and devices are described below.

19 Reagents

The term "reagents" refers to, unless stated otherwise, one or more of biological agents, biochemical agents, and/or chemical agents. For example, reagents may include capture agents, detection agents, chemical compounds, optical labels, radioactive labels, enzymes, antibodies, proteins, nucleic acids, DNA, RNA, lipids, carbohydrates, salts, metals, surfactants, solvents, or any combination of thereof.

In some embodiments, the reagents on a plate in the form of liquid, solid, molecular vapor, or a combination of thereof. The deposition of reagent, include, but are not limited to, depositing, placing, printing, stamping, liquid dispensing, evaporation (thermal evaporation, vapor evaporation, human breathing), chemical vapor deposition, and/or sputtering. Different reagents can be in different locations. Reagents may be printed and/or deposited as small dots of reagents.

In some embodiments, the reagents are deposited on a plate in a liquid or vapor form first, then are dried to become dry reagents on the plate before a CROF process.

Controlling Reagents Releasing Time.

A-methods may further comprise a step of controlling the reagent release time (i.e. the time measures how fast a reagent can be dissolved in a sample. Some embodiments in controlling the reagent release time of a reagent comprises a step of mixing or coating on top of the reagent a or several "releasing control material(s)" that affect the release (into the sample) of the reagent. In some embodiments, the releasing control material can be another reagent. For example, there are two reagents A and B, the reagent A is coated on top of the reagent B, under certain conditions, the reagent A will be dissolved into the sample before the reagent B.

Furthermore, the surface properties of the first plate and the second plate may be used to control the reagent release. One example is to control the surface wetting properties. For many reagents, a hydrophobic surface binds the reagent well, hence leading to slow release or no release of the reagent into the sample (depending upon how thick is the reagent layer), while a hydrophilic surface binds the reagent poorly hence leading a fast release into the sample.

Drying of Reagents.

In some embodiments, after the reagent deposition step (c) but before the sample deposition step (d), A-methods further comprise a step of drying some or all of the reagents deposited in the step (c).

Location of Reagents.

Reagents may be applied and/or arranged on one or both of the plates. Reagents may be in storage sites (locations) on the plate(s), with each storage site including one or more reagents. Different storage sites may include different reagents, the same reagents, or one or more common reagents.

Control Concentration of Added Reagents. In some embodiments, the methods may further comprise a step of controlling the concentration of the added reagents by controlling the samples thickness over the storage sites (i.e., the surface with reagents).

The reagent used in the present invention may be any suitable reagent required for an assay, e.g., a labeled or unlabeled antibody, a labeled or unlabeled nucleic acid, an enzyme that may or may not contain an affinity moiety, etc. In some embodiments and as noted above, the stored reagent may be a component of an assay designed to test a blood or other liquid sample for the presence of an analyte. For example, choride ions can be measured by any of the following protocols, and components of these assays may be present in a storage site: Colorimetric methods: chloride ions displace thiocyanate from mercuric thiocyanate. Free thiocyanate reacts with ferric ions to form a colored complex— ferric thiocyanate, which is measured photometrically. Coulometric methods: passage of a constant direct current between silver electrodes produces silver ions, which react with chloride, forming silver chloride. After all the chloride combines with silver ions, free silver ions accumulate, causing an increase in current across the electrodes and indicating the end point to the reaction. Mercurimetric methods: chloride is titrated with a standard solution of mercuric ions and forms HgCl2 soluble complex. The end point for the reaction is detected colorimetrically when excess mercury ions combine with an indicator dye, diphenylcarbazon, to form a blue color. Likewise, magnesium can be measured colorimetrically using calmagite, which turns a red-violet color upon reaction with magnesium; by a formazan dye test; emits at 600 nm upon reaction with magnesium or using methylthymol blue, which binds with magnesium to form a blue colored complex. Likewise, calcium can be detected by a colorimetric technique using O-Cresolphtalein, which turns a violet color upon reaction of O-Cresolphtalein complexone with calcium. Likewise, Bicarbonate can be tested bichromatically because bicarbonate (HCO3$^-$) and phosphoenolpyruvate (PEP) are converted to oxaloacetate and phosphate in the reaction catalyzed by phosphoenolpyruvate carboxylase (PEPC). Malate dehydrogenase (MD) catalyzes the reduction of oxaloacetate to malate with the concomitant oxidation of reduced nicotinamide adenine dinucleotide (NADH). This oxidation of NADH results in a decrease in absorbance of the reaction mixture measured bichromatically at 380/410 nm proportional to the Bicarbonate content of the sample. Blood urea nitrogen can be detected in a colorimetric test in which diacetyl, or fearon develops a yellow chromogen with urea and can be quantified by photometry, or multiusing the enzyme urease, which converts urea to ammonia and carbonic acid, which can be assayed by, e.g., i) decrease in absorbance at 340 nm when the ammonia reacts with alpha-ketoglutaric acid, ii) measuring the rate of increase in conductivity of the solution in which urea is hydrolyzed. Likewise, creatinine can be measured colorimetrically, by treated the sample with alkaline picrate solution to yield a red complex. In addition, creatine can be measured using a non-Jaffe reaction that measures ammonia generated when creatinine is hydrolyzed by creatinine iminohydrolase. Glucose can be measured in an assay in which blood is exposed to a fixed quantity of glucose oxidase for a finite period of time to estimate concentration. After the specified time, excess blood is removed and the color is allowed to develop, which is used to estimate glucose concentration. For example, glucose oxidase reaction with glucose forms nascent oxygen, which converts potassium iodide (in the filter paper) to iodine, forming a brown color. The concentration of glycosylated hemoglobin as an indirect read of the level of glucose in the blood. When hemolysates of red cells are chromatographed, three or more small peaks named hemoglobin A1a, A1b, and A1c are eluted before the main hemoglobin A peak. These "fast" hemoglobins are formed by the irreversible attachment of glucose to the hemoglobin in a two-step reaction. Hexokinase can be measured in an assay in which glucose is phosphorylated by hexokinase (HK) in the presence of adenosine triphosphate (ATP) and magnesium ions to produce glucose-6-phosphate and adenosine diphosphate (ADP). Glucose-6-phosphate dehydrogenase (G6P-DH) specifically oxidises glucose-6-phosphate to gluconate-6-phosphate with the concurrent reduction of NAD+ to NADH. The increase in absorbance at 340 nm is proportional to the glucose concentration in the sample. HDL, LDL, triglycerides can be measured using the Abell-Kendall protocol that involves color development with Liebermann-Burchard reagent (mixed reagent of acetic anhydride, glacial acetic acid, and concentrated sulfuric acid) at 620 nm after hydrolysis and extraction of cholesterol. A fluorometric analysis may be used utilized to determine triglyceride reference values. Plasma high-density lipoprotein cholesterol (HDL-C) determination is measured by the same procedures used for plasma total cholesterol, after precipitation of apoprotein B-containing lipoproteins in whole plasma (LDL and VLDL) by heparin-manganese chloride. These compounds can also be detected colorimetrically in an assay that is based on the enzyme driven reaction that quantifies both cholesterol esters and free cholesterol. Cholesterol esters are hydrolyzed via cholesterol esterase into cholesterol, which is then oxidized by cholesterol oxidase into the ketone cholest-4-en-3-one plus hydrogen peroxide. The hydrogen peroxide is then detected with a highly specific colorimetric probe. Horseradish peroxidase catalyzes the reaction between the probe and hydrogen peroxide, which bind in a 1:1 ratio. Samples may be compared to a known concentration of cholesterol standard.

Data Processing.

In certain embodiments, the subject device is configured to process data derived from reading the CROF device. The device may be configured in any suitable way to process the data for use in the subject methods. In certain embodiments, the device has a memory location to store the data and/or store instructions for processing the data and/or store a database. The data may be stored in memory in any suitable format.

In certain embodiments, the device has a processor to process the data. In certain embodiments, the instructions for processing the data may be stored in the processor, or may be stored in a separate memory location. In some embodiments, the device may contain a software to implement the processing.

In certain embodiments, a device configured to process data acquired from the CROF device device contains software implemented methods to perform the processing. Software implemented methods may include one or more of: image acquisition algorithms; image processing algorithms; user interface methods that facilitate interaction between user and computational device and serves as means for data collection, transmission and analysis, communication protocols; and data processing algorithms. In certain embodiments, image processing algorithms include one or more of: a particle count, a LUT (look up table) filter, a particle filter, a pattern recognition, a morphological determination, a histogram, a line profile, a topographical representation, a binary conversion, or a color matching profile.

In certain embodiments, the device is configured to display information on a video display or touchscreen display when a display page is interpreted by software residing in memory of the device. The display pages described herein may be created using any suitable software language such as, for example, the hypertext markup language ("HTML"), the dynamic hypertext markup language ("DHTML"), the extensible hypertext markup language ("XHTML"), the extensible markup language ("XML"), or another software language that may be used to create a computer file displayable on a video or other display in a manner perceivable by a user. Any computer readable media with logic, code, data, instructions, may be used to implement any software or steps or methodology. Where a network comprises the Internet, a display page may comprise a webpage of a suitable type.

A display page according to the invention may include embedded functions comprising software programs stored on a memory device, such as, for example, VBScript routines, JScript routines, JavaScript routines, Java applets, ActiveX components, ASP.NET, AJAX, Flash applets, Silverlight applets, or AIR routines.

A display page may comprise well known features of graphical user interface technology, such as, for example, frames, windows, scroll bars, buttons, icons, and hyperlinks, and well known features such as a "point and click" interface or a touchscreen interface. Pointing to and clicking on a graphical user interface button, icon, menu option, or hyperlink also is known as "selecting" the button, option, or hyperlink. A display page according to the invention also may incorporate multimedia features, multi-touch, pixel sense, IR LED based surfaces, vision-based interactions with or without cameras.

A user interface may be displayed on a video display and/or display page. The user interface may display a report generated based on analyzed data relating to the sample, as described further below.

The processor may be configured to process the data in any suitable way for use in the subject methods. The data is processed, for example, into binned data, transformed data (e.g., time domain data transformed by Fourier Transform to frequency domain), or may be combined with other data. The processing may put the data into a desired form, and may involve modifying the format of data. Processing may include detection of a signal from a sample, correcting raw data based on mathematical manipulation or correction and/or calibrations specific for the device or reagents used to examine the sample; calculation of a value, e.g., a concentration value, comparison (e.g., with a baseline, threshold, standard curve, historical data, or data from other sensors), a determination of whether or not a test is accurate, highlighting values or results that are outliers or may be a cause for concern (e.g., above or below a normal or acceptable range, or indicative of an abnormal condition), or combinations of results which, together, may indicate the presence of an abnormal condition, curve-fitting, use of data as the basis of mathematical or other analytical reasoning (including deductive, inductive, Bayesian, or other reasoning), and other suitable forms of processing. In certain embodiments, processing may involve comparing the processed data with a database stored in the device to retrieve instructions for a course of action to be performed by the subject.

In certain embodiments, the device may be configured to process the input data by comparing the input data with a database stored in a memory to retrieve instructions for a course of action to be performed by the subject. In some embodiments, the database may contain stored information that includes a threshold value for the analyte of interest. The threshold value may be useful for determining the presence or concentration of the one or more analytes. The threshold value may be useful for detecting situations where an alert may be useful. The data storage unit may include records or other information that may be useful for generating a report relating to the sample.

In certain embodiments, the device may be configured to receive data that is derived from the CROF device. Thus in certain cases, the device may be configured to receive data that is not related to the sample provided by the subject but may still be relevant to the diagnosis. Such data include, but are not limited to the age, sex, height, weight, individual and/or family medical history, etc. In certain embodiments, the device is configured to process data derived from or independently from a sample applied to the CROF device.

20 Packages

Another aspect of the present invention is related to packaging, which would prolong the lifetime of the reagent used and facilitate the easy of the use.

In some embodiments, the plates in CROF with or without reagents are put inside a package, either one plate per package or more than one plates per package. In one embodiment, the first plate and second plate are packaged in a different package before a use. In some embodiments, different assays share a common first plate or a common second plate.

In some embodiments, each of the packages is sealed. In some embodiments, the seal is for preventing the air, chemicals, moisture, contamination, or any combination of them from outside of the package from entering inside the package. In some embodiments, the package is vacuum sealed or fill with nitrogen gas, or inner gases. In some embodiments, a material that can prolong a shelf-life-time of the plate and/or the reagents (including the capture agents, detection agents, etc.) is packaged inside the package with a plate.

In some embodiments, the package materials are a thin layer form, so that the package can be easily torn apart by a human hand.

21. Homogenous Assay Using a Signal Amplification Surface

In many applications of an assay, particularly in PoC or other fast assays, it is desirable to avoid washing steps. One aspect of the present invention is related to the devices, systems, and methods that can avoid washing of the assay.

By incorporating and/or using a signal amplification surface, the disclosed devices, systems, and methods may facilitate performing assays without washing. The surface amplification surface may only amplify the light emitted in a small distance from the surface (e.g. 20 nm, or 50 nm, or 100 nm). One example of the surface amplification layer is D2PA.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

What is claimed is:

1. A device for collecting and analyzing a vapor condensate (VC) sample, comprising:
   a collection plate and a cover plate, wherein:
   i. the plates are movable relative to each other into different configurations;
   ii. one or both plates are flexible;
   iii. each of the plates has, on its respective surface, a sample contact area for contacting a vapor condensate (VC) sample that contains an analyte;
   iv. one or both of the plates comprise spacers, wherein at least one of the spacers is inside the sample contact area;
   wherein one of the configurations is an open configuration, in which: the two plates are either completely or partially separated apart, the spacing between the plates is not regulated by the spacers, and the VC sample is deposited on one or both of the plates by directly condensing a vapor on the plate or the plates; and wherein another of the configurations is a closed configuration which is configured after the VC sample deposition in the open configuration; and in the closed configuration: at least a part of the VC sample is between the two plates and in contact with the two plates, and has a highly uniform thickness that is regulated by the spacers and the two sample surfaces of the plates and is equal to or less than 30 um with a small variation.

2. The device of claim 1, wherein the device further comprises a dry reagent coated on one or both of the plates.

3. The device of claim 1, wherein the device further comprises, on the one or both plates, a dry binding site that has a predetermined area, wherein the dry binding site binds to and immobilizes the analyte in the sample.

4. The device of claim 1, wherein the sample is an exhale breath condensate, wherein the exhale breath condensate directly condenses on one or both the sample contacting areas.

5. The device of claim 1, wherein the sample is a vapor from a biological sample, an environmental sample, a chemical sample, or a clinical sample.

6. The device of claim 1, wherein the analyte comprises a molecule (e.g., a protein, peptides, DNA, RNA, nucleic acid, or other molecules), cells, tissues, viruses, or nanoparticles with different shapes.

7. The device of claim 1, wherein the analyte comprises a volatile organic compound (VOCs).

8. The device of claim 1, wherein the analyte comprises nitrogen, oxygen, CO2, H2O, or inert gases.

9. The device of claim 1, wherein the analyte is stained.

10. The device of claim 1, wherein the highly uniform thickness has a value (i) equal to or less than 0.5 um, (ii) in the range of 0.5 um to 1 um, (iii) in the range of 1 um to 2 um, or (iv) in the range of 2 um to 10 um.

11. The device of claim 1, wherein a material of the plate and the spacers are independently selected from the group consisting of polystyrene, PMMA, PC, COC, COP, and another plastic.

12. The device of claim 1, wherein the inter-spacer distance is (i) in the range of 1 um to 200 um, or (ii) in the range of 200 um to 1000 um.

13. The device of claim 1, wherein the VC sample is an exhaled breath condensate from a human or an animal.

14. The device of claim 1, wherein the spacers regulating the layer of uniform thickness have a filling factor of at least 1%, wherein the filling factor is a ratio of a spacer area in contact with the layer of uniform thickness to a total plate area in contact with the layer of uniform thickness.

15. The device of claim 1, wherein for spacers regulating the layer of uniform thickness, a Young's modulus of the spacers times a filling factor of the spacers is equal to or larger than 10 MPa, wherein the filling factor is the ratio of a spacer area in contact with the layer of uniform thickness to a total plate area in contact with the layer of uniform thickness.

16. The device of claim 1, wherein for a flexible plate, a thickness of the flexible plate times a Young's modulus of the flexible plate is in the range of 60 to 750 GPa-um.

17. The device of claim 1, wherein for a flexible plate, a fourth power of the inter-spacer distance (ISD) divided by a thickness of the flexible plate (h) and a Young's modulus (E) of the flexible plate, $ISD^4/(hE)$, is equal to or less than $10^6$ $um^3/GPa$.

18. The device of claim 1, wherein the layer of uniform thickness of the sample is uniform over a lateral area that is at least 1 $mm^2$.

19. The device of claim 1, wherein the device is configured to analyze the sample in 60 seconds or less.

20. The device of claim 1, wherein the device further comprises, on one or both of the plates, one or a plurality of amplification sites that are each capable of amplifying a signal from the analyte or a label of the analyte when the analyte or label is within 500 nm from the amplification site.

21. The device of claim 1, wherein the device further comprises a detector, wherein the detector is (i) an optical detector for detecting an optical signal, or (ii) an electrical detector for detecting an electrical signal.

22. A system for rapidly analyzing a vapor condensation sample using a mobile communication device comprising:
 (a) a device of claim 1; and
 (b) a mobile communication device comprising:
  i. one or a plurality of cameras for detecting a signal and/or imaging the vapor condensate sample; and
  ii. electronics, signal processors, hardware and software for receiving and/or processing the detected signal and/or the image of the vapor condensate sample and for remote communication.

23. A method for analyzing an analyte in a vapor condensate sample, comprising:
 obtaining a device of claim 1;
 depositing a vapor condensate (VC) sample onto one or both plates of the device, wherein the deposition is by condensing the vapor directly on the one or both plates;
 bringing the two plates into a closed configuration; and
 analyzing the analyte in the layer of uniform thickness while the plates are in the closed configuration.

24. The method of claim 23, further comprising removing the external force after the plates are in the closed configuration; imaging the analytes in the layer of uniform thickness while the plates are the closed configuration; and counting a number of analytes or the labels in an area of the image.

25. The method of claim 23, wherein the external force is provided by a human hand.

26. A method for analyzing an analyte in a vapor condensate sample, wherein the method comprises:
 (a) obtaining a sample;
 (b) obtaining the device of claim 1 wherein the spacers have:
  i. a pillar shape with substantially uniform cross-section and a flat top surface;
  ii. a ratio of the width to the height equal to or larger than one;
  iii. a predetermined constant inter-spacer distance that is in the range of 10 um to 200 um; and
  iv. a filling factor equal to 1% or larger; and
 (c) depositing the sample on one or both of the plates when the plates are configured in the open configuration;
 (d), after (c), using the two plates to compress at least part of the sample into the layer of substantially uniform thickness that has an average value equal to or less than 30 um with a variation of less than 10%, wherein the compressing comprises:
  bringing the two plates together; and
  conformable pressing, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers; and (e) analyzing the analyte in the layer of uniform thickness while the plates are the closed configuration;

wherein the filling factor is the ratio of the spacer contact area to the total plate area;

wherein a conformable pressing is a method that makes the pressure applied over an area is substantially constant regardless the shape variation of the outer surfaces of the plates; and wherein the parallel pressing applies the pressures on the intended area at the same time, and a sequential pressing applies the pressure on a part of the intended area and gradually move to other area.

27. The method of claim 26, wherein the analyzing step comprises counting the analyte in the sample, and wherein an imaging and the counting is done by:
  i. illuminating the cells in the layer of uniform thickness;
  ii. taking one or more images of the cells using a CCD or CMOS sensor;
  iii. identifying cells in the image using a computer; and
  iv. counting a number of cells in an area of the image.

28. The method of claim 26, wherein the device further comprises a dry reagent that is coated on one or both plates.

29. The method of claim 26, wherein the analyte comprises a molecule (e.g., a protein, peptides, DNA, RNA, nucleic acid, or other molecules), cells, tissues, viruses, nanoparticles with different shapes, volatile organic compounds (VOCs), nitrogen, oxygen, $CO_2$, $H_2O$, or inert gases.

30. The method of claim 26, wherein the substantially uniform thickness has a value between 0.5 um to 10 um.

* * * * *